(12) United States Patent (10) Patent No.: US 8,034,926 B2
Viswanath et al. (45) Date of Patent: *Oct. 11, 2011

(54) METHODS OF MANUFACTURING CRYSTALLINE FORMS OF RAPAMYCIN ANALOGS

(75) Inventors: Shekhar Viswanath, Vernon Hills, IL (US); Larry Bartelt, Highland Park, IL (US); Robert Leanna, Grayslake, IL (US); Michael Rasmussen, Racine, WI (US); Madhup Dhaon, Mundelein, IL (US); Rodger Henry, Wildwood, IL (US); Thomas Borchardt, Kenosha, WI (US); Shuang Chen, Gurnee, IL (US); Geoff Zhang, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/886,398

(22) Filed: Sep. 20, 2010

(65) Prior Publication Data

US 2011/0009618 A1 Jan. 13, 2011

Related U.S. Application Data

(63) Continuation of application No. 11/781,807, filed on Jul. 23, 2007, now Pat. No. 7,820,812.

(51) Int. Cl.
*C07D 498/18* (2006.01)
(52) U.S. Cl. ........................................................ 540/456
(58) Field of Classification Search ................... 540/456
See application file for complete search history.

(56) References Cited

U.S. PATENT DOCUMENTS

| 5,527,907 | A | 6/1996 | Or et al. |
| 6,015,815 | A | 1/2000 | Mollison |
| 2003/0129215 | A1 | 7/2003 | Mollison et al. |
| 2008/0085880 | A1 | 4/2008 | Viswanath et al. |

FOREIGN PATENT DOCUMENTS

| WO | WO 99/15530 | 4/1999 |
| WO | WO 2006/023627 | 3/2006 |
| WO | WO 2006/060616 | 6/2006 |
| WO | WO 2008/014222 | 1/2008 |

OTHER PUBLICATIONS

European Search Report for 07799771.6, mailed Sep. 23, 2009, 7 pgs.
Non Final Office Action for U.S. Appl. No. 11/840,119, mailed Dec. 23, 2009, 22 pgs.
Final Office Action for U.S. Appl. No. 11/840,119, mailed Aug. 5, 2010, 15 pgs.
Advisory Action for U.S. Appl. No. 11/840,119, mailed Jan. 31, 2011, 3 pgs.
Wagner et al, "Rapamycin Analogs With Reduced Systemic Exposure," Bioorganic & Medicinal Chemistry Letters 2005.
Pagano, Thomas G. "Spectral Assignments and Reference Data", Magnetic Resonance in Chemistry, Dec. 13, 2004.

*Primary Examiner* — Bruck Kifle
(74) *Attorney, Agent, or Firm* — Squire, Sanders & Dempsey (US) LLP

(57) ABSTRACT

A process for preparing a crystalline rapamycin analog includes: combining the rapamycin analog with an organic medium to form a mixture; incubating the mixture until the rapamycin analog crystallizes; and recovering the crystalline rapamycin analog. The organic medium can be a solvent, and the process can include causing the rapamycin analog to dissolve into the solvent, and incubating the solvent until the rapamycin analog crystallizes. The following can also be performed: forming a slurry of crystalline rapamycin analog; stirring the rapamycin analog mixture until the rapamycin analog crystallizes; saturating the rapamycin analog solution; forming a supersaturated rapamycin analog solution; combining an antisolvent with the rapamycin analog and the solvent to form a biphasic mixture, and incubating the biphasic mixture to cause a liquid-liquid phase split.

25 Claims, 25 Drawing Sheets

METHODS OF MANUFACTURING CRYSTALLINE FORMS OF RAPAMYCIN ANALOGS

CROSS-REFERENCE TO RELATED APPLICATIONS

This application is a continuation application of U.S. application Ser. No. 11/781,807 filed on Jul. 23, 2007, which claims the benefit of U.S. Provisional Patent Application Ser. No. 60/820,317, filed Jul. 25, 2006, and entitled "CRYSTALLINE FORMS OF RAPAMYCIN ANALOGS," with Shekhar Viswanath, Larry Bartelt, Robert Leanna, Michael Rasmussen, Madhup Dhaon, Rodger Henry, Thomas Borchardt, and Geoff Zhang as inventors, the teachings of which are incorporated herein by specific reference.

FIELD OF THE INVENTION

The present invention relates to crystalline forms of rapamycin analogs as well as compositions, uses, and methods for making the same. More particularly, the present invention relates to crystalline forms of the rapamycin analog zotarolimus (i.e., ABT-578).

BACKGROUND OF THE INVENTION

In pharmaceuticals, there are typically trade-offs between drug solubility, stability, absorption, and bioavailability which can be modulated by the form of the drug. Some forms of active compounds suffer from very low solubility or insolubility in water and undergo extensive first hepatic pass metabolism. Some forms of active compounds suffer from poor absorption due to their low water solubility. Properties of a solid form of an active compound, such as its crystal habit and morphology, can significantly affect its properties. As such, selection of a form of an active component can therefore significantly alter the performance of pharmaceuticals and other chemical products. Traditionally, rapamycin and rapamycin analogs have been prepared in amorphous forms within pharmaceutical compositions.

Despite the development and research of crystallization methods, control over crystallization based on structural understanding and the ability to design crystals and other solid-forms is still limited. The control on nucleation, growth, dissolution, and morphology of molecular crystals remains primarily a matter of "mix and try" (Weissbuch, I., Lahav, M., and Leiserowitz, L., Molecular Modeling Applications in Crystallization, 166, 1999). Because many variables influence crystallization, precipitation, phase shift, and the solid-forms produced therefrom and because so many reagents and process variables are available, testing of individual solid-formation and crystal structure modification is an extremely tedious process. Despite the importance of crystal structure in the pharmaceutical industry, optimal crystal structures or optimal amorphous solids are not vigorously or systematically sought. Thus, the selection of a form of a rapamycin analog, such as a crystalline form, can significantly alter its performance in a specific application, and such forms continue to be sought.

Therefore, it would be beneficial to have a crystalline form of a rapamycin analog that can be used in therapeutic treatments. Additionally, it would be beneficial to have compositions, methods of use, and methods of manufacture for the crystalline form of the rapamycin analog.

SUMMARY OF THE INVENTION

The invention relates to compositions, uses, and method for making crystalline forms of rapamycin analogs, and more specifically, crystalline forms of zotarolimus (i.e., ABT-578).

In one embodiment, the present invention includes a crystalline form of a rapamycin analog. The crystalline forms of the rapamycin analog can be prepared by various methods, which are described herein. Such crystalline forms can be prepared so that a suitable crystalline form can be identified for a particular use. The rapamycin analog can have a structure of Formula 1, Formula 2, or Formula 3 as illustrated below. Also, the crystalline rapamycin analog can be a prodrug, salt, derivative, or combination thereof.

FORMULA 1

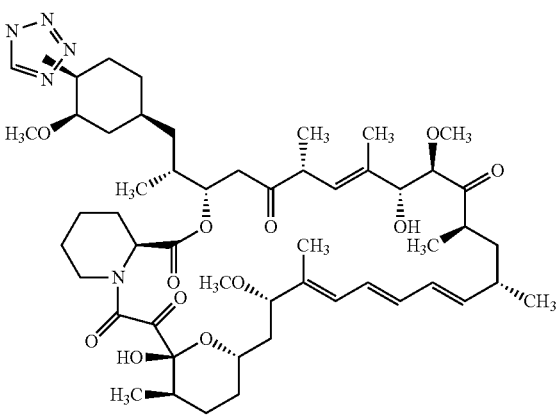

FORMULA 2

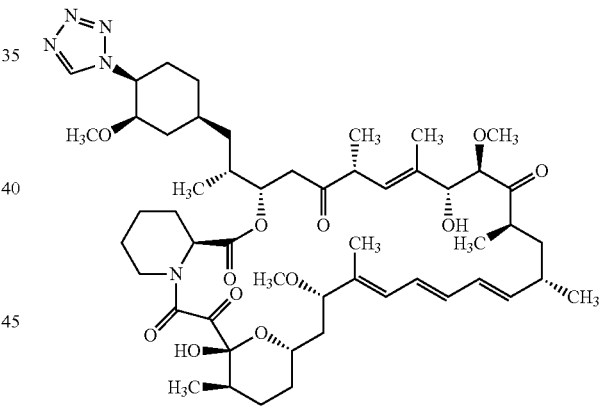

FORMULA 3

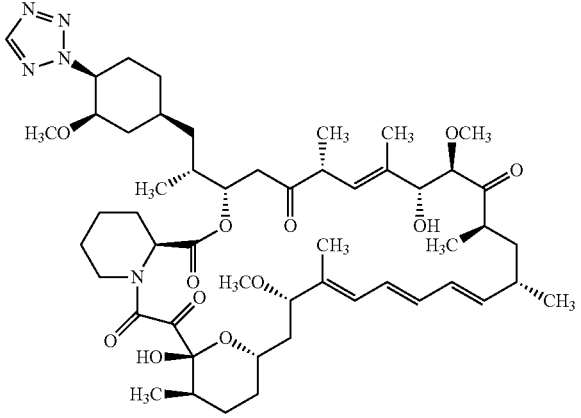

In one embodiment, the crystal is a solvate. As such, the crystal can include an organic solvent included therein, where the solvent is used to prepare the crystal. The organic solvent can be selected from the group consisting of solvents that can be used in preparing the rapamycin analog include acetone, ethyl acetate, methanol, ethanol, n-propanol, isopropanol, isobutanol, tertbutanol, 2-butanol, acetonitrile, tetrahydrofuran, isobutyl acetate, n-butyl acetate, ethyl formate, n-propyl acetate, isopropyl acetate, methylethyl ketone, toluene, N,N dimethyl formamide, anisole, methyl isopropyl ketone, nitromethane, propionitrile, 2-butanone (i.e., methyl ethyl ketone or MEK), tetrahydrofuran, 1,2-dimethoxyethane, isopropyl acetate, any combination thereof, and the like.

In one embodiment, the crystal is a desolvate. As such, the crystal can be selected from the group consisting of an acetone desolvate, toluene desolvate, acetonitrile desolvate, ethyl formate desolvate, isobutyl acetate desolvate, N,N dimethyl formamide, and any combination thereof.

In one embodiment, the present invention includes a process for preparing a crystalline form of a rapamycin analog. Such a process comprises the following: combining the rapamycin analog with at least one organic medium to form a mixture; incubating the mixture until the rapamycin analog crystallizes; and recovering the crystalline rapamycin analog from the organic medium.

In one embodiment, the organic medium can be comprised of at least one solvent to form the mixture. As such, the process for preparing the crystalline form of the rapamycin analog includes causing the rapamycin analog to dissolve into the solvent, and incubating the solvent until the rapamycin analog crystallizes.

In one embodiment, the process includes forming a slurry of crystalline rapamycin analog in the solution. In one embodiment, the process includes stirring the rapamycin analog mixture until the rapamycin analog crystallizes. In one embodiment, the process includes saturating the rapamycin analog solution. This can include forming a supersaturated rapamycin analog solution.

In one embodiment, the process includes the use of an antisolvent to aid in forming the crystalline rapamycin analog. Such a method includes combining at least one antisolvent with the rapamycin analog and the solvent to form a biphasic mixture, and incubating the biphasic mixture to cause a liquid-liquid phase split with a majority of the rapamycin analog being in the solvent and a minority of the rapamycin analog being in the antisolvent. Optionally, the solvent can be separated from the antisolvent before the crystals are separated out.

It is to be understood that the foregoing general description and the following detailed description are exemplary and explanatory only and are not to be viewed as being restrictive of the present invention, as claimed. Further advantages of this invention will be apparent after a review of the following detailed description of the disclosed embodiments which are illustrated schematically in the accompanying drawings and in the appended claims.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
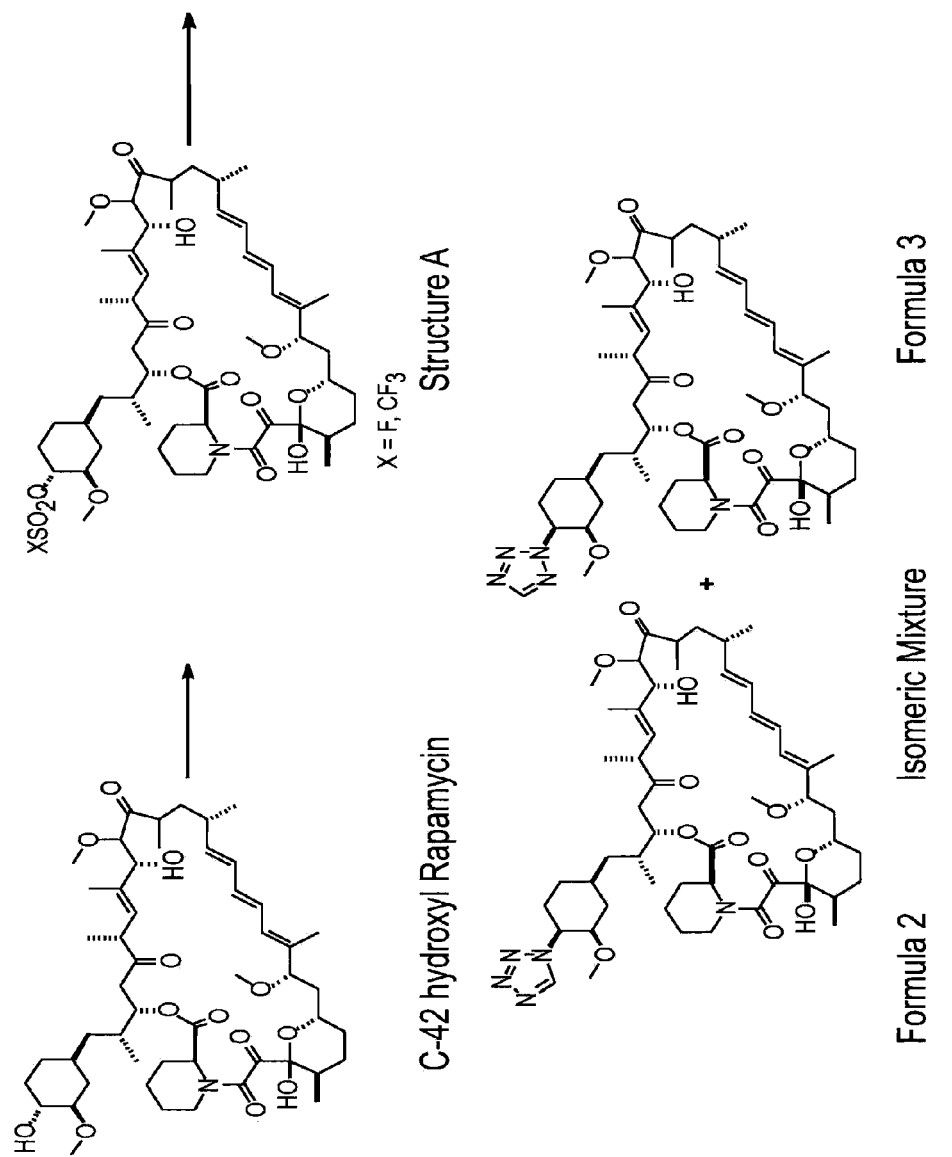
FIG. 1 shows a schematic representation of an embodiment of a method of preparing a rapamycin analog.

Generally, the present invention relates to crystal habits, compositions, uses, and methods for making crystalline forms of rapamycin analogs, such as the rapamycin analog zotarolimus (i.e., ABT-578). The crystalline forms of the rapamycin analog can be prepared by various methods, which are described herein. Such crystalline forms can be prepared so that a suitable crystalline form can be identified for a particular use.

I. Crystalline Rapamycin Analogs

In one embodiment, the rapamycin analog can have the structure of Formula 1, Formula 2, Formula 3, or a combination thereof.

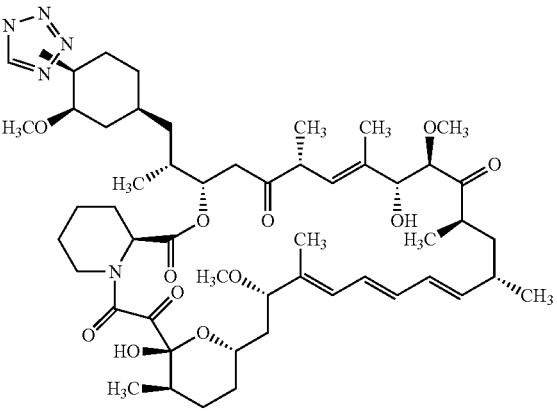

FORMULA 1

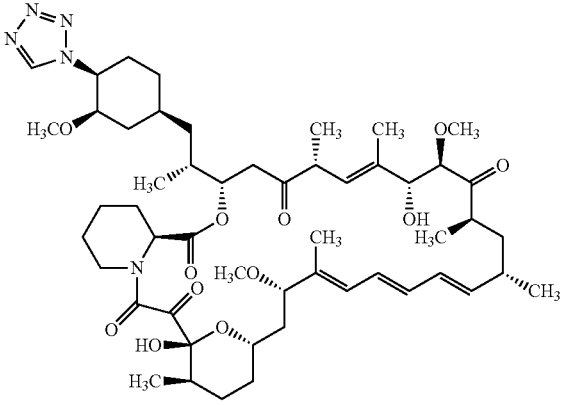

FORMULA 2

-continued

FORMULA 3

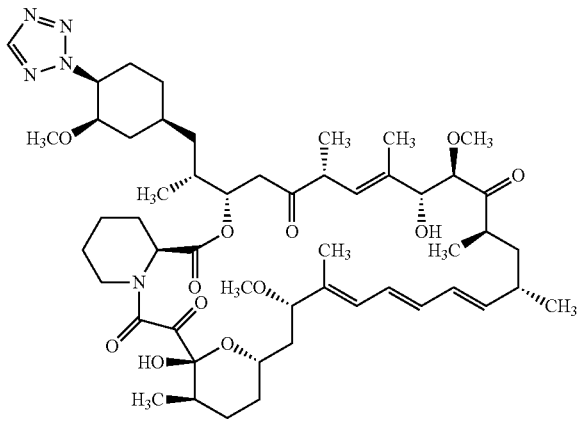

The rapamycin analog for Formula 2 can be referred to as zotarolimus or ABT-578. Additionally, the drug can be any pharmaceutically acceptable salt or prodrug of the rapamycin analog. The preparation of pharmaceutically acceptable salts and/or prodrugs of bioactive agents, such as zotarolimus, are well known in the art.

Additionally, the rapamycin analogs of Formulas 1-3 can exist in equilibrium in solution with another analog as shown in Formula 4. The rapamycin analog of Formula 4 can also be the corresponding analogs of Formulas 2-3. As such, the raparnycin analog of Formula 4 (and the equivalents to Formulas 2-3) can also form crystals or be incorporated into the crystals of the rapamycin analogs of Formulas 1-3.

FORMULA 4

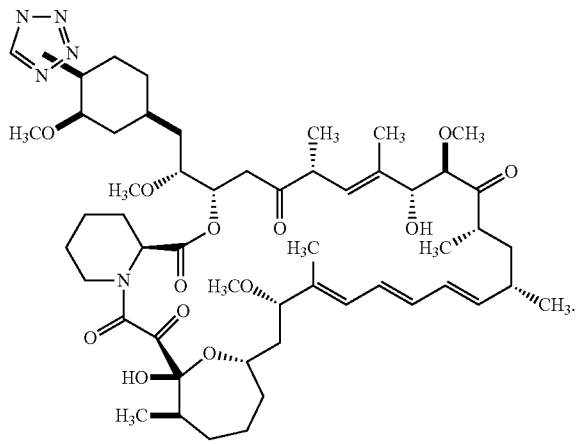

In one embodiment, the rapamycin analog can be a derivative of the analogs shown in Formulas 1-4. A derivative can be prepared by making minor substitutions such as hydroxylating, methylating, ethylating, or otherwise minimally altering a substitutent.

In some instances, the rapamycin analog can be formed into salts, if possible, comprising pharmacologically acceptable anions including acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate, methylsulfate, muscate, napsylate, nitrate, panthotlienate, phosphate/diphosphate, polygalacturonate, salicylate, stearate, succinate, sulfate, tannate, tartrate, teoclate, triethiodide, and pamoate (i.e., 1,1'-methylene-bis-(2-hydroxy-3-naphthoate)).

A. Crystalline Forms

The various crystalline rapamycin analogs of the present invention can have different properties. That is, the crystals can have different structural, physical, pharmacological, or chemical characteristics. Structural properties include, but are not limited to, the crystalline polymorphic form and a description of the crystal habit. Structural properties also include the composition, such as whether the solid-form is a hydrate, dehydrate, solvate, desolvate, salt, combination thereof, and the like.

Also, the physical state of a crystalline rapamycin analog can be further divided into: (1) whether the crystal matrix includes a co-adduct; (2) morphology (e.g., crystal habit); and (3) internal structure (e.g., polymorphism). In a co-adduct, the crystal matrix can include either a stoichiometric or non-stoichiometric amount of the adduct, for example, a crystallization solvent or water (e.g., a solvate or a hydrate). Non-stoichiometric solvates and hydrates include inclusions or clathrates, that is, where a solvent or water is trapped at random intervals within the crystal lattice matrix. A stoichiometric solvate or hydrate is where a crystal matrix includes a solvent or water at specific sites in a specific ratio. That is, the solvent or water molecule can be part of the crystal matrix in a defined arrangement. Additionally, the physical state of a crystal matrix can change by removing a co-adduct, originally present in the crystal matrix. For example, if a solvent or water is removed from a solvate or a hydrate, a hole is formed within the crystal matrix, thereby forming a new physical state. Such physical states are referred to herein as dehydrated hydrates (i.e., dehydrates) or desolvated solvates (i.e., desolvates).

The crystal habit is the description of the outer appearance of an individual crystal. For example, a crystal may have a cubic, tetragonal, orthorhombic, monoclinic, triclinic, rhomboidal, or hexagonal shape.

The internal structure of a crystal refers to the crystalline form or polymorphism. A given compound, such as a rapamycin analog, may exist as different polymorphs, that is, distinct crystalline species. In general, different polymorphs of a given compound can be as different in structure and properties as the crystals of two different compounds. Solubility, melting point, density, hardness, crystal shape, optical and electrical properties, vapor pressure, stability, and the like can vary with the polymorphic form.

The crystalline structure of a compound, such as a rapamycin analog, plays an important role in determining the properties that affect bioavailability and effectiveness as a pharmaceutical. The properties of many compound, can be modified by structural changes. For example, different polymorphs or crystals of the same pharmaceutical compound can have different therapeutic activities. Understanding structure-property relationships can be important in efforts to maximize the desirable properties of rapamycin analogs, such as the therapeutic effectiveness of a pharmaceutical.

B. Crystallization

The process of crystallization is one of ordering the rapamycin analog in a solid lattice structure. During this process, randomly organized molecules in a solution; a melt, or the gas phase take up regular positions in the lattice structure. The regular organization of the lattice is responsible for many of the unique properties of crystals, including the diffraction of x-rays, defined melting point, and sharp, well-defined crystal faces. While precipitation usually refers to formation of amorphous substances that have no symmetry or ordering and cannot be defined by habits or as polymorphs, it can also refer to the process of forming crystals by precipitation. Both crystallization and precipitation result from the inability of a solution to fully dissolve the rapamycin analog and can be induced by changing the state (e.g., varying parameters) of the composition in some way.

Some of the important processes in crystallization are nucleation, growth kinetics, interfacial phenomena, agglomeration, and breakage. Nucleation results when the phase-transition energy barrier is overcome, thereby allowing a particle to form from a supersaturated solution. Crystal growth is the enlargement of crystal particles caused by deposition of the rapamycin analog on an existing surface of the crystal. The relative rate of nucleation and growth determine the size distribution of the crystals that are formed. The thermodynamic driving force for both nucleation and growth is supersaturation, which is defined as the deviation from thermodynamic equilibrium. Agglomeration is the formation of larger particles through two or more particles (e.g., crystals) sticking together and forming a larger crystalline structure.

Rapamycin analogs can assume many different crystal forms and sizes depending on the protocol and conditions for forming the crystalline form. Particular emphasis has been put on the crystal characteristics in the pharmaceutical industry (e.g., polymorphic form, size, crystal habit, and crystal-size distribution) because crystal structure and size can affect manufacturing, formulation, and pharmacokinetics, including bioavailability. There are four broad classes by which crystals of a given compound may differ: composition; habit; polymorphic form; and crystal size.

The crystal composition typically describes whether the solid-form is a single compound, such as pure rapamycin analog, or is a mixture of compounds. For example, solid-forms can be present in their neutral form, such as the free base of a compound having a basic nitrogen or as a salt (e.g., the hydrochloride salt of a basic nitrogen-containing compound). A crystal composition can also describe crystals containing adduct molecules. During crystallization or precipitation, an adduct molecule (e.g., a solvent or water) can be incorporated into the crystalline lattice matrix, adsorbed on the surface, or trapped within the lattice of the crystal. Such compositions are referred to as inclusions, such as hydrates (e.g., water molecule incorporated in the lattice) and solvates (e.g., solvent trapped within a lattice), Whether a crystal forms as an inclusion can have a profound effect on the properties, such as the bioavailability or ease of processing or manufacture of the rapamycin analog. For example, inclusions may dissolve more or less readily or have different mechanical properties or strengths than the corresponding non-inclusion crystal structures of the same compound.

Accordingly, the rapamycin analog can crystallize in different external shapes depending on, amongst others, the composition and temperature of the crystallizing medium. The crystal-face shapes are described as the crystal habit. Such information is important because the crystal habit has a large influence on the surface-to-volume ratio of the crystal. Although different crystal habits can have the same internal structure and identical single crystal patterns, they can still exhibit different pharmaceutical properties (Haleblian 1975. J. Pharm. Sci., 64:1269). Crystal habit can influence several pharmaceutical characteristics, for instance, mechanical factors, such as syringeability, tableting behavior, filtration, drying, and mixing with other substances (e.g., excipients) and non-mechanical factors such as dissolution rate.

Additionally, the same rapamycin analog can crystallize as more than one distinct crystalline species (e.g., having a different internal lattice structure) or shift from one crystalline species to another. This phenomena is known as polymorphism, and the distinct species are known as polymorphs. Polymorphs can exhibit different optical properties, melting points, solubilities, chemical reactivities, dissolution rates, and different bioavailabilities. It is well known that different polymorphs of the same pharmaceutical compound can have different pharmacokinetics. For example, one polymorph can be absorbed more readily than its counterpart. In the extreme, only one polymorphic form of a given pharmaceutical may be suitable for disease treatment. However, it is likely that the different polymorphs have different properties that can be utilized together or apart. For example, polymorphs having different solubility properties can be used together in order to customize release or elution profiles, or can be used in different formulations or therapies. Thus, the discovery and development of novel or beneficial rapamycin analog polymorplis is extremely important, especially in the pharmaceutical area.

Amorphous solids, such as traditional rapamycin and rapamycin analogs, have no crystal shape and cannot be characterized according to habit or polymorphic form. A common amorphous solid is glass in which the atoms and molecules exist in a non-uniform array. Amorphous solids are usually the result of rapid solidification and can be conveniently identified by x-ray powder diffraction, since these solids give very diffuse lines or no crystal diffraction pattern. While amorphous solids may often have desirable pharmaceutical properties, such as rapid dissolution rates, they are not usually preferred because of their physical and/or chemical instability. An amorphous solid is in a high-energy structural state relative to its crystalline form, and thus it may crystallize during storage or shipping. Also, an amorphous solid may be more sensitive to oxidation (Pikal et al., 1997, J. Pharm. Sci. 66:1312). Amorphous solids can be obtained by solidifying in such a way as to avoid the thermodynamically preferred crystallization process. They can also be prepared by disrupting an existing crystal structure.

Crystallization and precipitation are phase changes that result in the formation of a crystalline solid or an amorphous solid from a solution. Crystallization also includes polymorphic shift from one crystalline species to another. The most common type of crystallization is crystallization from solution in which a substance is dissolved at an appropriate temperature in a solvent, then the system is processed to achieve supersaturation followed by nucleation and crystal growth.

C. Crystallization Components

As stated above, solvents influence the crystallization and resulting rapamycin analog crystals. In general, most crystallization compositions contain a solvent as one of the components. Solvents may influence and direct the formation of crystals through polarity, viscosity, boiling point, volatility, charge distribution, and molecular shape. The solvent identity and concentration is one way to control saturation, Indeed, one can crystallize under isothermal conditions by simply adding a nonsolvent (i.e., antisolvent) to an initially subsaturated solution. Also, a solution of the rapamycin analog in which varying amounts of nonsolvent are added can change the crystallization and resulting crystal because the solubility of the rapamycin analog is exceeded when some critical amount of nonsolvent is added. Further addition of the nonsolvent increases the supersaturation of the solution and, therefore, the growth rate of the rapamycin analog crystals that are grown.

Mixed solvents also add the flexibility of changing the thermodynamic activity of one of the solvents independent of temperature. Thus, a hydrate or solvate can be produced at a given temperature simply by carrying out crystallization over a range of solvent compositions. For example, crystallization from a methanol-water solution that is very rich in methanol can favor crystal hydrates with fewer waters incorporated in the solid (e.g., dihydrate vs. hemihydrate) while a water rich solution will favor hydrates with more waters incorporated into the solid. The precise boundaries for producing the respective hydrates are found by examining the elements of the array when concentration of the solvent component is the variable.

In one embodiment, solvents that are generally accepted within the pharmaceutical industry for use in manufacture of pharmaceuticals are used in the crystallization of the rapamycin analog. Various mixtures of those solvents can also be used. The solubilities of the rapamycin analog is high in some solvents and low in others. Solutions can be mixed in which the high-solubility solvent is mixed with the low-solubility solvent until crystal formation is induced. Solvents include, but are not limited to, aqueous based solvents such as water or aqueous acids, bases, salts, buffers or mixtures thereof and organic solvents, such as protic, aprotic, polar or non-polar organic solvents.

Specific applications of the crystallizing compound may create additional requirements. For example, in the case of pharmaceuticals such as a rapamycin analog, solvents are selected based on their biocompatibility as well as the solubility. For example, the ease with which the rapamycin analog is dissolved in the solvent and the lack of detrimental effects of the solvent on the analog are factors to consider in selecting the solvent. Preferred organic solvents are volatile or have a relatively low boiling point or can be removed under vacuum and that are acceptable for administration to humans in trace amounts, such as methylene chloride. Other solvents, such as ethyl acetate, ethanol, methanol, dimethyl formamide, acetone, acetonitrile, tetrahydrofuran, acetic acid, dimethyl sulfoxide, and chloroform, and mixture thereof, also can be used. Preferred solvents are those rated as class 3 residual solvents by the Food and Drug Administration, as published in the Federal Register vol. 62, number 85, pp. 24301-24309 (May 1997). Solvents for rapamycin analogs that are administered parenterally or as a solution or suspension can more typically be distilled water, buffered saline, Lactated Ringer's, or some other pharmaceutically acceptable carrier.

Specific examples of solvents that can be used in preparing the rapamycin analog include acetone, ethyl acetate, methanol, ethanol, n-propanol, isopropanol, isobutanol, tertbutanol, 2-butanol, acetonitrile, tetrahydrofuran, isobutyl acetate, n-butyl acetate, ethyl formate, n-propyl acetate, isopropyl acetate, methylethyl ketone, toluene, N,N dimethyl formamide, anisole, methyl isopropyl ketone, nitromethane, propionitrile, 2-butanone 9 i.e., methyl ethyl ketone or MEK), tetrahydrofuran, 1,2-dimethoxyethane, isopropyl acetate, any combination thereof, and the like, Specific examples of antisolvents that can be used in preparing the rapamycin analog include cyclohexane, heptane, hexane, n-octane, iso-octane, methylcyclohexane, any combination thereof, and the like.

A specific example of a solvent/antisolvent system that can be used in preparing the rapamycin analog include acetone/heptane.

Other substances may also be added to the crystallization reactions that influence the generation of a crystalline form. These crystallization additives can be either reaction byproducts, related molecules, randomly screened compounds (such as those present in small molecule libraries), or any of various other additives found in pharmaceutical compositions. They can be used to either promote or control nucleation, to direct the growth or growth rate of a specific crystal or set of crystals, and any other parameter that affects crystallization. The influence of crystallization additives may depend on their relative concentrations and thus the invention provides methods to assess a range of crystallization additives and concentrations. Examples of crystallization additives include, but are not limited to, additives that promote and/or control nucleation, additives that a fleet crystal habit, and additives that affect polymorphic form.

Specific examples of crystallization additives that can be used in preparing the rapamycin analog include a rapamycin solvate, a rapamycin desolvate, a rapamycin hydrate, and a rapamycin dehydrate.

In still another embodiment, other substances can be used including solid phase GRAS compounds or alternatively, small molecule libraries (e.g., in solid phase).

The presence of surfactant-like molecules in the crystallization vessel may influence the crystal nucleation and selectively drive the growth of distinct polymorphic forms. Thus, surfactant-like molecules can be introduced into the crystallization vessel either by pre-treating or by direct addition to the crystallization medium. Surfactant molecules can be either specifically selected or randomly screened for their influence in directing crystallization. In addition, the effect of the surfactant molecule is dependent on its concentration in the crystallization vessel and thus the concentration of the surfactant molecules should be carefully controlled.

In some cases, direct seeding of crystallization reactions will result in an increased diversity of crystal forms being produced. In one embodiment, particles are added to the crystallization reactions. In another, nanometer-sized crystals (e.g., nanoparticles) are added to the crystallization reactions. These particles can be either nanometer sized or larger.

II. Crystalline Rapamycin Analogs

In one embodiment, the present invention includes a crystalline form of a rapamycin analog. The crystalline forms of the rapamycin analog can be prepared by various methods, which are described herein, Such crystalline forms can be prepared so that a suitable crystalline form can be identified for a particular use. The rapamycin analoa can have a structure of Formula 1, Formula 2, or Formula 3 as illustrated above. Also, the crystalline rapamycin analog can be a prodrug, salt, derivative, or combination thereof.

In one embodiment, the crystal is a solvate. As such, the crystal can include an organic solvent included therein. The organic solvent can be selected from the group consisting of acetone, ethyl acetate, methanol, ethanol, n-propanol, isopropanol, isobutanol, tertbutanol, 2-butanol, acetonitrile, tetrahydrofuran, isobutyl acetate, n-butyl acetate, ethyl formate, n-propyl acetate, isopropyl acetate, methylethyl ketone, toluene, N,N dimethyl formamide, anisole, and any combination thereof.

In one embodiment, the crystal is a desolvate. As such, the crystal can be selected from the group consisting of an acetone desolvate, toluene desolvate, acetonitrile desolvate, ethyl formate desolvate, isobutyl acetate desolvate, N,N-dimethyl formamide, and any combination thereof.

Figure 2A:
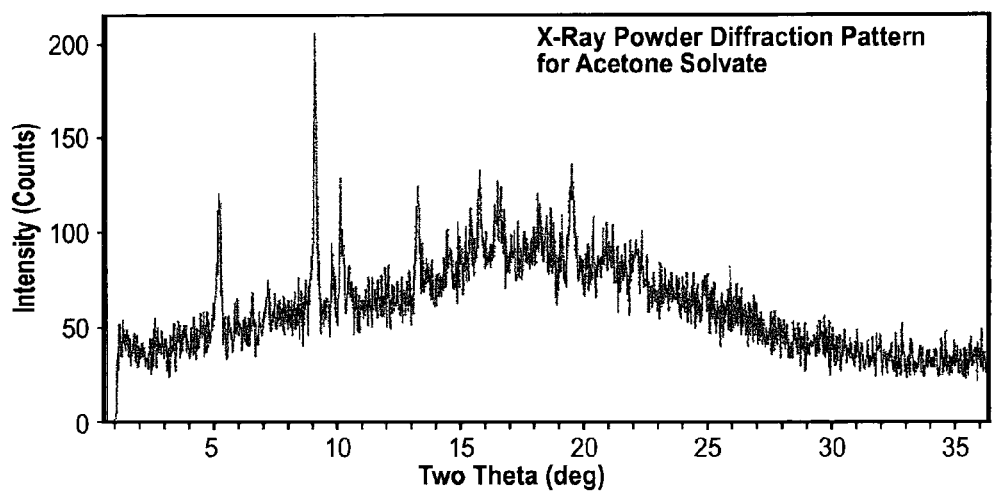
FIG. 2A is a graph illustrating a powder X-ray diffraction pattern of an embodiment of a crystalline form of a rapamycin analog acetone solvate.

In one embodiment, the crystalline rapamycin analog has a powder X-ray diffraction pattern with a peak at about 5.2, 9.1, and/or 13.2. Also, the powder X-ray diffraction pattern is substantially as shown in FIG. 2A.

Figure 2B:
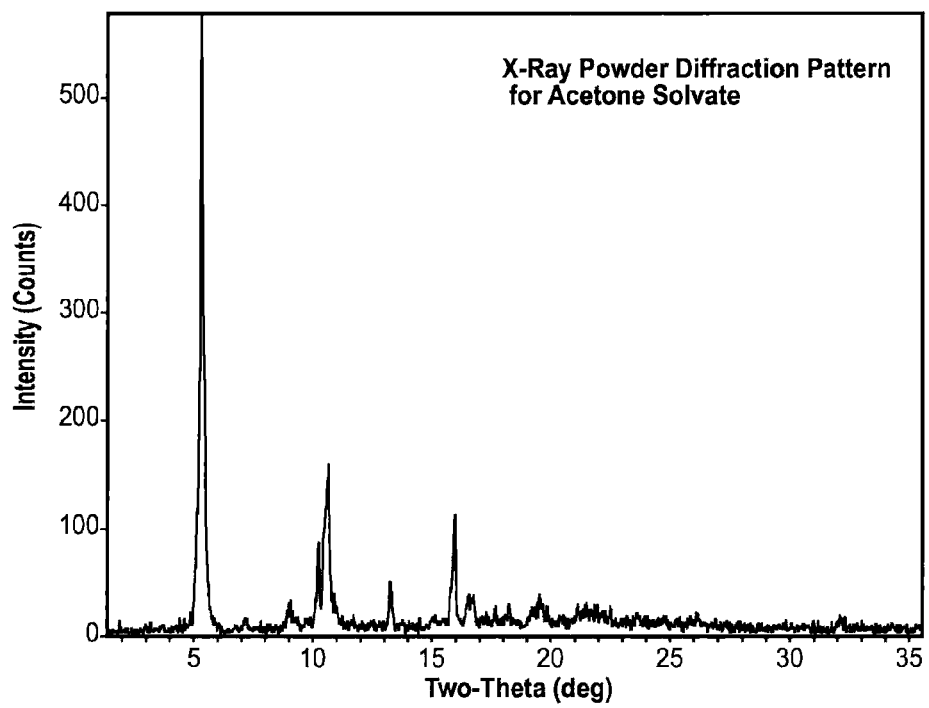
FIG. 2B is a graph illustrating a powder X-ray diffraction pattern of an embodiment of a crystalline form of a rapamycin analog acetone solvate.

In one embodiment, the crystalline rapamycin analog has a powder X-ray diffraction pattern with a peak at about 5.3, 10.2, 10.6, 13.3 and/or 16.0. Also, the powder X-ray diffraction pattern is substantially as shown in FIG. 2B.

Figure 3A:
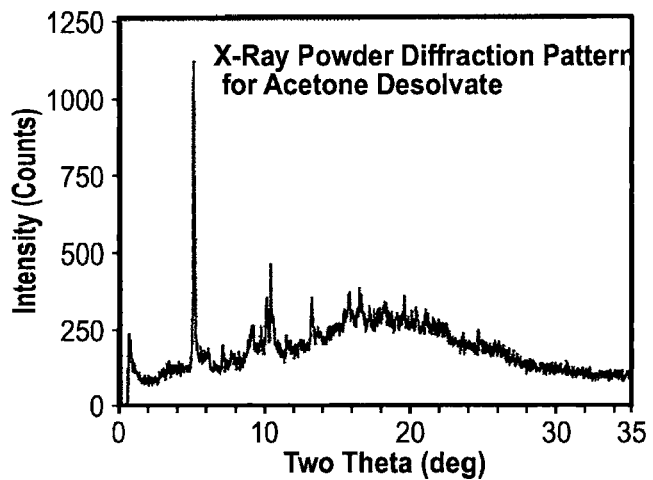
FIG. 3A is a graph illustrating a powder X-ray diffraction pattern of an embodiment of a crystalline form of a rapamycin analog acetone desolvate.

In one embodiment, the crystalline rapamycin analog has a powder X-ray diffraction pattern with a peak at about 5.3, 10.2, 10.5, and/or 13.3. Also, the powder X-ray diffraction pattern is substantially as shown in FIG. 3A.

Figure 3B:
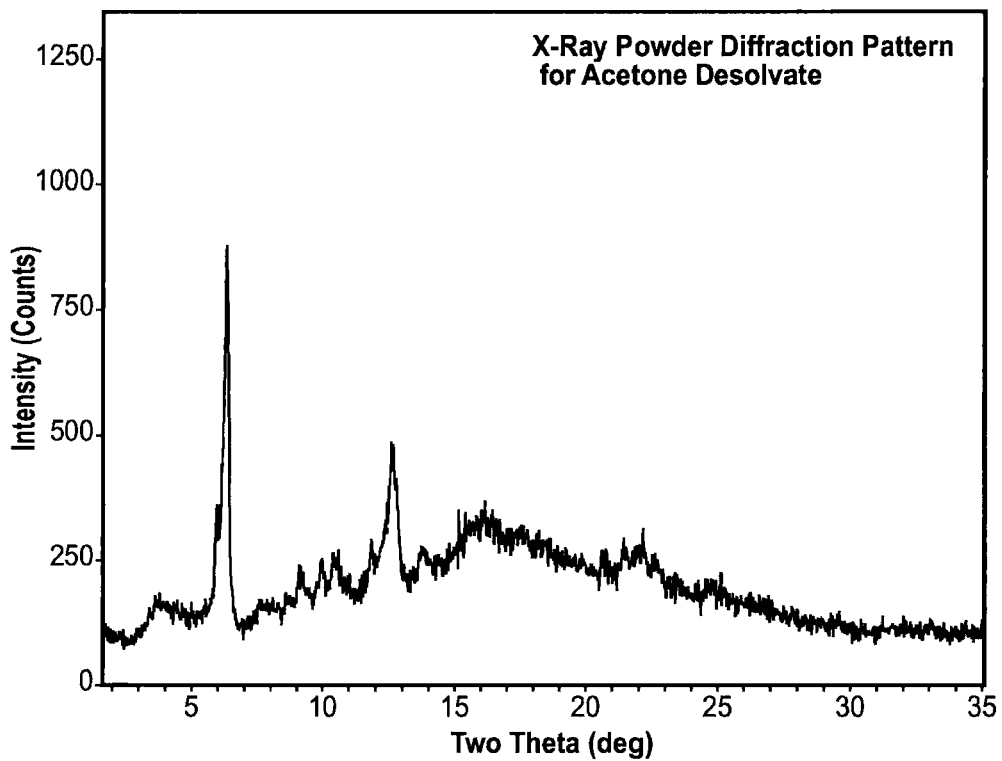
FIG. 3B is a graph illustrating a powder X-ray diffraction pattern of an embodiment of a crystalline form of a rapamycin analog acetone desolvate.

In one embodiment, the crystalline rapamycin analog has a powder X-ray diffraction pattern with a peak at about 6.3, and/or 12.6. Also, the powder X-ray diffraction pattern is substantially as shown in FIG. 3B.

Figure 4A:
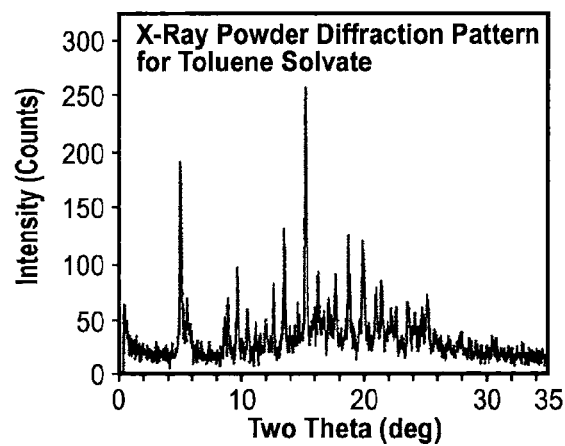
FIG. 4A is a graph illustrating a powder X-ray diffraction pattern of an embodiment of a crystalline form of a rapamycin analog toluene solvate.

In one embodiment, the crystalline rapamycin analog has a powder X-ray diffraction pattern with a peak at about 5.4, 5.9, 9.9, 13.8, and/or 15.5. Also, the powder X-ray diffraction pattern is substantially as shown in FIGS. 4A and/or 4B.

Figure 4B:
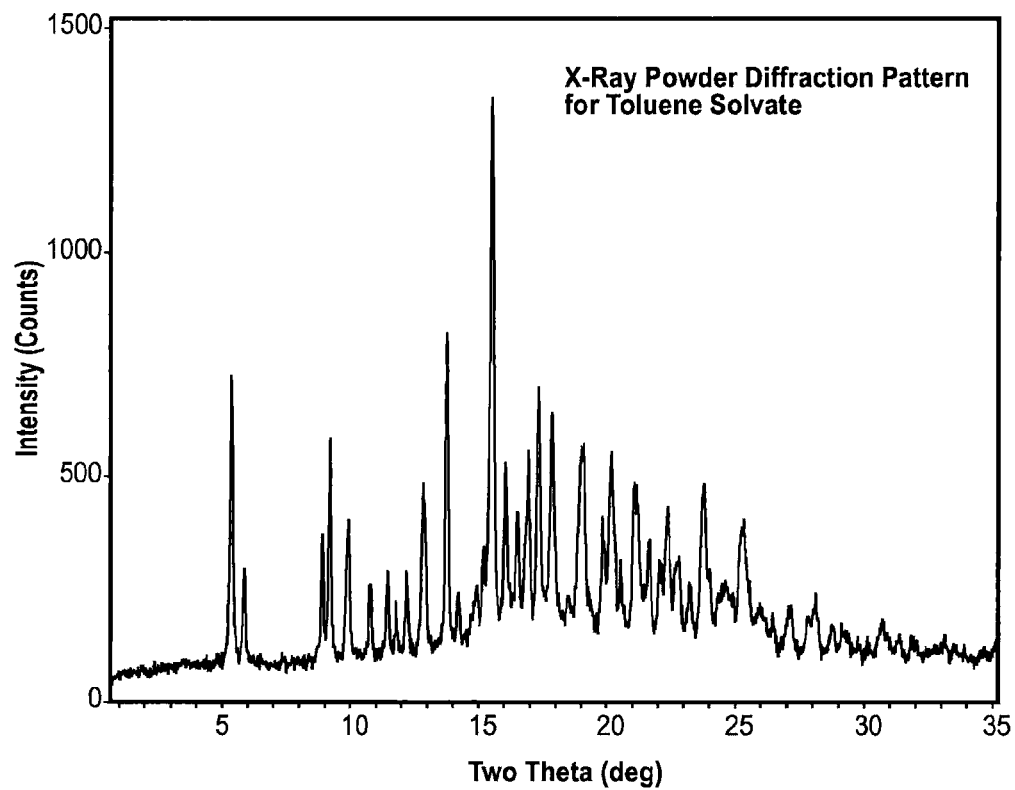
FIG. 4B is a graph illustrating a powder X-ray diffraction pattern of an embodiment of a crystalline form of a rapamycin analog toluene solvate.
Figure 4C:
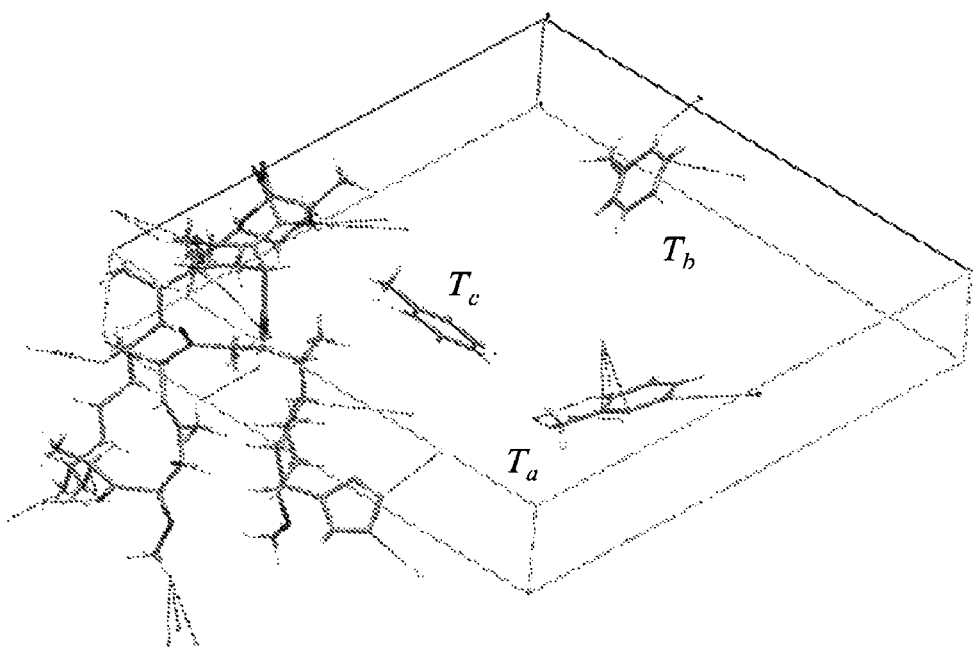
FIG. 4C is a schematic diagram of an embodiment of a single X-ray crystal structure for the rapamycin analog toluene solvate of FIG. 4B.
Figure 4D:
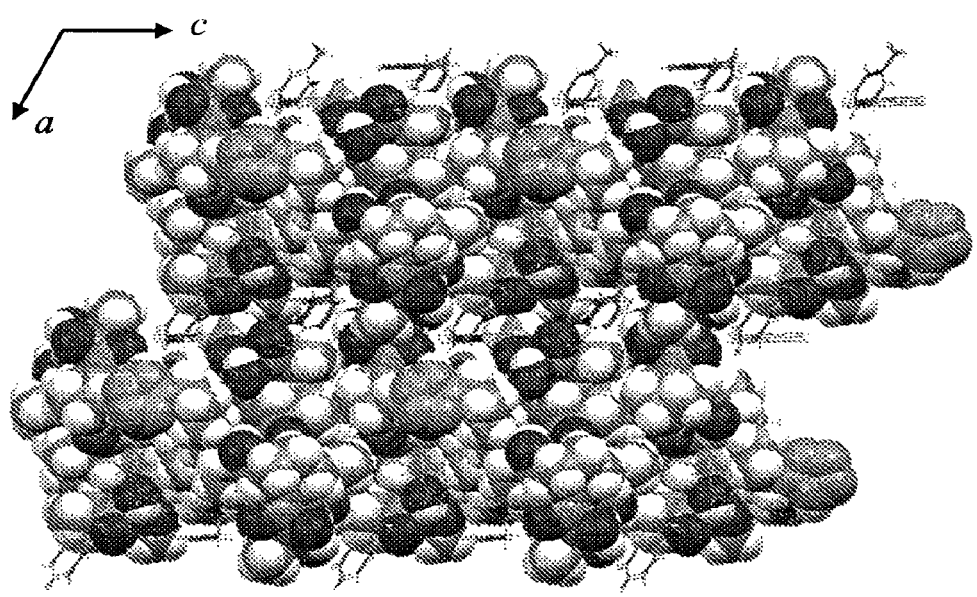
FIG. 4D is a schematic diagram of an embodiment of a crystal structure showing solvent channels along the "b" axis for the rapamycin analog toluene solvate of FIG. 4B
Figure 4E:
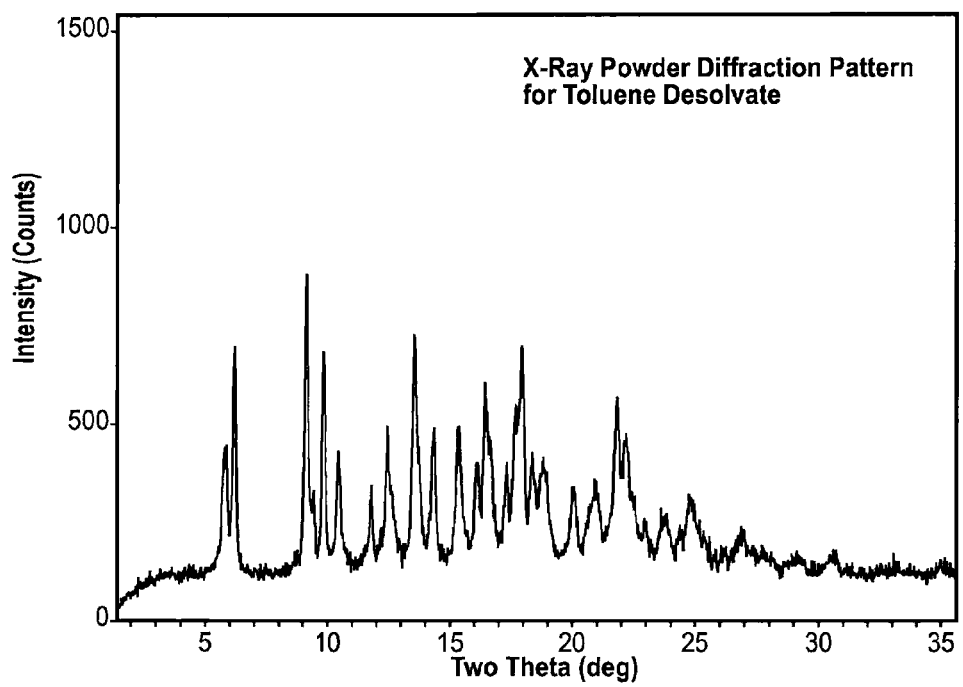
FIG. 4E is a graph illustrating a powder X-ray diffraction pattern of an embodiment of a crystalline form of a rapamycin analog toluene desolvate.

In one embodiment, the crystalline rapamycin analog has a powder X-ray diffraction pattern with a peak at about 5.9, 6.2, 9.1, 9.8, 12.5, 13.6, 16.4, 17.7, 17.9, and/or 21.8. Also, the powder X-ray diffraction pattern is substantially as shown in FIG. 4E.

Figure 5A:
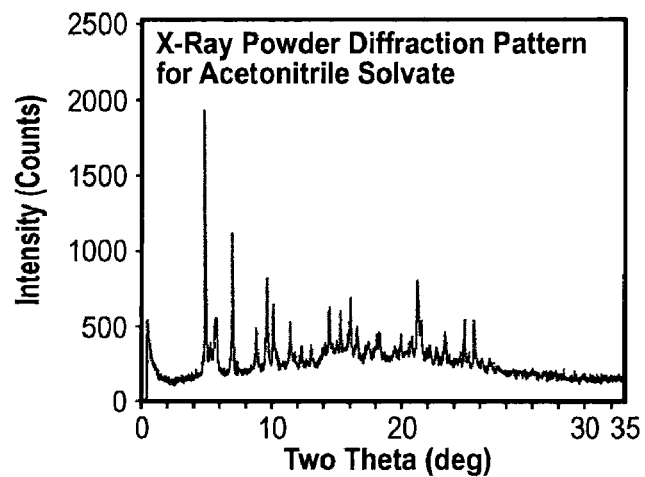
FIG. 5A is a graph illustrating a powder X-ray diffraction pattern of an embodiment of a crystalline form of a rapamycin analog acetonitrile solvate.

In one embodiment, the crystalline rapamycin analog has a powder X-ray diffraction pattern with a peak at about 5.2, 5.6, 6.0, 7.3, 10.0, and/or 21.5. Also, the powder X-ray diffraction pattern is substantially as shown in FIG. 5A.

Figure 5B:
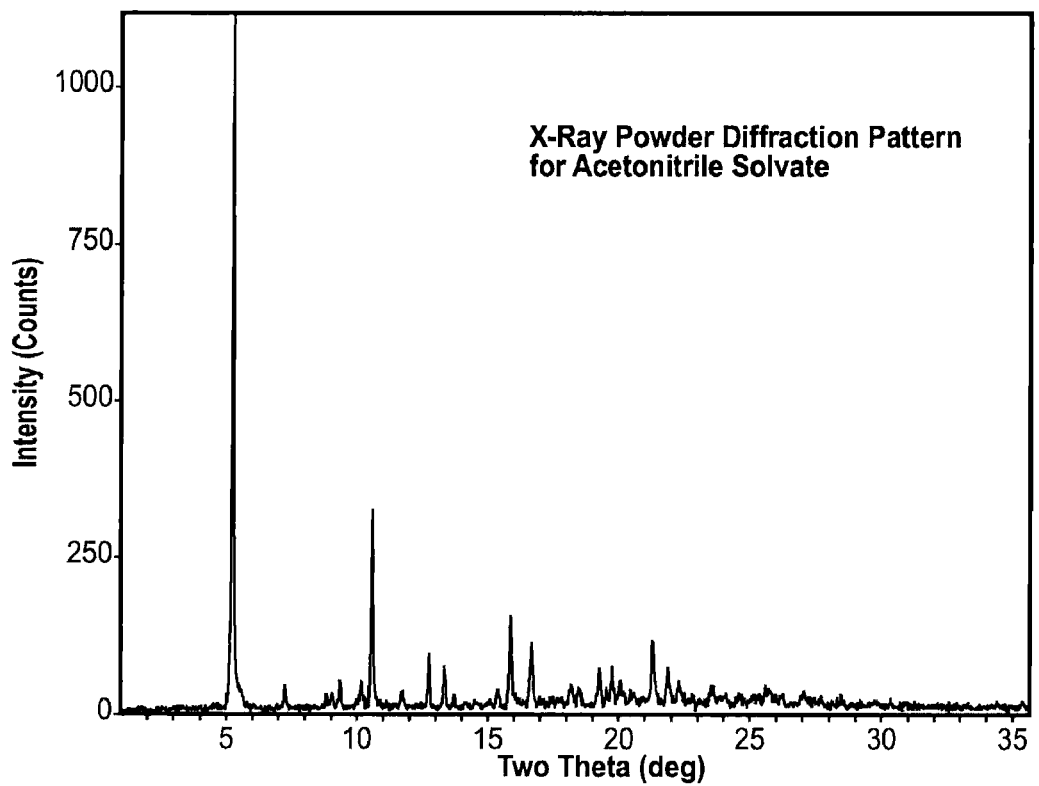
FIG. 5B is a graph illustrating a powder X-ray diffraction pattern of an embodiment of a crystalline form of a rapamycin analog acetonitrile solvate.

In one embodiment, the crystalline rapamycin analog has a powder X-ray diffraction pattern with a peak at about 5.3, 10.6, 12.8, 13.3, 15.9, 16.7, 21.3, and/or 21.9. Also, the powder X-ray diffraction pattern is substantially as shown in FIG. 5B.

Figure 6A:
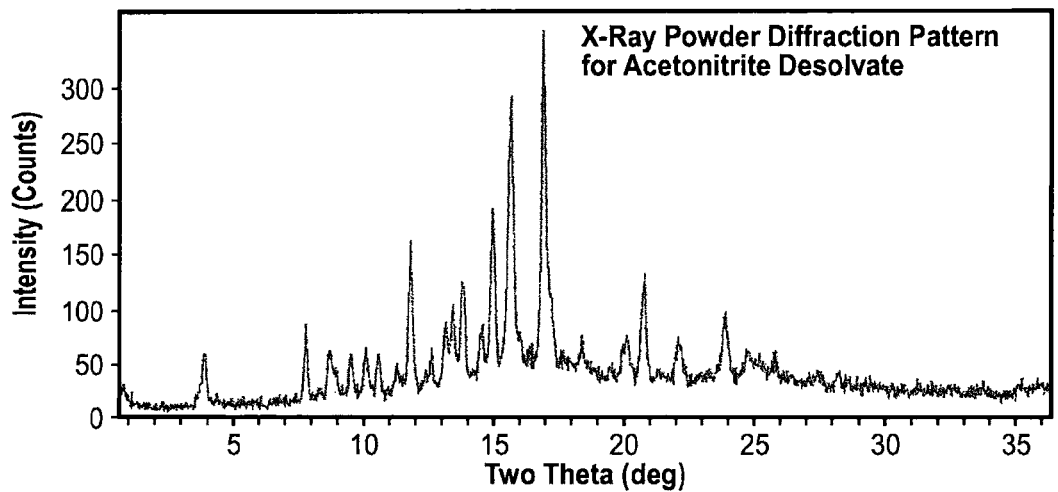
FIG. 6A is a graph illustrating a powder X-ray diffraction pattern of an embodiment of a crystalline form of a rapamycin analog acetonitrile desolvate.

In one embodiment, the crystalline rapamycin analog has a powder X-ray diffraction pattern with a peak at about 3.9, 8.7, 9.5, 13.8, 15.7, and/or 16.9. Also, the powder X-ray diffraction pattern is substantially as shown in FIG. 6A.

Figure 6B:
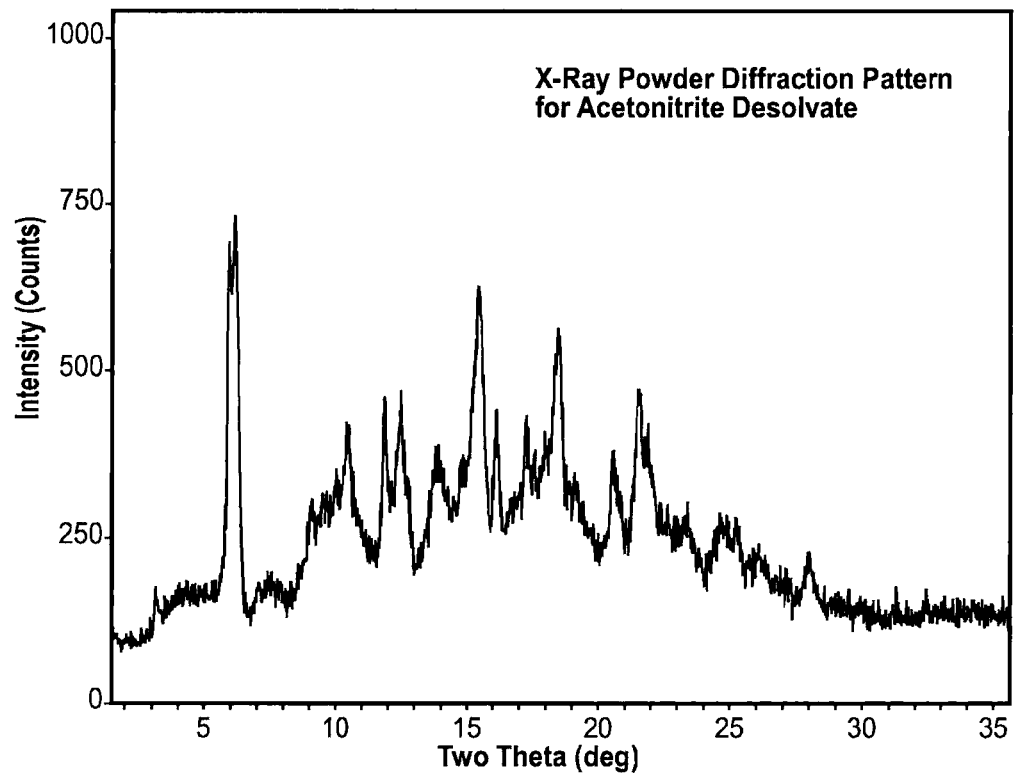
FIG. 6B is a graph illustrating a powder X-ray diffraction pattern of an embodiment of a crystalline form of a rapamycin analog acetonitrile desolvate.

In one embodiment, the crystalline rapamycin analog has a powder X-ray diffraction pattern with a peak at about 6.2, 10.4, 11.9, 12.5, 15.4, 18.5, and/or 21.5. Also, the powder X-ray diffraction pattern is substantially as shown in FIG. 6B.

Figure 7A:
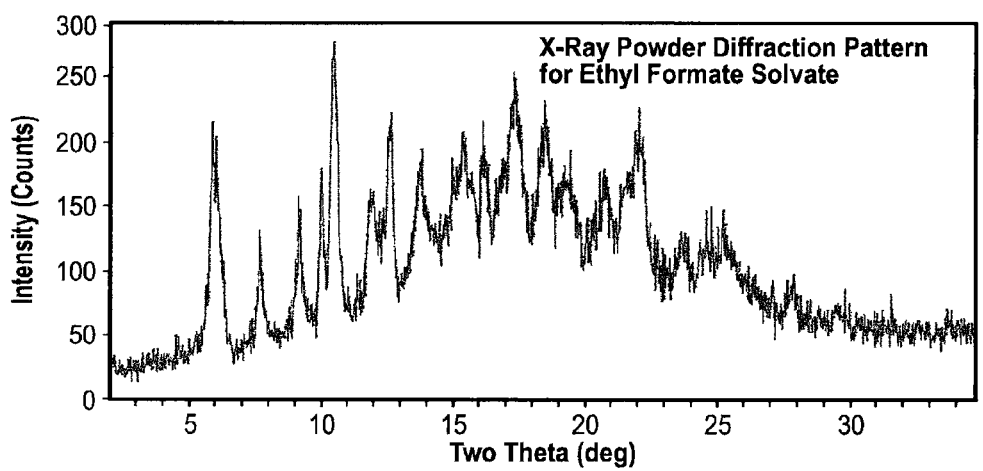
FIG. 7A is a graph illustrating a powder X-ray diffraction pattern of an embodiment of a crystalline form of a rapamycin analog ethyl formate solvate.

In one embodiment, the crystalline rapamycin analog has a powder X-ray diffraction pattern with a peak at about 5.9, 7.7, 9.1, 10.0, and/or 10.5. Also, the powder X-ray diffraction pattern is substantially as shown in FIG. 7A.

Figure 7B:
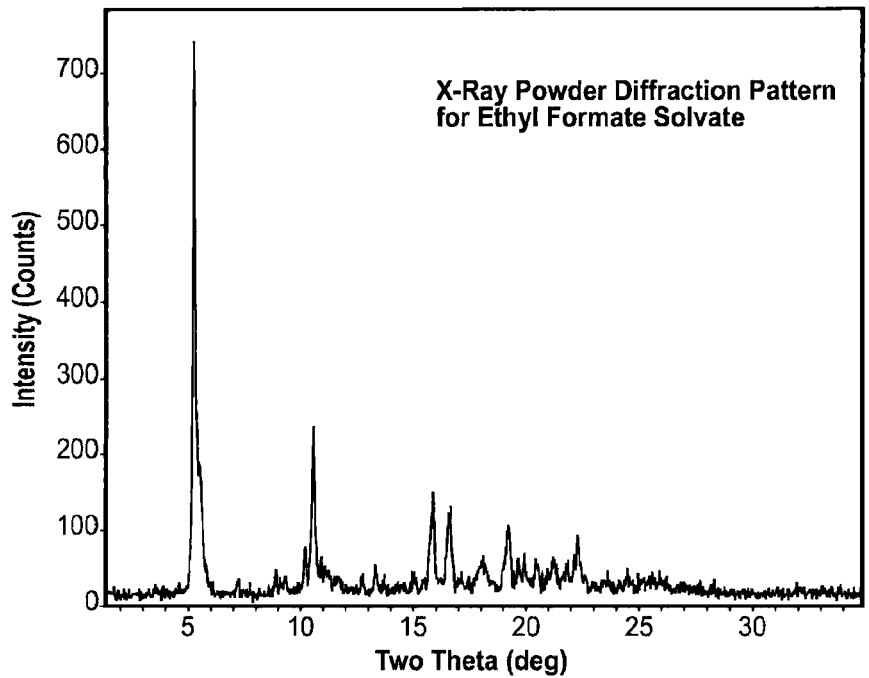
FIG. 7B is a graph illustrating a powder X-ray diffraction pattern of an embodiment of a crystalline form of a rapamycin analog ethyl formate solvate.

In one embodiment, the crystalline rapamycin analog has a powder X-ray diffraction pattern with a peak at about 5.3, 5.5, 10.6, 15.9, 16.5, and/or 19.2. Also, the powder X-ray diffraction pattern is substantially as shown in FIG. 7B.

Figure 8:
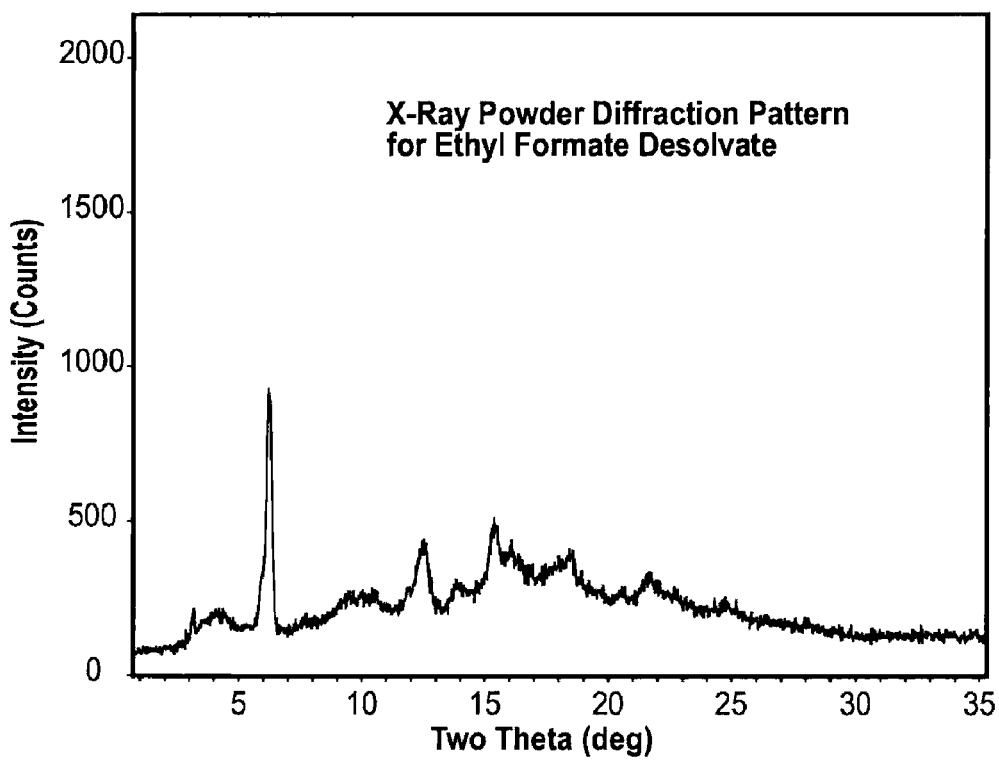
FIG. 8 is a graph illustrating a powder X-ray diffraction pattern of an embodiment of a crystalline form of a rapamycin analog ethyl formate desolvate.

In one embodiment. the crystalline rapamycin analog has a powder X-ray diffraction pattern with a peak at about 6.2, 12.5, and/or 15.4. Also, the powder X-ray diffraction pattern is substantially as shown in FIG. 8.

Figure 9A:
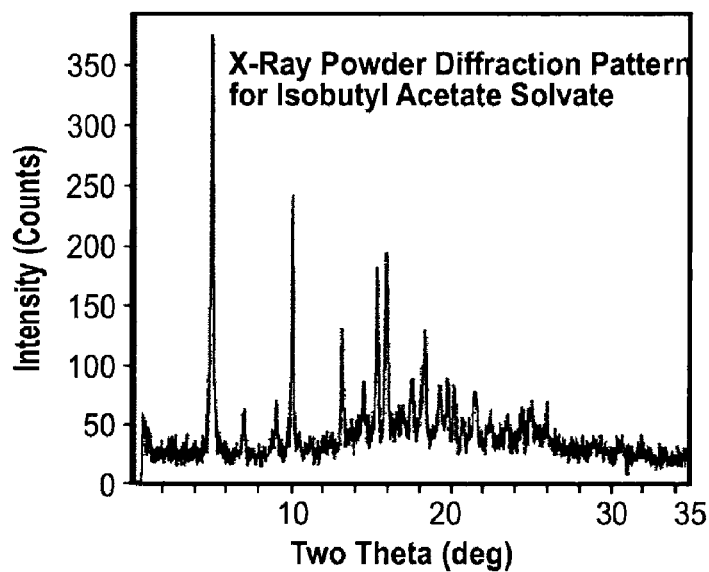
FIG. 9A is a graph illustrating a powder X-ray diffraction pattern of an embodiment of a crystalline form of a rapamycin analog isobutyl acetate solvate.

In one embodiment, the crystalline rapamycin analog has a powder X-ray diffraction pattern with a peak at about 5.0, 7.0, 9.1, 10.1, 15.4, and 16.0. Also, the powder X-ray diffraction pattern is substantially as shown in FIGS. 9A and/or 9B.

Figure 10A:
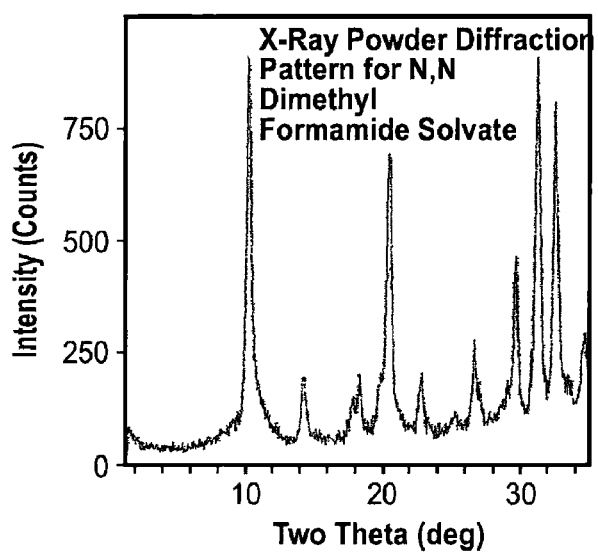
FIG. 10A is a graph illustrating a powder X-ray diffraction pattern of an embodiment of a crystalline form of a rapamycin analog N,N-dimethyl formamide solvate.

In one embodiment, the crystalline rapamycin analog has a powder X-ray diffraction pattern with a peak at about 5.1, 7.2, 9.0, 9.2, 10.3, 11.5, 15.7, and 16.3. Also, the powder X-ray diffraction pattern is substantially as shown in FIGS. 10A and/or 10B.

Figure 11A:
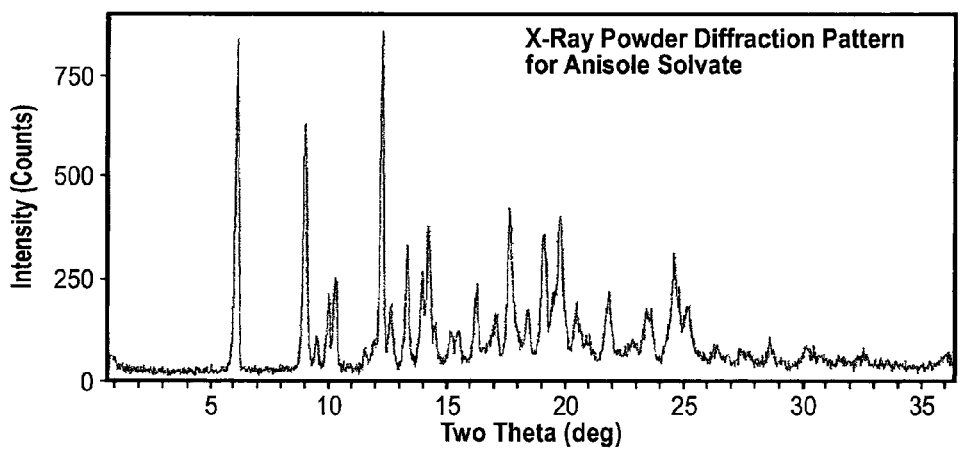
FIG. 11A is a graph illustrating a powder X-ray diffraction pattern of an embodiment of a crystalline form of a rapamycin analog anisole solvate.

In one embodiment, the crystalline rapamycin analog has a powder X-ray diffraction pattern with a peak at about 6.1, 8.9, 9.4, 10.0, 10.2, and 12.2. Also, the powder X-ray diffraction pattern is substantially as shown in FIGS. 11A and/or 11B.

Figure 12A:
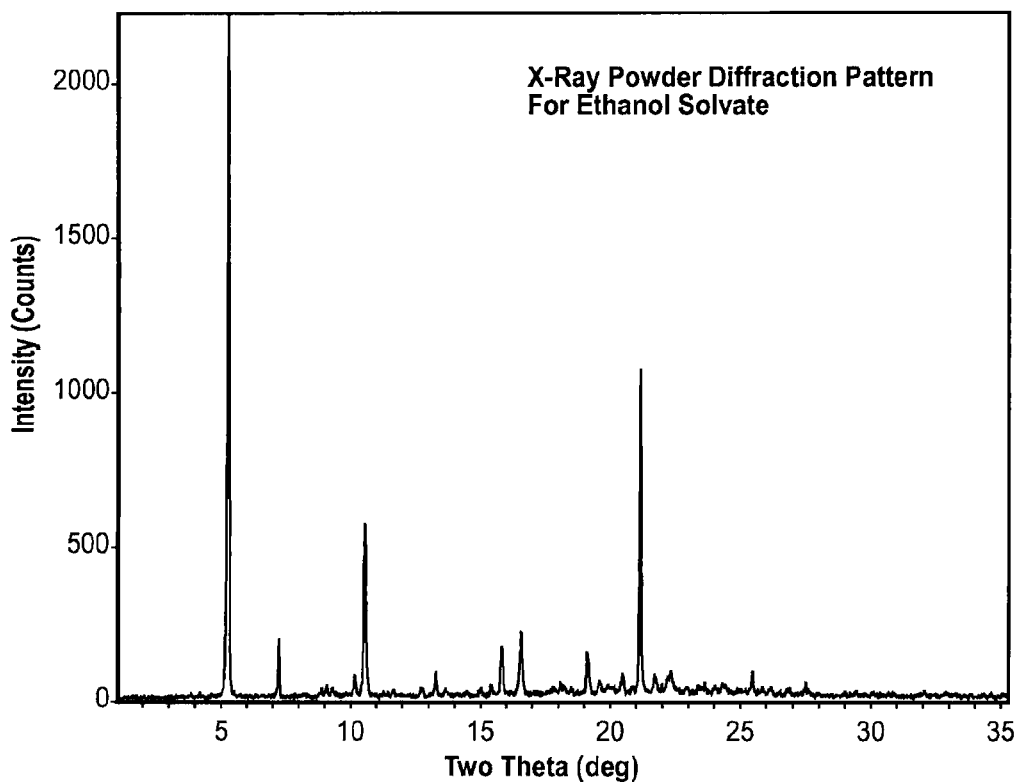
FIG. 12A is a graph illustrating a powder X-ray diffraction pattern of an embodiment of a crystalline form of a rapamycin analog ethanol solvate.

In one embodiment, the crystalline rapamycin analog has a powder X-ray diffraction pattern with a peak at about 5.3, 7.2, 10.5, 15.8, 16.6, 19.1, and/or 21.2. Also, the powder X-ray diffraction pattern is substantially as shown in FIG. 12A.

Figure 12B:
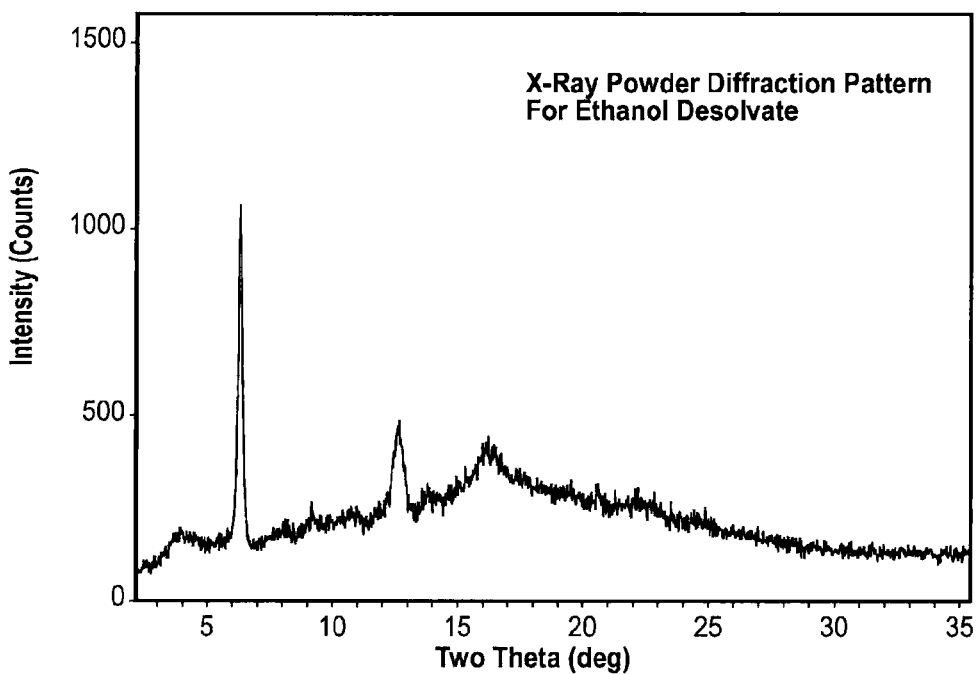
FIG. 12B is a graph illustrating a powder X-ray diffraction pattern of an embodiment of a crystalline form of a rapamycin analog ethanol desolvate.

In one embodiment, the crystalline rapamycin analog has a powder X-ray diffraction pattern with a peak at about 6.3, 9.2, 12.7, 13.8, and/or 16.1. Also, the powder X-ray diffraction pattern is substantially as shown in FIG. 12B.

Figure 13A:
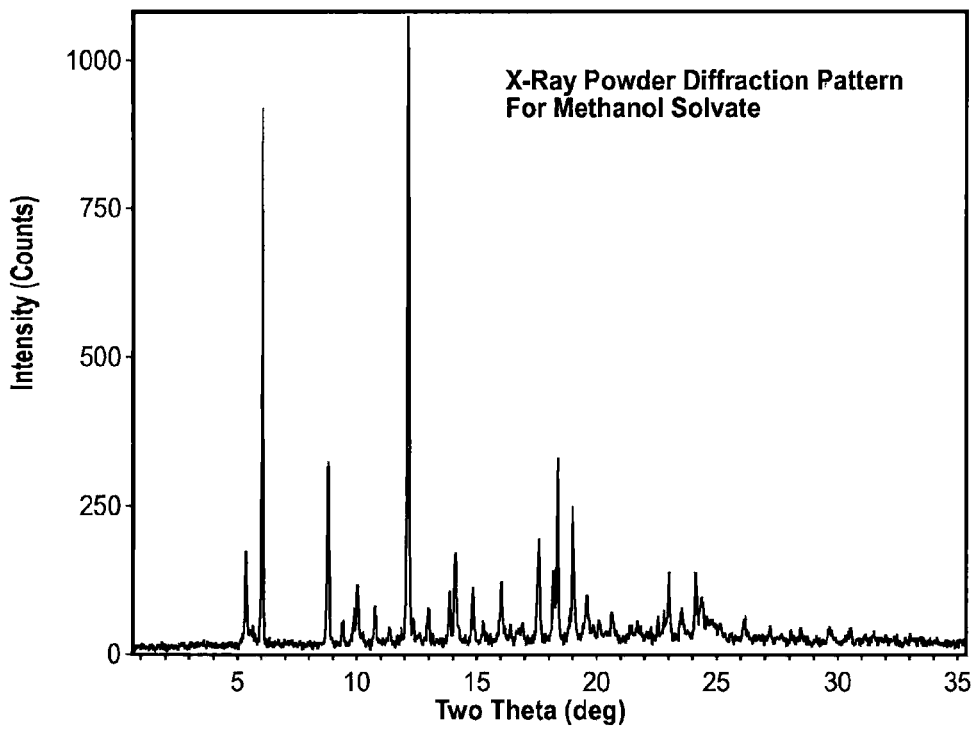
FIG. 13A is a graph illustrating a powder X-ray diffraction pattern of an embodiment of a crystalline form of a rapamycin analog methanol solvate

In one embodiment, the crystalline rapamycin analog has a powder X-ray diffraction pattern with a peak at about 5.4, 6.0, 8.8, 10.0, 12.1, 14.1, 17.6, 18.4, and/or 19.0. Also, the powder X-ray diffraction pattern is substantially as shown in FIG. 13A.

Figure 13B:
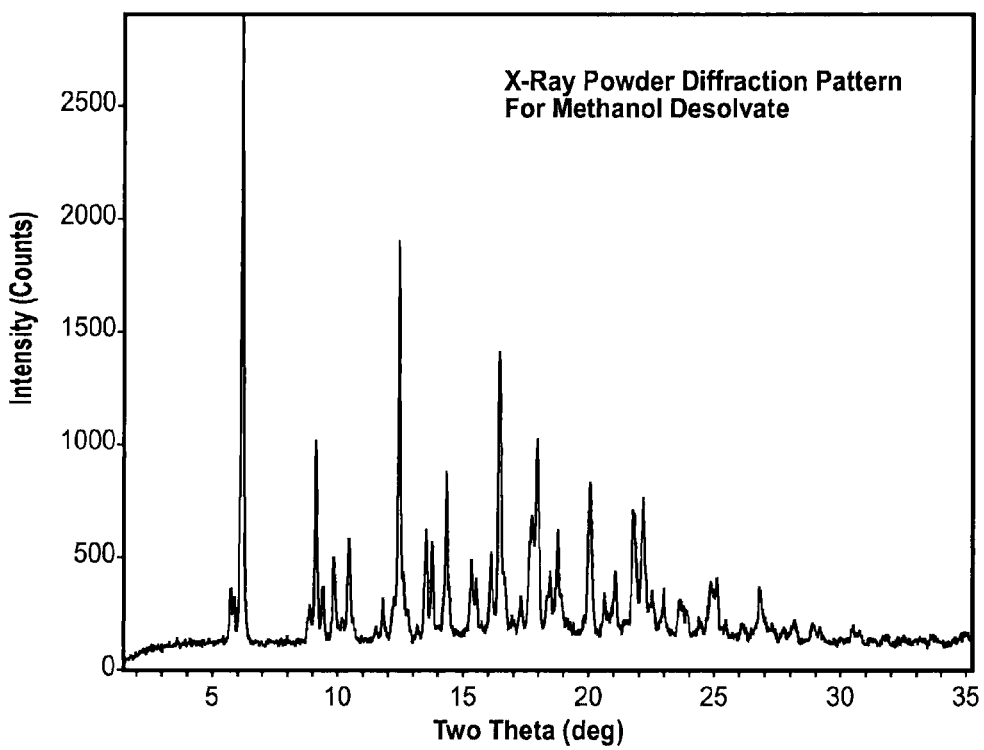
FIG. 13B is a graph illustrating a powder X-ray diffraction pattern of an embodiment of a crystalline form of a rapamycin analog methanol desolvate.

In one embodiment. the crystalline rapamycin analog has a powder X-ray diffraction pattern with a peak at about 6.2, 9.1, 10.5, 12.5, 14.3, 16.5, 18.0, 20.1, 21.8, and/or 22.2. Also, the powder X-ray diffraction pattern is substantially as shown in FIG. 13B.

Figure 16:
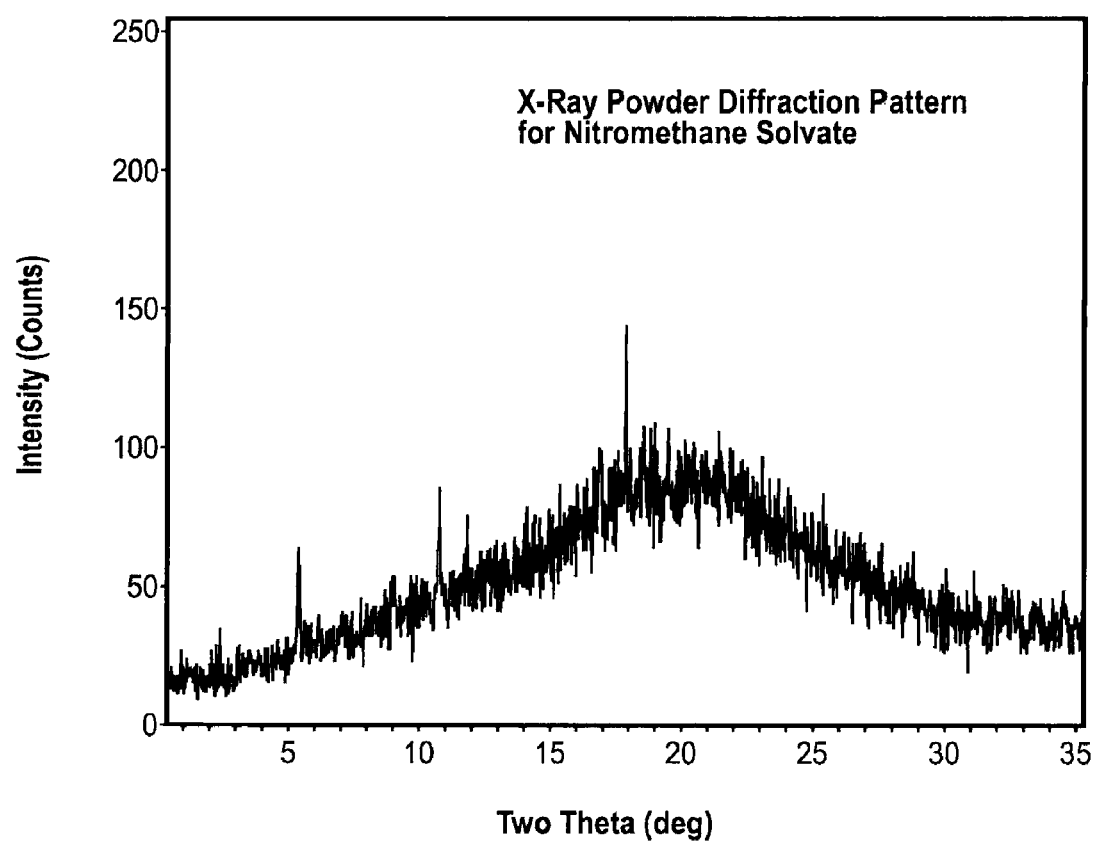
FIG. 16 is a graph illustrating a powder X-ray diffraction pattern of an embodiment of a crystalline form of a rapamycin analog nitromethane solvate.

In one embodiment, the crystalline rapamycin analog has a powder X-ray diffraction pattern with a peak at about 5.4, 10.8, 11.8, 16.9, and/or 17.9. Also, the powder X-ray diffraction pattern is substantially as shown in FIG. 16.

Figure 18A:
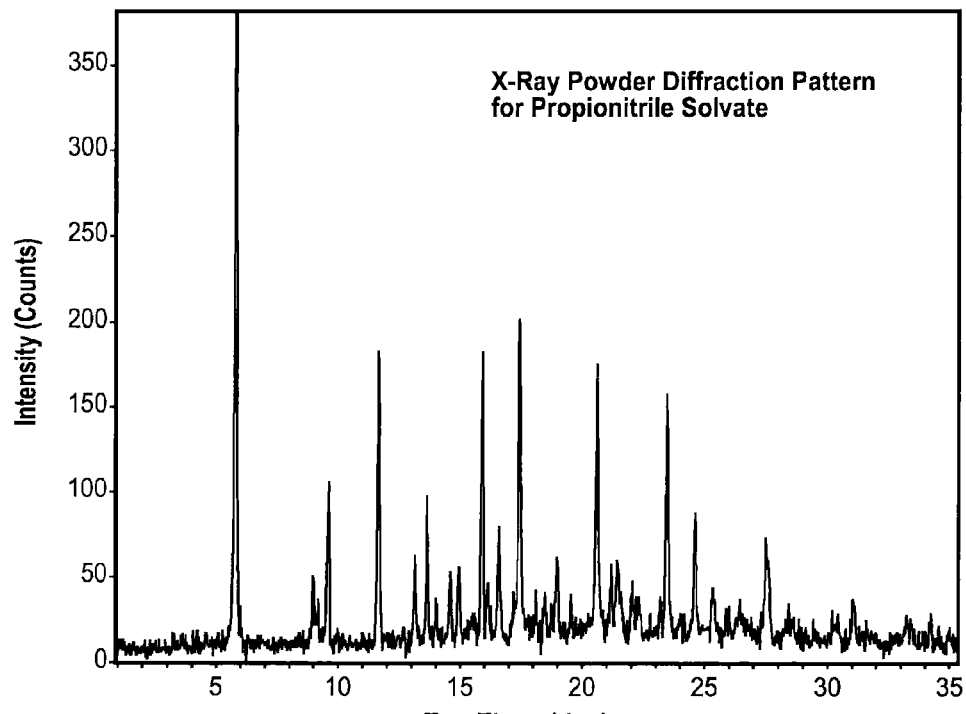
FIG. 18A is a graph illustrating a powder X-ray diffraction pattern of an embodiment of a crystalline form of a rapamycin analog propionitrile solvate.

In one embodiment, the crystalline rapamycin analog has a powder X-ray diffraction pattern with a peak at about 5.8, 9.6, 11.7, 13.6, 15.9, 17.4, 20.6, and/or 23.5. Also, the powder X-ray diffraction pattern is substantially as shown in FIG. 18A.

Figure 18B:
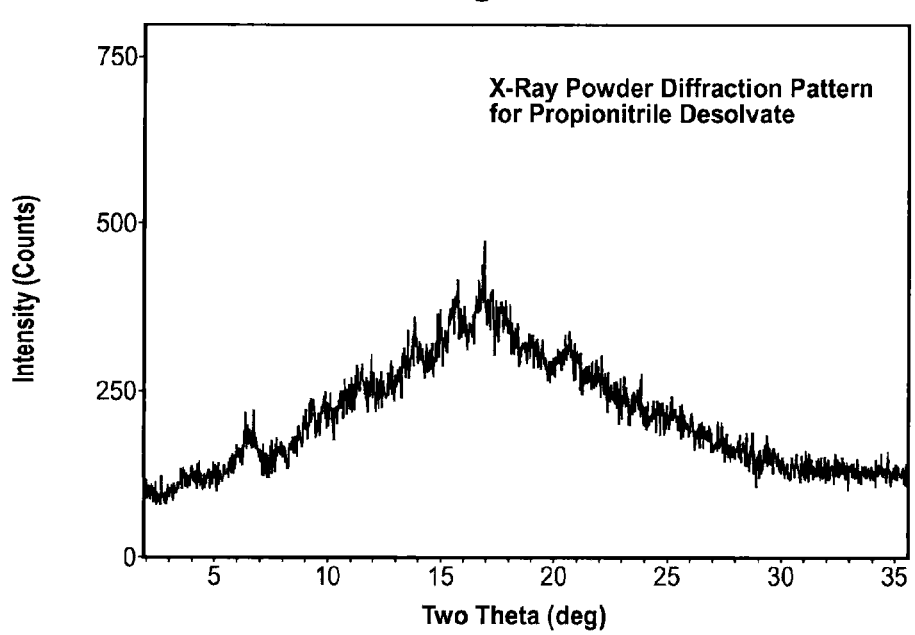
FIG. 18B is a graph illustrating a powder X-ray diffraction pattern of an embodiment of a crystalline form of a rapamycin analog propionitrile desolvate.

In one embodiment, the crystalline rapamycin analog has a powder X-ray diffraction pattern with a peak at about 6.4, 6.8, 9.3, 13.8, and/or 16.8. Also, the powder X-ray diffraction pattern is substantially as shown in FIG. 18B.

Figure 14A:
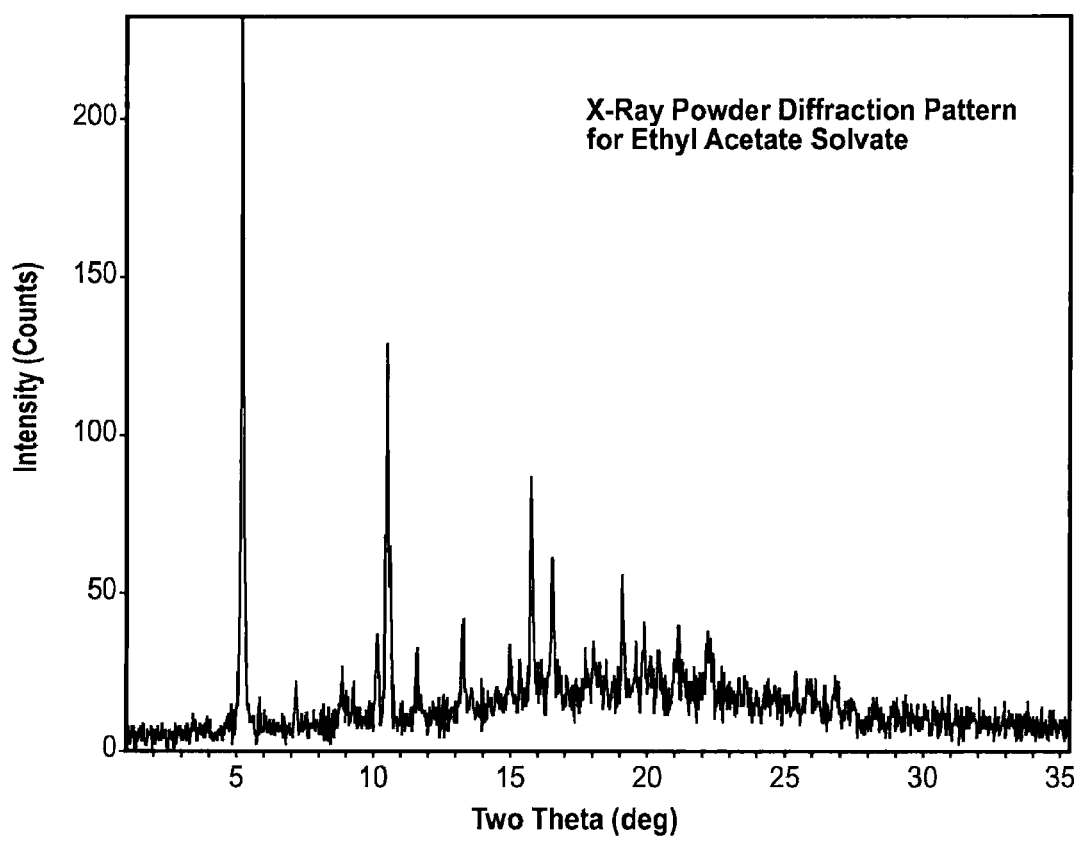
FIG. 14A is a graph illustrating a powder X-ray diffraction pattern of an embodiment of a crystalline form of a rapamycin analog ethyl acetate solvate.

In one embodiment, the crystalline rapamycin analog has a powder X-ray diffraction pattern with a peak at about 5.2, 10.5, 13.3, 15.8, 16.5, and/or 19.1. Also, the powder X-ray diffraction pattern is substantially as shown in FIG. 14A.

Figure 14B:
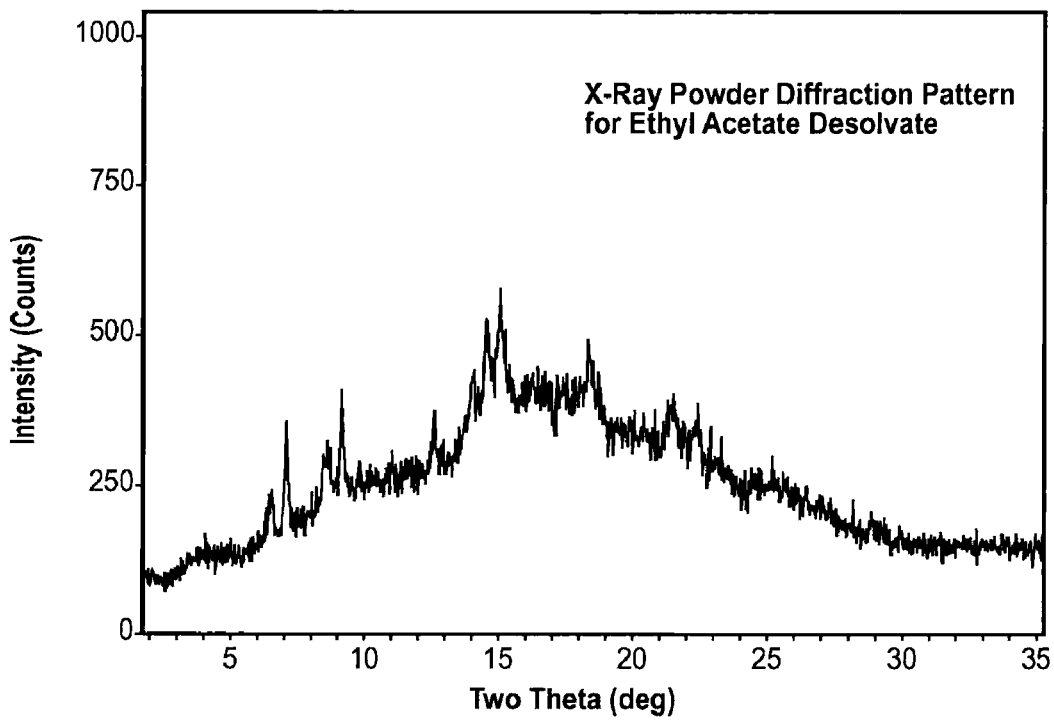
FIG. 14B is a graph illustrating a powder X-ray diffraction pattern of an embodiment of a crystalline form of a rapamycin analog ethyl acetate desolvate.

In one embodiment, the crystalline rapamycin analog has a powder X-ray diffraction pattern with a peak at about 6.6, 7.1, 8.6, 9.1, 12.6, 14.5, and/or 15.0. Also, the powder X-ray diffraction pattern is substantially as shown in FIG. 14B.

Figure 17A:
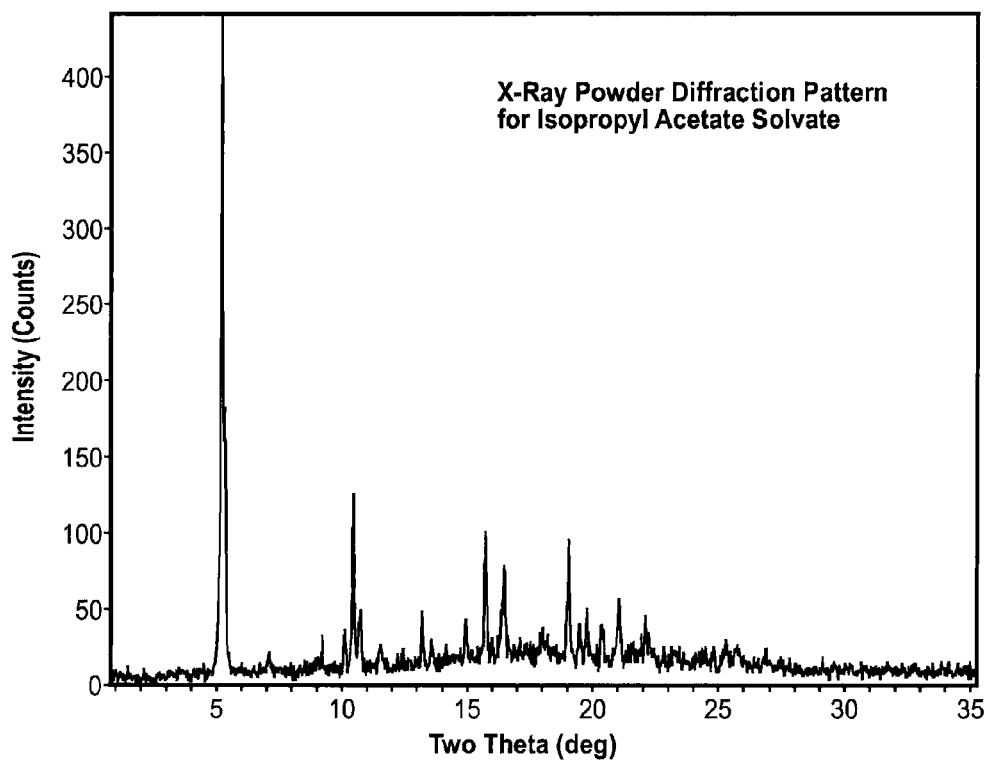
FIG. 17A is a graph illustrating a powder X-ray diffraction pattern of an embodiment of a crystalline form of a rapamycin analog isopropyl acetate solvate.

In one embodiment, the crystalline rapamycin analog has a powder X-ray diffraction pattern with a peak at about 5.2, 10.5, 10.8, 15.7, 16.5, and/or 19.0. Also, the powder X-ray diffraction pattern is substantially as shown in FIG. 17A.

Figure 17B:
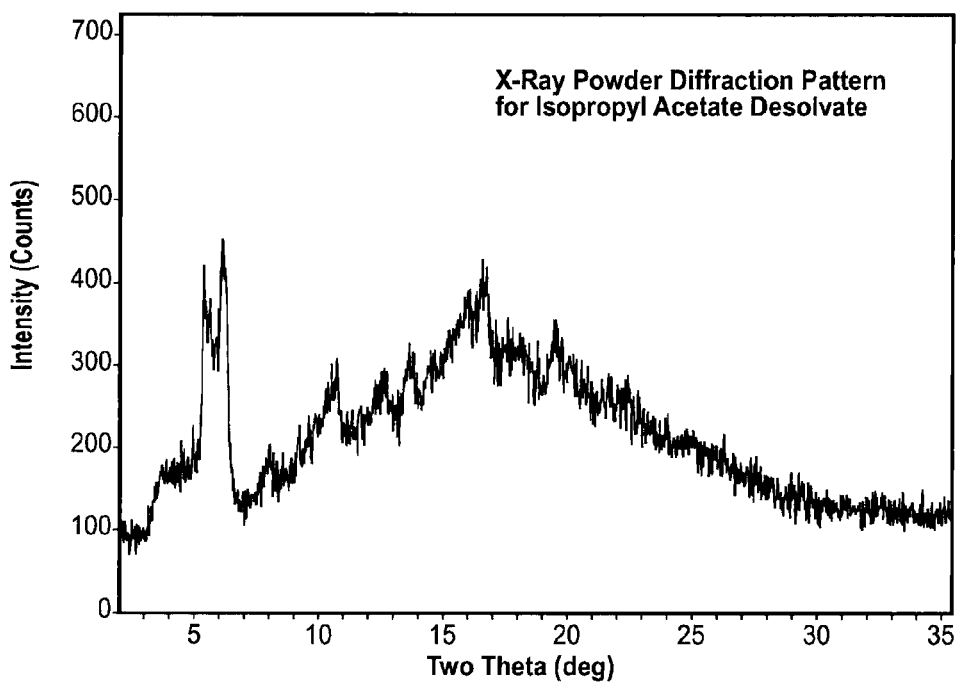
FIG. 17B is a graph illustrating a powder X-ray diffraction pattern of an embodiment of a crystalline form of a rapamycin analog isopropyl acetate desolvate.
Figure 19A:
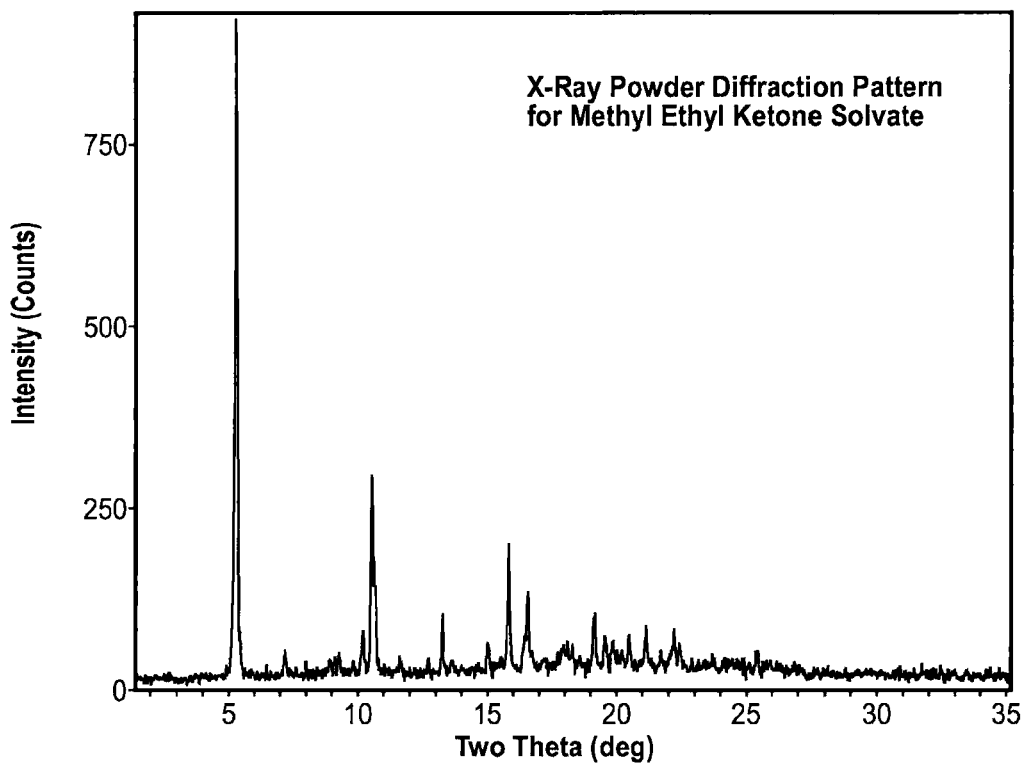
FIG. 19A is a graph illustrating a powder X-ray diffraction pattern of an embodiment of a crystalline form of a rapamycin analog methyl ethyl ketone solvate.

In one embodiment, the crystalline rapamycin analog has a powder X-ray diffraction pattern with a peak at about 5.5, 6.1, 8.0, 10.5, 12.6, 13.6, 16.6, and/or 19.5. Also, the powder X-ray diffraction pattern is substantially as shown in FIG. 17B, In one embodiment, the crystalline rapamycin analog has a powder X-ray diffraction pattern with a peak at about 5.3, 10.5, 13.3, 15.8, and/or 16.6. Also, the powder X-ray diffraction pattern is substantially as shown in FIG. 19A.

Figure 19B:
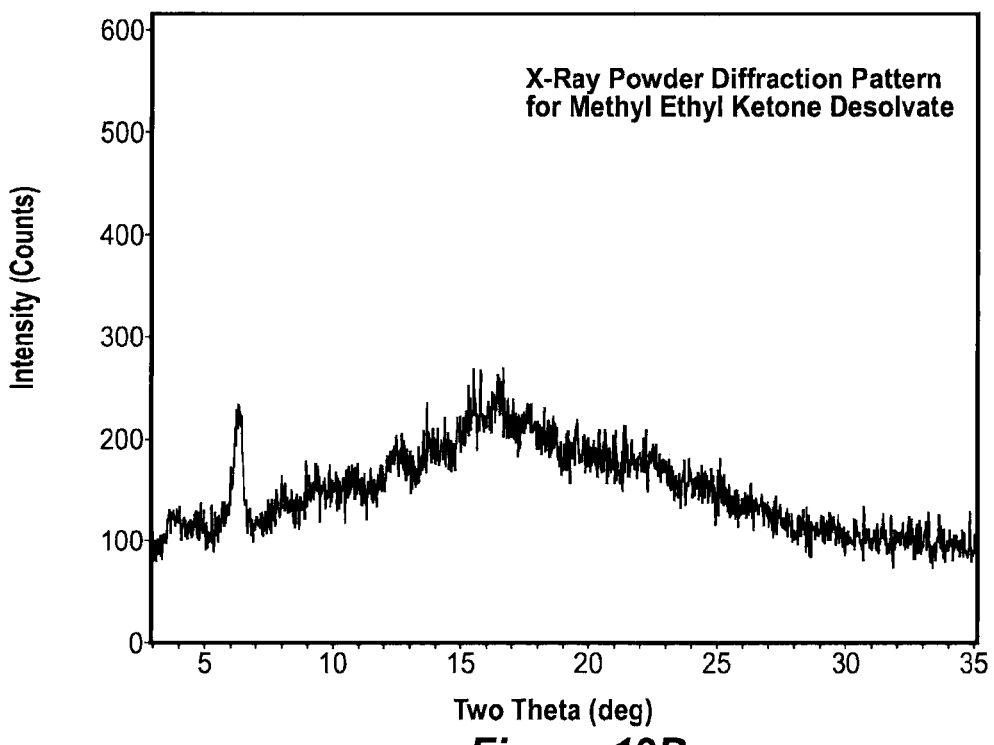
FIG. 19B is a graph illustrating a powder X-ray diffraction pattern of an embodiment of a crystalline form of a rapamycin analog methyl ethyl ketone desolvate.

In one embodiment, the crystalline rapamycin analog has a powder X-ray diffraction pattern with a peak at about 6.3, 8.1, 12.7 and/or 16.5. Also, the powder X-ray diffraction pattern is substantially as shown in FIG. 19B.

Figure 15A:
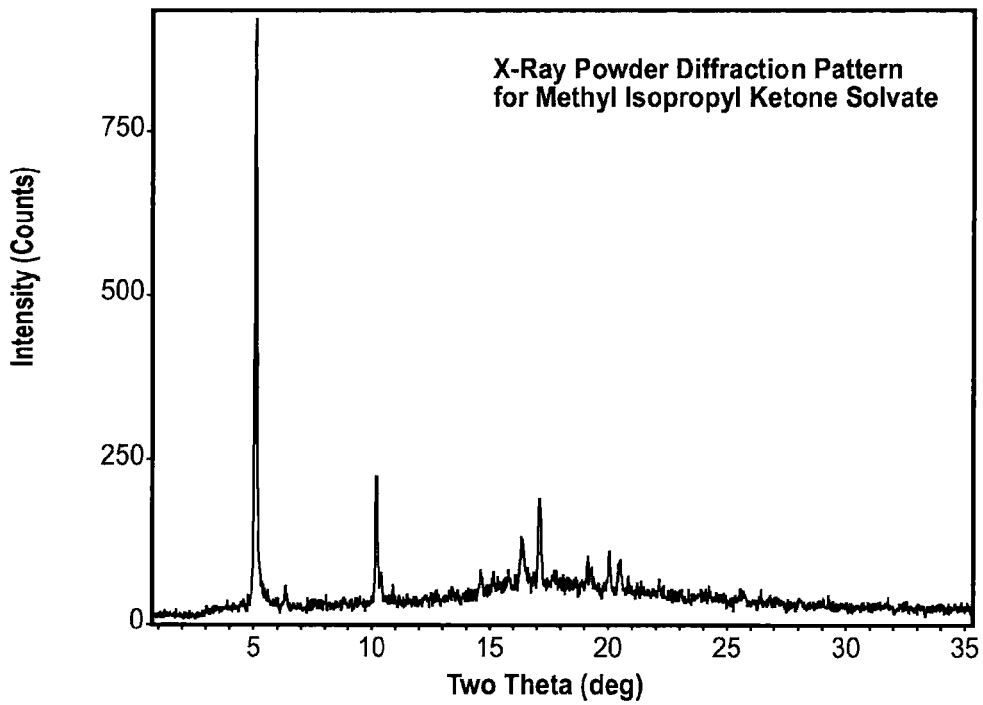
FIG. 15A is a graph illustrating a powder X-ray diffraction pattern of an embodiment of a crystalline form of a rapamycin analog methyl isopropyl ketone solvate.

In one embodiment, the crystalline rapamycin analog has a powder X-ray diffraction pattern with a peak at about 5.1, 10.2, 16.3, 17.1, 19.2, 20.1, and/or 20.5. Also, the powder X-ray diffraction pattern is substantially as shown in FIG. 15A.

Figure 15B:
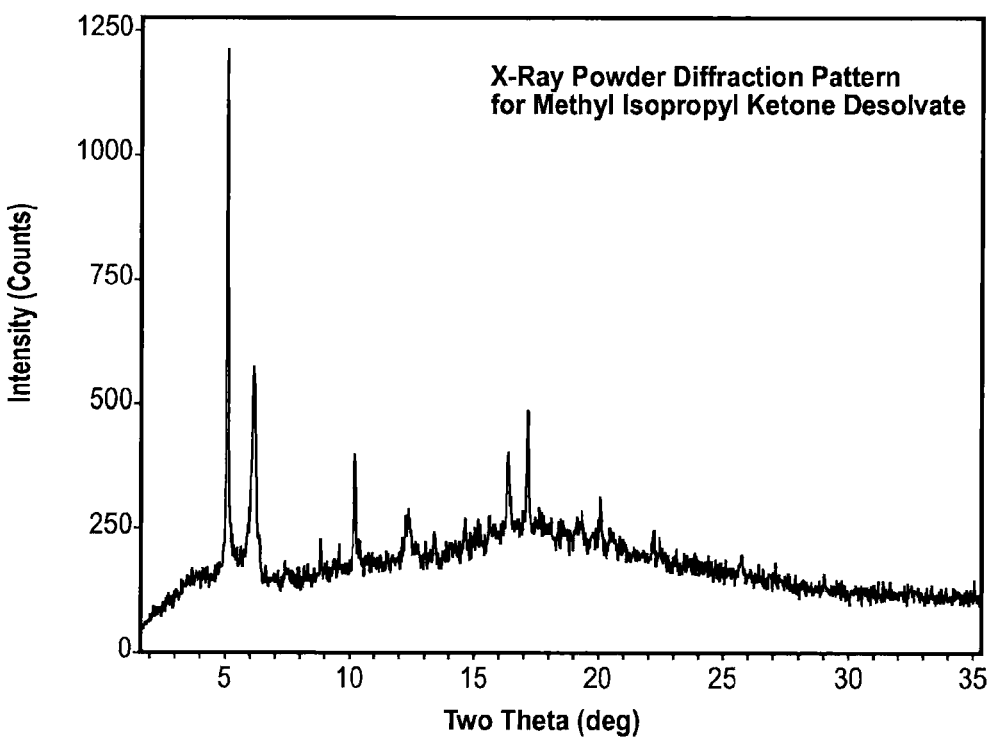
FIG. 15B a graph illustrating a powder X-ray diffraction pattern of an embodiment of a crystalline form of a rapamycin analog methyl isopropyl ketone desolvate.

In one embodiment, the crystalline rapamycin analog has a powder X-ray diffraction pattern with a peak at about 5.1, 6.2, 10.2, 12.4, 16.4, and/or 17.2. Also, the powder X-ray diffraction pattern is substantially as shown in FIG. 15B.

Figure 20A:
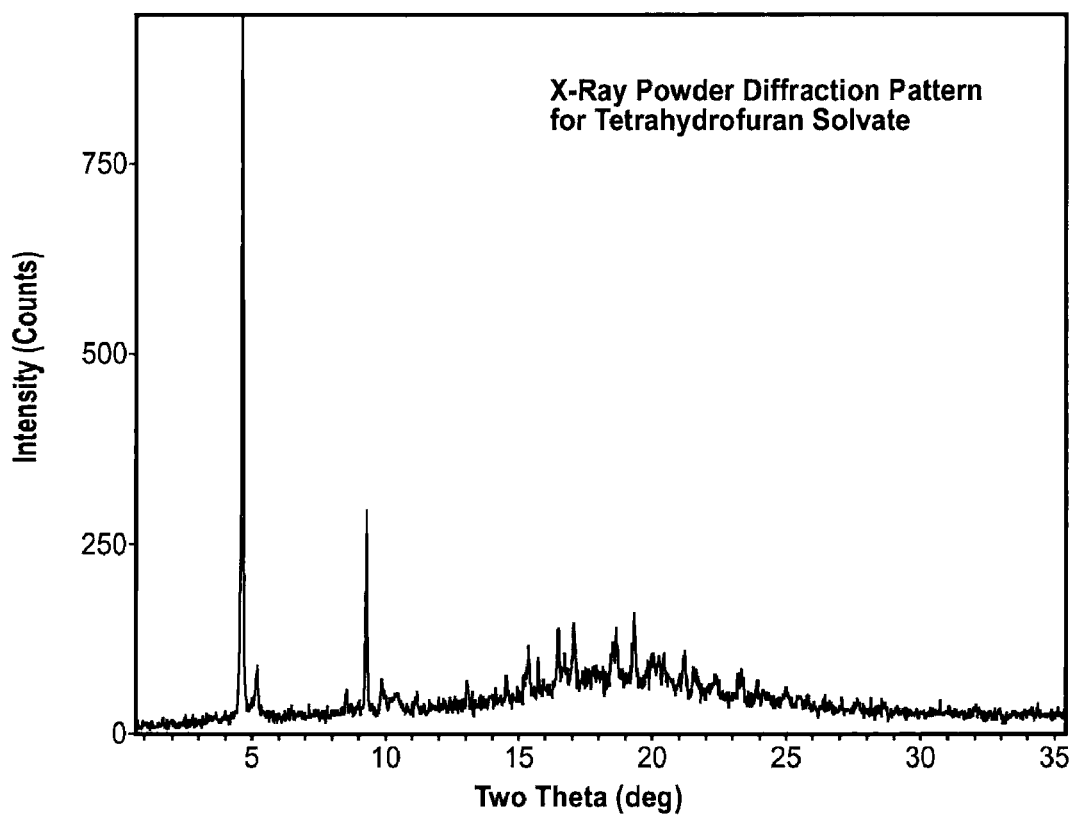
FIG. 20A is a graph illustrating a powder X-ray diffraction pattern of an embodiment of a crystalline form of a rapamycin analog tetrahydrofuran solvate.

In one embodiment, the crystalline rapamycin analog has a powder X-ray diffraction pattern with a peak at about 4.6, 5.2, 9.3, 16.5, 17.0, and/or 18.6. Also, the powder X-ray diffraction pattern is substantially as shown in FIG. 20A.

Figure 20B:
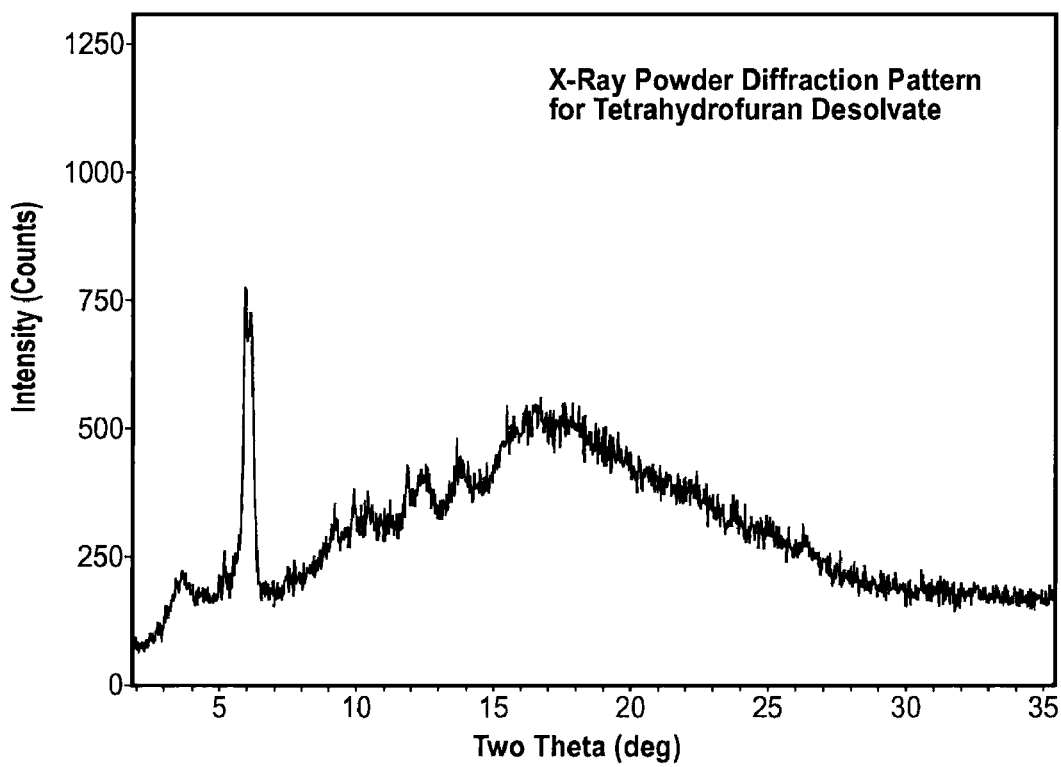
FIG. 20B is a graph illustrating a powder X-ray diffraction pattern of an embodiment of a crystalline form of a rapamycin analog tetrahydrofuran desolvate.

In one embodiment, the crystalline rapamycin analog has a powder X-ray diffraction pattern with a peak at about 3.8, 6.0, 9.2, 9.9, 11.8, 12.4, and/or 13.7. Also, the powder X-ray diffraction pattern is substantially as shown in FIG. 20B.

Figure 21A:
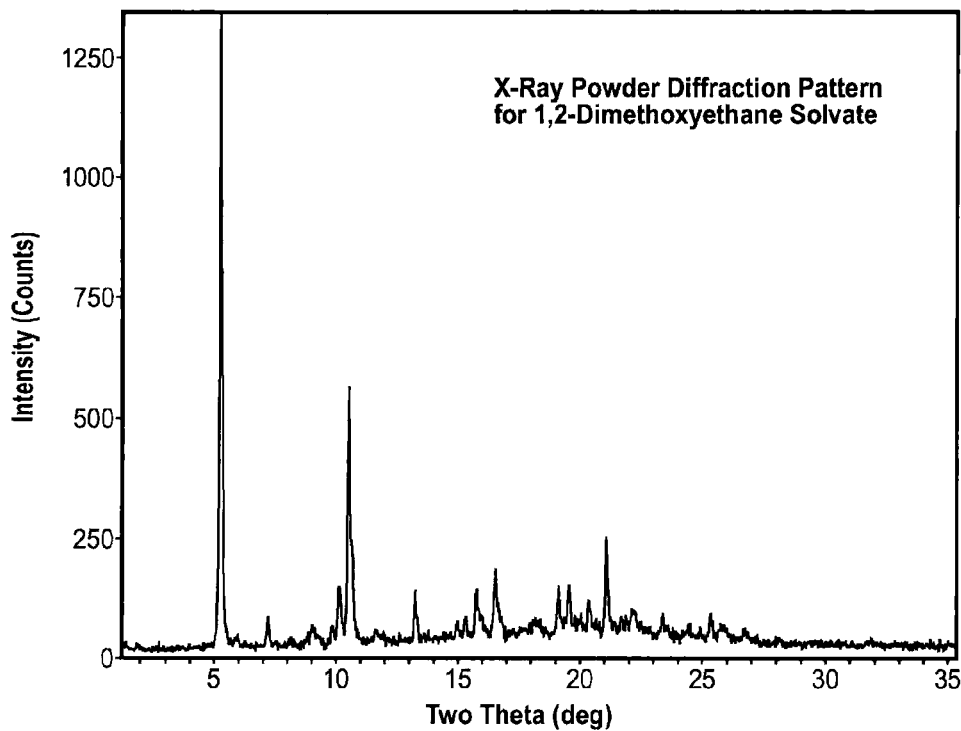
FIG. 21A is a graph illustrating a powder X-ray diffraction pattern of an embodiment of a crystalline form of a rapamycin analog 1,2-dimethoxyethane solvate.

In one embodiment, the crystalline rapamycin analog has a powder X-ray diffraction pattern with a peak at about 5.3, 10.1, 10.5, 15.8, 16.5, 19.1, 19.6, and/or 21.1. Also, the powder X-ray diffraction pattern is substantially as shown in FIG. 21A.

Figure 21B:
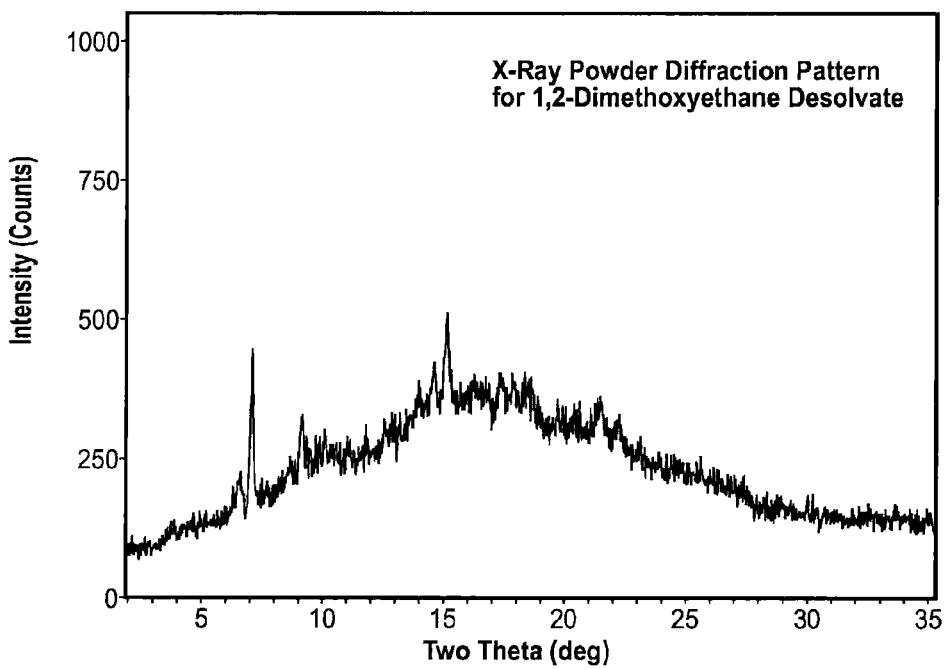
FIG. 21B is a graph illustrating a powder X-ray diffraction pattern of an embodiment of a crystalline form of a rapamycin analog 1,2-dimethoxyethane desolvate.

In one embodiment, the crystalline rapamycin analog has a powder X-ray diffraction pattern with a peak at about 6.6, 7.1, 9.2, 14.6, and/or 15.2. Also, the powder X-ray diffraction pattern is substantially as shown in FIG. 21B.

As with all types of instrumentation, the type of equipment and operating conditions can affect data. As such, the powder X-ray diffraction data can be slightly altered depending on the equipment and conditions. Accordingly, the powder X-ray diffraction data can be accurate to within 0.5, more preferably, 0.2, and most preferably to about 0.1. Also, characterization of the crystal structures can include at least 2 peaks, 3 peaks, 4 peaks, 5 peaks, 6 peaks, 7 peaks, 8 peaks, 9 peaks, and/or 10 peaks depending on the powder x-ray diffraction pattern.

Also, the powder X-ray diffraction patterns were measured using copper-K alpha-one (Cu K$\alpha$1) radiation at about 1.54056 Å. Also, powder X-ray diffraction patterns can be measured with. Also, Cu K$\alpha$1 and Cu K$\alpha$1 radiation can be used with a wavelength of 1.54178 Å, which is for unresolved.

Single crystal units can be measured with a graphite monochromator, but without a foil filter. The wavelength can be 0.71073 Å for a single crystal. Also, 0.71703 Å can be used for unresolved Mo radiation or 0.70930 Å for exclusively K$\alpha$1.

In one embodiment, the crystalline rapamycin analog is present at a therapeutically effective amount.

III. Preparing Crystalline Rapamycin Analogs

Crystalline rapamycin analogs can be prepared by the methods described herein. As such, various common parameters can be controlled to promote crystallization. Such common processing parameters include, but are not limited to, adjusting the temperature; adjusting the time; adjusting the pH; adjusting the amount or the concentration of compound-of-interest; adjusting the amount or the concentration of a component; component identity (e.g., adding one or more additional components); adjusting the solvent removal rate; introducing of a nucleation event; introducing of a precipitation event; controlling evaporation of the solvent (e.g. adjusting a value of pressure or adjusting the evaporative surface area); and adjusting the solvent composition. Other crystallization methods include sublimation, vapor diffusion, desolvation of crystalline solvates, and grinding (Guillory, J. K., Polymorphism in Pharmaceutical Solids, 186, 1999).

In one embodiment, the crystallization of the rapamycin analog can be conducted by modulating the temperature or cycling the temperature to induce crystallization. As such, the crystallization processes include dissolving the rapamycin analog into one or more solvents that may or may not include one or more antisolvents. Solubility is commonly controlled by the composition (e.g., identity of components) and/or by the temperature. Temperature control is most common in industrial crystallizers where a solution of a substance is cooled from a state in which it is freely soluble to one where the solubility is exceeded, thereby being supersaturated. For example, the crystalline rapamycin analogs can be prepared by heating to a temperature (T1), preferably to a temperature at which the all the solids are completely dissolved in solution. The composition is then cooled to a lower temperature (T2). The presence of solids can then be determined. A temperature sensor can be used to record the temperature when the first crystal or precipitate is detected.

In one embodiment, a large number or array of rapainycin analog compositions can be processed individually at the same time with respect to temperature and small heaters, cooling coils, and temperature sensors for each sample are provided and controlled. This approach is useful if each sample has the same composition and the experiment is designed to sample a large number of temperature profiles to find those profiles that produce desired solid-forms. In one embodiment, the composition of each sample is controlled and the entire array of compositions is heated and cooled as a unit.

Typically, several distinct temperatures and/or temperature profiles are tested during crystal nucleation and growth phases. Temperature can be controlled in either a static or dynamic manner. Static temperature means that a set incubation temperature is used throughout the crystallization. Alternatively, a temperature gradient can be used. For example, the temperature can be lowered at a certain rate throughout the crystallization. Furthermore, temperature can be controlled in a way as to have both static and dynamic components. For example, a constant temperature (e.g., 60 degrees Celsius) is maintained during the mixing of crystallization reagents. After mixing of reagents is complete, controlled temperature decline is initiated (e.g., 60 degrees Celsius to about 25 degrees Celsius over minutes).

In one embodiment, the crystallization of the rapamycin analog can be conducted by modulating the time of incubating the composition to induce crystallization. Accordingly, different rapamycin analog compositions can be incubated for various lengths of time (e.g., 5 minutes, 60 minutes, 48 hours, etc.) to induce and complete crystallization. Since phase changes can be time dependent, it can be advantageous to monitor crystallization of the rapamycin analog as a function of time.

In many cases, time control is very important, for example, the first solid-form to crystallize may not be the most stable, but rather a metastable form which can then convert to a form stable over a period of time. This process is called "ageing." Ageing also can be associated with changes in crystal size and/or habit. This type of ageing phenomena is called Ostwald ripening. Thus, incubating the crystallization composition for different time periods can be used to induce crystallization as well as promote crystallization into the desired crystal product.

In one embodiment, the crystallization of the rapamycin analog can be conducted by modulating the pH of the composition to induce or promote crystallization. The pH of the rapamycin analog composition can determine the physical state and properties of the crystal that is generated. The pH can be controlled by the addition of inorganic and organic acids and bases, such as well known buffers that are standards in the art. The pH of samples can be monitored with standard pH meters modified according to the volume of the sample.

In one embodiment, the crystallization of the rapamycin analog can be conducted by modulating the concentration of the rapamycin analog in the composition to induce or promote crystallization. Supersaturation is the thermodynamic driving force for both crystal nucleation and growth, and thus is a key variable in preparing crystalline rapamycin analogs. Supersaturation is the deviation from thermodynamic solubility equilibrium so that more solute (e.g., rapamycin analog) is suspended in the solution. Thus the degree of saturation can be controlled by temperature and the amounts or concentrations of the rapamycin analog and other components, such as adducts. In general, the degree of saturation can be controlled in the metastable region, and when the metastable limit has been exceeded, nucleation will be induced.

The amount or concentration of the rapamycin analog and/or other components can greatly affect physical state and properties of the resulting solid-form. As such, for a given temperature, nucleation and growth will occur at varying amounts of supersaturation depending on the composition of the starting solution. Nucleation and growth rate increases with increasing saturation, which can affect crystal habit. For example, rapid growth must accommodate the release of the heat of crystallization. This heat effect is responsible for the formation of dendrites during crystallization. The macroscopic shape of the crystal is profoundly affected by the presence of dendrites and even secondary dendrites.

The second effect that the relative amounts rapamycin analog and solvent has is the chemical composition of the resulting solid-form. For example, the first crystal to be formed from a concentrated solution is formed at a higher temperature than that formed from a dilute solution. The equilibrium solid phase is that from a higher temperature in the phase diagram, and a concentrated solution may first form crystals of the hemihydrate when precipitated from aqueous solution at high temperature. The dihydrate may, however, be the first to form when starting with a dilute solution. In this case, the rapamycin analog/solvent phase diagram is one in which the dihydrate decomposes to the hemihydrate at a high temperature. This is normally the case and usually holds for commonly observed solvates.

In one embodiment, the crystallization of the rapamycin analog can be conducted by modulating the identity of components in the composition, such as solvents and/or adducts, to induce or promote crystallization. The identity of the components in the composition can have a profound effect on almost all aspects of crystallization. Component identity can promote or inhibit crystal nucleation and growth as well as the physical state and properties of the resulting crystals. Thus, a component can be a substance whose intended effect is to induce, inhibit, prevent, or reverse formation of crystalline forms of the rapamycin analog.

A component can direct formation of crystals, amorphous-solids, hydrates, solvates, or salt forms of the rapamycin analog. Components also can affect the internal and external structure of the crystals formed, such as the polymorphic form and the crystal habit. Examples of components include, but are not limited to, excipients, solvents, salts, acids, bases, gases; small molecules, such as hormones, steroids, nucleotides, nucleosides, and amino acids; large molecules, such as oligonucleotides, polynucleotides, oligonucleotide and polynucleotide conjugates, proteins, peptides, peptidomimetics, and polysaccharides; other pharmaceuticals; crystallization additives, such as additives that promote and/or control nucleation, additives that affect crystal habit, and additives that affect polymorphic form; additives that affect particle or crystal size; additives that structurally stabilize crystalline or amorphous solid-forms; additives that dissolve solid-forms; additives that inhibit crystallization or solid formation; optically-active solvents; optically-active reagents; and optically-active catalysts.

In one embodiment, the crystallization of the rapamycin analog can be conducted by modulating the solvent removal rate and/or antisolvent removal rate to induce or promote crystallization. Control of solvent removal is intertwined with control of saturation. As the solvent is removed, the concentration of the rapamycin analog and less volatile components becomes higher. Depending on the remaining composition, the degree of saturation will change depending on factors, such as the polarity and viscosity of the remaining composition. For example, as a solvent is removed, the concentration of the rapamycin analog can rise until the metastable limit is reached and nucleation and crystal growth occur.

The rate of solvent removal can be controlled by temperature and pressure and the surface area under which evaporation can occur. For example, solvent can be removed by distillation at a predefined temperature and pressure, or the solvent can be removed simply by allowing the solvent to evaporate at room temperature. In some instances, solvent absorbents can be used.

In one embodiment, the crystallization of the rapamycin analog can be conducted by introducing a nucleation or precipitation event. In general, this involves subjecting a supersaturated rapamycin analog solution to some form of energy, such as ultrasound or mechanical stimulation, or by inducing supersaturation by adding additional components.

Crystal nucleation is the formation of a crystal solid phase from a liquid, an amorphous phase, a gas, or from a different crystal solid phase. Nucleation sets the character of the crystallization process and is therefore one of the most critical components in designing commercial crystallization processes (The Encyclopedia of Chemical Technology, 7 Kirk-Othomer (4th ed. at 692) (1993)).

Primary nucleation can occur by heterogenous or homogeneous mechanisms, both of which involve crystal formation by sequential combining of crystal constituents. Primary nucleation does not involve existing crystals of the rapamycin analog, but results from spontaneous formation of crystals. Primary nucleation can be induced by increasing the saturation over the metastable limit or, when the degree of saturation is below the metastable limit by nucleation. Nucleation events include mechanical stimulation, such as contact of the crystallization medium with the stirring rotor of a crystallizer and exposure to sources of energy, such as acoustic (ultrasound), electrical, or laser energy (Garetz et al., 1996 Physical review Letters 77:3475). Primary nucleation can also be induced by adding primary nucleation promoters, such as substances other than a solid-form of the rapamycin analog. Additives that decrease the surface energy of the rapamycin analog can induce nucleation. A decrease in surface energy favors nucleation, since the barrier to nucleation is caused by the energy increase upon formation of a solid-liquid surface. Thus, nucleation can be controlled by adjusting the interfacial tension of the crystallizing medium by introducing surfactant-like molecules either by pre-treating the crystallization chamber or by direct addition. The nucleation effect of surfactant molecules is dependent on their concentration and thus this parameter should be carefully controlled. Such tension adjusting additives are not limited to surfactants. Many compounds that are related to the rapamycin analog can have significant surface activity. Other heterogeneous nucleation inducing additives include solid particles of various substances, such as solid-phase excipients or even impurities left behind during synthesis or processing of the rapamycin analog.

Secondary nucleation involves treating the crystallizing medium with a secondary nucleation promoter that is a solid-form, preferably a crystal having characteristics that are desired for the crystalline rapamycin analog. A desired small crystal form of the rapamycin analog can be used as a secondary nucleation promoter. Direct seeding with a plurality of nucleation seeds of the rapamycin analog in various physical states provides a means to induce formation of different crystal forms in different compositions. In one embodiment, particles other than the rapamycin analog are added to the crystallization compositions. In another embodiment, nanometer-sized crystals (e.g., nanoparticles) of the rapamycin analog are added to the samples.

Crystalline forms of a rapamycin analog, such as ABT-578 (i.e., zotarolimus), have been discovered in organic solvents that include acetone, toluene, acetonitrile, ethyl formate, isopropyl acetate, isobutyl acetate, ethanol, N,N dimethyl formamide, and anisole. The acetonitrile solvent can be used to crystallize the rapamyein acetonitrile solvate, which then forms a crystalline desolvate (i.e., acetonitrile desolvated solvate) upon drying (e.g., appropriate drying conditions of pressure, temperature and vapor environment) so as to remove the acetonitrile from the crystal. The crystalline acetonitrile desolvated solvate may possess chemical stability properties that allow the elimination of addition of BHT as an antioxidant to the amorphous ABT-578, as is currently practiced. In addition, the impurity profile of ABT-578 may be improved significantly by incorporating a crystallization step in the manufacturing process, as described herein. In some of the powder X-ray diffraction (PXRD) patterns shown in the figures, two peaks at ~38 and 44 are from the X-ray holder.

There are various methods of preparing a crystalline rapamycin analog. In an embodiment, a method of preparing crystalline rapamycin analog drug substance includes, crystallizing rapamycin analog from a pharmaceutically acceptable solvent or mixture of solvents. In other embodiments, a method of preparing crystalline rapamycin analog drug substance includes crystallizing rapamycin analog from an organic solvent or mixture of solvents. Of course, one skilled in the art would be able to appreciate all the solvents that can be utilized with embodiments of the invention and not be limited to listed solvents herein.

In one embodiment, the present invention includes a process for preparing a crystalline form of a rapamycin analog. Such a process comprises the following: combining the rapamycin analog with at least one organic medium to form a mixture; incubating the mixture until the rapamycin analog crystallizes; and recovering the crystalline rapamycin analog from the organic medium.

In one embodiment, the organic medium can be comprised of at least one solvent to form the mixture. As such, the process for preparing the crystalline form of the rapamycin analog includes causing the rapamycin analog to dissolve into the solvent, and incubating the solvent until the rapamycin analog crystallizes.

In one embodiment, the process includes forming a slurry of crystalline rapamycin analog in the solution. In one embodiment, the process includes stirring the rapamycin analog mixture until the rapamycin analog crystallizes. In one embodiment, the process includes saturating the rapamycin analog solution. This can include forming a supersaturated rapamycin analog solution.

In one embodiment, the process includes the use of an antisolvent to aid in forming the crystalline rapamycin analog. Such a method includes combining at least one antisolvent with the rapamycin analog and the solvent to form a biphasic mixture, and incubating the biphasic mixture to cause a liquid-liquid phase split with a majority of the rapamycin analog being in the solvent and a minority of the rapamycin analog being in the antisolvent. Optionally, the solvent can be separated from the antisolvent before the crystals are separated out.

In one embodiment, the organic medium is toluene, acetonitrile, ethanol, isobutyl acetate, ethyl formate, isopropyl acetate, ethanol, N,N-dimethyl formamide, and combinations thereof.

In one embodiment, the solvent is an organic solvent. As such, the organic solvent can be a polar organic solvent. Examples of polar organic solvents include acetone, ethyl acetate, methanol, ethanol, n-propanol, isopropanol, isobutanol, tertbutanol, 2-butanol, acetronitrile, tetrahydrofuran, isobutyl acetate, n-butyl acetate, ethyl formate, n-propyl acetate, isopropyl acetate, methylethyl ketone, or any combination thereof. Preferably, the polar organic solvent is acetone. Examples of the antisolvent include cyclohexane, heptane, hexane, n-octane, iso-octane, methylcyclohexane, or any combination thereof. Preferably, the antisolvent is heptane. Preferably, the organic medium is pharmaceutically acceptable for making a pharmaceutical preparation. For example, the organic medium can be a pharmaceutically acceptable solvent that is acceptable for preparing a pharmaceutical-grade composition.

In one embodiment, the rapamycin analog solution (e.g., mixture, biphasic, etc.) is formed, incubated, stirred, mixed, slurried, saturated, and/or crystallized at a temperature from about −20 degrees Celsius to about 20 degrees Celsius, more preferably from about −10 degrees Celsius to about 10 degrees Celsius, even more preferably at about −5 degrees Celsius to about 5 degrees Celsius, and most preferably at about 0 degrees Celsius.

In one embodiment, the rapamycin analog solution (e.g., mixture, biphasic, etc.) is formed, incubated, stirred, mixed, slurried, saturated, and/or crystallized at a temperature from about 10 degrees Celsius to about 40 degrees Celsius, more preferably from about 12 degrees Celsius to about 32 degrees Celsius, even more preferably at about 20 degrees Celsius to about 25 degrees Celsius, and most preferably at about 22 degrees Celsius.

In one embodiment, the raparnycin analog solution (e.g., mixture, biphasic, etc.) is formed, incubated, stirred, mixed, slurried, saturated, and/or crystallized for about 0.1 to about 35 hours, more preferably from about 1 to about 30 hours, even more preferably from about 5 to about 25 hours, still more preferably from about 10 to about 20 hours, and most preferably for about 15 hours.

In one embodiment, the rapamycin analog combined with the organic medium is a crystalline form. For example, the crystalline form of the rapamycin analog can be an acetonitrile solvate, acetonitrile desolvated solvate (i.e., acetonitrile desolvate). Alternatively, the rapamycin analog can be in an amorphous state.

In one embodiment, the rapamycin mixture in the organic medium is combined with a second organic medium, and wherein the mixture that is further proccessed (e.g., incubated, stirred, mixed, slurried, saturated, and/or crystallized) includes the second organic medium. For example, the first organic medium can be acetonitrile, toluene, ethanol, isobutyl acetate, anisole or combinations thereof. Examples of the second organic medium can be ethyl formate, isopropyl acetate, ethanol, N,N, dimethyl formamide, anisole, and combinations thereof.

In one embodiment, a crystalline rapamycin analog in the form of an acetonitrile solvate can be prepared by incubating a biphasic mixture of dissolved rapamycin analog, acetone and heptane at about 0 degrees Celsius. Accordingly, the rapamycin analog can be added to a vial containing acetone and heptane so as to saturate the liquid phase. A liquid-liquid phase occurs as the rapamycin analog dissolved into solution resulting in a rapamycin analog-acetone rich bottom phase and a heptane rich top phase. For example, the biphasic mixture can be incubated at about 0 degrees Celsius for about 0.1 to about 10 days or longer until crystals can be observed at the bottom of the vial. The crystals can then be analyzed by powder X-ray diffraction, which is shown by FIG. 2A. The crystals can be equilibrated at ambient temperature followed by further drying at about 30 degrees Celsius under vacuum (approximately 3 inches of mercury). The dried crystals can be analyzed by powder X-ray diffraction, which is shown in FIG. 3A.

In one embodiment, a crystalline rapamycin analog in the form of acetone solvate can be prepared by dissolving amorphous rapamycin analog in acetone at ambient temperature and incubating the resulting solution at about 5 degrees Celsius until crystalline solids are observed. The crystals can be analyzed by powder X-ray diffraction, which is shown in FIG. 2B. The crystals can be equilibrated at ambient temperature followed by further drying at about 30 degrees Celsius under vacuum (approximately 3 inches of mercury). The dried crystals can be analyzed by powder X-ray diffraction, which is shown in FIG. 3B.

In one embodiment, a crystalline rapamycin analog in the form of an toluene solvate can be prepared. As such, crystals of the rapamycin analog toluene solvate can be prepared by dissolving amorphous rapamycin analog in toluene to form a solution. The solution can be stirred at about 22 degrees Celsius for about 15 hours or until a thick slurry of crystalline solids can be observed. Also, crystals can be prepared by using a crystalline rapamycin analog, such as an acetonitrile solvate, to seed the composition and induce crystallization. The crystals can then be analyzed by powder X-ray diffraction, which is shown by FIG. 4A.

In one embodiment, a crystalline rapamycin analog in the form of another acetonitrile solvate can be prepared. As such, crystals of an acetonitrile solvate can be generated by saturating acetonitrile with amorphous rapamycin analog at about 22 degrees Celsius and incubating at about 0 degrees Celsius for about 2 hours or until crystals form. The crystals can then be analyzed by powder X-ray diffraction, which is shown by FIG. 5A. FIG. 6A shows the powder X-ray diffraction pattern analysis data for the rapamycin analog acetonitrile desolvate, which can be obtained by drying the acetonitrile solvate.

In one embodiment, a crystalline rapamycin analog in the form of an ethyl formate solvate can be prepared. As such, crystals of the rapamycin analog ethyl formate solvate can be generated by slurrying a wetcake of the acetonitrile solvate in ethyl formate at about 0 degrees Celsius. The crystals can then be analyzed by powder X-ray diffraction, which is shown by FIG. 7A.

In one embodiment, a crystalline rapamycin analog in the form of an isopropyl acetate solvate can be prepared. As such, crystals of the rapamycin analog isopropyl acetate solvate can be generated by slurrying a wetcake of acetonitrile solvate in isopropyl acetate at about 0 degrees Celsius.

In one embodiment, a crystalline rapamycin analog in the form of an isobutyl acetate solvate can be prepared. As such, crystals of the rapamycin analog isobutyl acetate can be prepared by adding amorphous rapamycin analog a vial and charging isobutyl acetate into the vial to enable dissolution. The solution can then be incubated at about 0 degrees Celsius for about 16 hours or until a crystalline slurry is obtained. The crystals can then be analyzed by powder X-ray diffraction, which is shown by FIG. 9A.

In one embodiment, a crystalline rapamycin analog in the form of an ethanol solvate can be prepared. As such, crystals of the rapamycin analog ethanol solvate can be prepared by adding amorphous rapamycin analog to in a vial and charging ethanol (200 proof) into the vial to enable dissolution, The solution can be seeded after about 15 hours with an acetonitrile desolvate, and then incubated at about 0 degrees Celsius for an additional about 16 hours until a crystalline slurry is obtained, In one embodiment, a crystalline rapamycin analog in the form of an N,N, dimethyl formamide solvate can be prepared. As such, crystals of the rapamycin analog N,N dimethyl formamide solvate can be generated by slurrying a wetcake of acetonitrile solvate in N,N Dimethyl formamide at about 0 degrees Celsius. The crystals can then be analyzed by powder X-ray diffraction, which is shown by FIG. 10A.

In one embodiment, a crystalline rapamycin analog in the form of an anisole solvate can be prepared. As such, crystals of the rapamycin analog anisole solvate can be generated by slurrying a wetcake of acetonitrile solvate in anisole at about 0 degrees Celsius. The crystals can then be analyzed by powder X-ray diffraction, which is shown by FIG. 11A.

IV. Crystalline Rapamycin Analog Compositions

The crystalline rapamycin analog of the present invention can be prepared into any pharmaceutical composition, such as the compositions commonly employed with amorphous rapamycin analogs. Accordingly, the crystalline rapamycin analog can be formulated into a polymeric composition, such as a stent coating or the like. The polymeric composition can include polymers that are hydrophilic, hydrophobic, biodegradable, non-biodegradable, and any combination thereof. The polymer can be selected from the group consisting of polyacrylates, polymethacrylates, polycarboxylic acids, cellulosic polymers, gelatin, polyvinylpyrrolidone, maleic anhydride polymers, polyamides, polyvinyl alcohols, polyethylene oxides; glycosaminoglycans, polysaccharides, polyesters, polyurethanes, silicones, polyorthoesters, polyanhydrides, polycarbonates, polypropylenes, polylactic acids, polyglycolic acids, polycaprolactones, polyhydroxybutyrate valerates, polyacrylamides, polyethers, and mixtures and copolymers of the foregoing. Also, polymeric dispersions, such as polyurethane dispersions (BAYHYDROL, etc.) and acrylic acid latex dispersions, can also be used.

Biodegradable polymers that can be used include poly(L-lactic acid), poly(DL-lactic acid), polycaprolactone, poly(hydroxy butyrate), polyglycolide, poly(diaxanone), poly(hydroxy valerate), polyorthoester, copolymers, poly(lactide-co-glycolide), polyhydroxy(butyrate-co-valerate), poly glycolide-co-trimethylene carbonate, polyanhydrides, polyphosphoester, polyphosphoester-urethane, polyamino acids, polycyanoacrylates, biomolecules, fibrin, fibrinogen, cellulose, starch, collagen hyaluronic acid, and any combination thereof. Biostable polymers can also be used, such as polyurethane, silicones, polyesters, polyolefins, polyamides, polycaprolactam, polyimide, polyvinyl chloride, polyvinyl methyl ether, polyvinyl alcohol, acrylic polymers and copolymers, polyacrylonitrile, polystyrene copolymers of vinyl monomers with olefins (such as styrene acrylonitrile copolymers, ethylene methyl methacrylate copolymers, ethylene vinyl acetate), polyethers, rayons, cellulosics (such as cellulose acetate, cellulose nitrate, cellulose propionate, etc.), parylene and derivatives thereof, and any combination hereof.

Other polymers that can be used include a MPC subunit including poly(MPC$_w$:LAM$_x$:HPMA$_y$:TSMA$_z$) where w, x, y, and z represent the molar ratios of monomers used in the feed for preparing the polymer and MPC represents the unit 2-methacryoyloxyethylphosphorylcholine, LMA represents the unit lauryl methacrylate. HPMA represents the unit 2-hydroxypropyl methacrylate, and TSMA represents the unit 3-trimethoxysilylpropyl methacrylate.

Additionally, the crystalline rapamycin analogs can be prepared into any pharmaceutical composition. Such pharmaceutical compositions can include a pharmaceutically acceptable carrier or excipient, which may be administered orally, rectally, parenterally, intracisternally, intravaginally, intraperitoneally, topically (as by powders, ointments, drops or transdermal patch), bucally, as an oral or nasal spray, or locally, such as in a stent placed within the vasculature. The phrase "pharmaceutically acceptable carrier" refers to a non-toxic solid, semi-solid or liquid filler, diluent, encapsulating material or formulation auxiliary of any type. The term "parenteral" refers to modes of administration which include intravenous, intraarterial, intramuscular, intraperitoneal, intrasternal, subcutaneous and intraarticular injection, infusion, and placement, such as, for example, in vasculature.

The pharmaceutical compositions can include pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles including water, ethanol, polyols (e.g., glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The pharmaceutical compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminum monostearate and gelatin.

In some cases, in order to prolong the effect of the crystalline rapamycin analog, it is desirable to slow the absorption of the crystalline rapamycin analog from subcutaneous or intramuscular injection. This may be accomplished by the use of a liquid suspension of crystalline or amorphous material with poor water solubility. The rate of absorption of the crystalline rapamycin analog then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the crystalline rapamycin analog is mixed with at least one inert, pharmaceutically acceptable excipient or carrier such as sodium citrate or dicalcium phosphate and/or (a) fillers or extenders such as starches, lactose, sucrose, glucose. mannitol, and silicic acid, (b) binders such as, for example, carboxymethylcellulose, alginates, gelatin, polyvinylpyrrolidone, sucrose, and acacia, (c) humectants such as glycerol, (d) disintegrating agents such as agar-agar, calcium carbonate, potato or tapioca starch, alginic acid, certain silicates and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft, semi-solid and hard-filled gelatin capsules or liquid-filled capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Those embedding compositions containing a drug can be placed on medical devices, such as stents, grafts, catheters, and balloons. The crystalline rapamycin analog can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the crystalline rapamycin analog, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of about 0.01 to about 10 micrometers. Compositions for topical use on the skin also include ointments, creams, lotions, and gels.

Alternatively, the composition may be pressurized and contain a compressed gas, such as nitrogen or a liquified gas propellant. The liquified propellant medium and indeed the total composition is preferably such that the active ingredient does not dissolve therein to any substantial extent. The pressurized composition may also contain a surface active agent. The surface active agent may be a liquid or solid non-ionic surface active agent or may be a solid anionic surface active agent. It is preferred to use the solid anionic surface active agent in the form of a sodium salt.

A further form of topical administration is to the eye, as for the treatment of immune-mediated conditions of the eye such as autoimmune diseases, allergic or inflammatory conditions, and corneal transplants. The crystalline rapamycin analog is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/cilary, lens, choroid/retina and sclera. The pharmaceutically acceptable ophthalmic vehicle may, for example, be an ointment, vegetable oil or an encapsulating material.

Compositions for rectal or vaginal administration are preferably suppositories or retention enemas which can be prepared by mixing the crystalline rapamycin analog with suitable non-irritating excipients or carriers such as cocoa butter, polyethylene glycol or a suppository wax which are solid at room temperature but liquid at body temperature and therefore melt in the rectum or vaginal cavity and release the active compound.

Crystalline rapamycin analog can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. (See, Prescott. Ed., Methods in Cell Biology, Volume XIV, Academic Press, New York, N.Y. (1976), p. 33 et seq.)

The crystalline rapamycin analog can be applied to stents that have been coated with a polymeric compound. Incorporation of the compound or drug into the polymeric coating of the stent can be carried out by dipping the polymer-coated stent into a solution containing the compound or drug for a sufficient period of time (such as, for example, five minutes) and then drying the coated stent, preferably by means of air drying for a sufficient period of time (such as, for example, 30 minutes). The polymer-coated stem containing the compound or drug can then be delivered to the coronary vessel by deployment from a balloon catheter. In addition to stents, other devices that can be used to introduce the drugs of this invention to the vasculature include, but are not limited to grafts, catheters, and balloons. In addition, other compounds or drugs that can be used in lieu of the drugs of this invention include, but are not limited to, A-94507 and SDZ RAD (a.k.a. Everolimus).

The crystalline rapamycin analog can be used in combination with other pharmacological agents. The pharmacologic agents that can be effective in preventing restenosis can be classified into the categories of anti-proliferative agents, anti-platelet agents, anti-inflammatory agents, anti-thrombotic agents, and thrombolytic agents. These classes can be further sub-divided. For example, anti-proliferative agents can be anti-mitotic. Anti-mitotic agents inhibit or affect cell division, whereby processes normally involved in cell division do not take place. One sub-class of anti-mitotic agents includes vinca alkaloids. Representative examples of vinca alkaloids include, but are not limited to, vincristine, paclitaxel, etoposide, nocodazole, indirubin, and anthracycline derivatives, such as, for example, daunorubicin, daunomycin, and plicamycin. Other sub-classes of anti-mitotic agents include anti-mitotic alkylating agents, such as, for example, tauromustin, bofumustine, and fotemustine, and anti-mitotic metabolites, such as, for example, methotrexate, fluorouracil, 5-bromodeoxyuridine, 6-azacytidine, and cytarabine. Anti-mitotic alkylating agents affect cell division by covalently modifying DNA, RNA, or proteins, thereby inhibiting DNA replication, RNA transcription, RNA translation, protein synthesis, or combinations of the foregoing.

Anti-platelet agents are therapeutic entities that act by (1) inhibiting adhesion of platelets to a surface, typically a thrombogenic surface, (2) inhibiting aggregation of platelets, (3) inhibiting activation of platelets, or (4) combinations of the foregoing. Activation of platelets is a process whereby platelets are converted from a quiescent, resting state to one in which platelets undergo a number of morphologic changes induced by contact with a thrombogenic surface. These changes include changes in the shape of the platelets, accompanied by the formation of pseudopods, binding to membrane receptors, and secretion of small molecules and proteins, such as, for example, ADP and platelet factor 4. Anti-platelet agents that act as inhibitors of adhesion of platelets include, but are not limited to, eptifibatide, tirofiban, RGD (Arg-Gly-Asp)-based peptides that inhibit binding to gpIIbIIIa or $\alpha v \beta 3$, antibodies that block binding to gpIIbIIIa or $\alpha v \beta 3$, anti-P-selectin antibodies, anti-E-selectin antibodies, compounds that block P-selectin or E-selectin binding to their respective ligands, saratin, and anti-von Willebrand factor antibodies. Agents that inhibit ADP-mediated platelet aggregation include, but are not limited to, disagregin and cilostazol.

Anti-inflammatory agents can also be used. Examples of these include, but are not limited to, prednisone, dexamethasone, hydrocortisone, estradiol, fluticasone, clobetasol, and non-steroidal anti-inflammatories, such as, for example, acetaminophen, ibuprofen, naproxen, and sulindac. Other examples of these agents include those that inhibit binding of cytokines or chemokines to the cognate receptors to inhibit pro-inflammatory signals transduced by the cytokines or the chemokines. Representative examples of these agents include, but are not limited to, anti-IL1, anti-IL2, anti-IL3, anti-IL4, anti-IL8, anti-IL15, anti-IL18, anti-GM-CSF, and anti-TNF antibodies.

Anti-thrombotic agents include chemical and biological entities that can intervene at any stage in the coagulation pathway. Examples of specific entities include, but are not limited to, small molecules that inhibit the activity of factor Xa. In addition, heparinoid-type agents that can inhibit both FXa and thrombin, either directly or indirectly, such as, for example, heparin, heparin sulfate, low molecular weight heparins, such as, for example, the compound having the trademark Clivarin®, and synthetic oligosaccharides, such as, for example, the compound haying the trademark Arixtra®. Also included are direct thrombin inhibitors, such as, for example, melagatran, ximelagatran, argatroban, inogatran, and peptidomimetics of binding site of the Phe-Pro-Arg fibrinogen substrate for thrombin. Another class of anti-thrombotic agents that can be delivered are factor VII/VIIa inhibitors, such as, for example, anti-factor VII/VIIa antibodies, rNAPc2, and tissue factor pathway inhibitor (TFPI).

Thrombolytic agents, which may be defined as agents that help degrade thrombi (clots), can also be used as adjunctive agents, because the action of lysing a clot helps to disperse platelets trapped within the fibrin matrix of a thrombus. Representative examples of thrombolytic agents include, but are not limited to, urokinase or recombinant urokinase, pro-urokinase or recombinant pro-urokinase, tissue plasminogen activator or its recombinant form, and streptokinase.

Other drugs that can be used in combination with the crystalline rapamycin analog are cytotoxic drugs, such as, for example, apoptosis inducers, such as TGF, and topoisomerase inhibitors, such as, 10-hydroxycamptothecin, irinotecan, and doxorubicin. Other classes of drugs that can be used in combination with the crystalline rapamycin analog are drugs that inhibit cell de-differentiation and cytostatic drugs. Other agents that can be used in combination with the crystalline rapamycin analog include fenofibrate, batimistat, antagonists of the endothelin-A receptor, such as, for example, darusentan, and antagonists of the $\alpha v \beta 3$ integrin receptor.

Crystalline rapamycin analog may also be coadministered with one or more immunosuppressant agents. The immunosuppressant agents within the scope of this invention include, but are not limited to, IMURAN® azathioprine sodium. brequinar sodium, SPANIDIN® gusperimus trihydrochloride (also known as deoxyspergualin), mizoribine (also known as bredinin), CELLCEPT® mycophenolate mofetil, NEORAL® Cylosporin A (also marketed as different formulation of Cyclosporin A under the trademark SANDIMMUNE®), PROGRAF® tacrolimus (also known as FK-506), sirolimus and RAPAMUNE® leflunomide (also known as HWA-486), glucocorticoids, such as prednisolone and its derivatives, antibody therapies such as orthoclone (OKT3) and Zenapax®, and antithymyocyte globulins, such as thymo globulins.

V. Crystalline Rapamycin Analog Treatments

The crystalline rapamycin analogs possess immunomodulatory activity in mammals (especially humans). As immunosuppressants, the crystalline rapamycin analogs are useful for the treatment and prevention of immune-mediated diseases such as the resistance by transplantation of organs or tissue such as heart, kidney, liver, medulla ossium, skin, cornea, lung, pancreas, intestinum tenue, limb, muscle, nerves, duodenum, small-bowel, pancreatic-islet-cell, and the like; graft-versus-host diseases brought about by medulla ossium transplantation; autoimmune diseases such as rheumatoid arthritis, systemic lupus erythematosus, Hashimoto's thyroiditis, multiple sclerosis, myasthenia gravis, Type I diabetes, uveitis, allergic encephalomyelitis, glomerulonephritis, and the like. Further uses include the treatment and prophylaxis of inflammatory and hyperproliferative skin diseases and cutaneous manifestations of immunologically-mediated illnesses, such as psoriasis, atopic dermatitis, contact dermatitis and further eczematous dermatitises, seborrhoeis dermatitis, lichen planus, pemphigus, bullous pemphigoid, epidermolysis bullosa, urticaria, angioedemas, vasculitides, erythemas, cutaneous eosinophilias, lupus erythematosus, acne, and alopecia greata; various eye diseases (autoimmune and otherwise) such as keratoconjunctivitis, vernal conjunctivitis, uveitis associated with Behcet's disease, keratitis, herpetic keratitis, conical cornea, dystrophia epithelialis corneae, corneal leukoma, and ocular pemphigus. In addition reversible obstructive airway disease, which includes conditions such as asthma (for example, bronchial asthma, allergic asthma, intrinsic asthma, extrinsic asthma, and dust asthma), particularly chronic or inveterate asthma (for example, late asthma and airway hyper-responsiveness), bronchitis, allergic rhinitis, and the like are targeted by the crystalline rapamycin analogs. Inflammation of mucosa and blood vessels such as gastric ulcers, vascular damage caused by ischemic diseases, and thrombosis. Moreover, hyperproliferative vascular diseases such as intimal smooth muscle cell hyperplasia, restenosis and vascular occlusion, particularly following biologically- or mechanically-mediated vascular injury, could be treated or prevented by the crystalline rapamycin analogs.

Other treatable conditions include but are not limited to ischemic bowel diseases, inflammatory bowel diseases, necrotizing enterocolitis, intestinal inflammations/allergies such as Coeliac diseases, proctitis, eosinophilic gastroenteritis, mastocytosis, Crohn's disease, and ulcerative colitis; nervous diseases such as multiple myositis, Guillain-Barre syndrome, Meniere's disease, polyneuritis, multiple neuritis, mononeuritis, and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia, and aneryrthroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity, and cutaneous T cell lymphoma; circulatory diseases such as arteriosclerosis, atherosclerosis, aortitis syndrome, polyarteritis nodosa, and myocardosis; collagen diseases such as scleroderma, Wegener's granuloma and Sjogren's syndrome; adiposis; eosinophilic fasciitis; periodontal disease such as lesions of gingiva, periodontium, alveolar bone, and substantia ossea dentis; nephrotic syndrome such as glornerulonephritis; male pattern aleopecia or alopecia senilis by preventing epilation or providing hair germination and/or promoting hair generation, and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation or ischemic disease (for example, thrombosis and cardiac infarction); intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring, and corneal alkali burn; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenesis, metastasis of carcinoma, and hypobaropathy; diseases caused by histamine or leukotriene-$C_4$ release; Behcet's disease such as intestinal-, vasculo- or neuro-Behcet's disease, and also Behcet's which affects the oral cavity, skin, eye, vulva, articulation, epididymis, lung, kidney, and so on.

Furthermore, the crystalline rapamycin analogs are useful for the treatment and prevention of hepatic disease such as immunogenic diseases (for example, chronic autoimmune liver diseases such as autoimmune hepatitis, primary biliary cirrhosis and sclerosing cholangitis), partial liver resection, acute liver necrosis (e.g., necrosis caused by toxin, viral hepatitis, shock or anoxia), B-virus hepatitis, non-A/non-B hepatitis, cirrhosis (such as alcoholic cirrhosis) and hepatic failure such as fulminant hepatic failure, late-onset hepatic failure and "acute-on-chronic" liver failure (acute liver failure on chronic liver diseases), and moreover are useful for various diseases because of their useful activity such as augmention of chemotherapeutic effect, cytomegalovirus infection, particularly HCMV infection, anti-inflammatory activity, sclerosing and fibrotic diseases such as nephrosis, scleroderma, pulmonary fibrosis, arteriosclerosis, congestive heart failure, ventricular hypertrophy, post-surgical adhesions and scarring, stroke, myocardial infarction and injury associated with ischemia and reperfusion, and the like.

Additionally, crystalline rapamycin analogs possess FK-506 antagonistic properties. The crystalline rapamycin analogs may thus be used in the treatment of immunodepression or a disorder involving immunodepression. Examples of disorders involving immunodepression include AIDS, cancer, fungal infections, senile dementia, trauma (including wound healing, surgery and shock), chronic bacterial infection, and certain central nervous system disorders. The immunodepression to be treated may be caused by an overdose of an immunosuppressive macrocyclic compound, for example derivatives of 12-(2-cyclohexyl-1-methylvinyl)-13,19,21,27-tetramethyl-11,28-dioxa-4-azatricyclo[22.3.10$^{4,9}$]octacos-18-ene such as FK-506 or rapamycin. The overdosing of such medicants by patients is quite common upon their realizing that they have forgotten to take their medication at the prescribed time and can lead to serious side effects.

The ability of the crystalline raparnycin analogs to treat proliferative diseases can be demonstrated according to the methods described in Bunchman E T and C A Brookshire, Transplantation Proceed. 23 967-968 (1991); Yamagishi, et al., Biochem. Biophys. Res. Comm. 191 840-846 (1993); and Shichiri, et al., J. Clin. Invest. 87 1867-1871 (1991). Proliferative diseases include smooth muscle proliferation, systemic sclerosis, cirrhosis of the liver, adult respiratory distress syndrome, idiopathic cardiomyopathy, lupus erythematosus, diabetic retinopathy or other retinopathies, psoriasis, scleroderma, prostatic hyperplasia, cardiac hyperplasia, restenosis following arterial injury or other pathologic stenosis of blood vessels. In addition, the crystalline rapamycin analogs antagonize cellular responses to several growth factors, and therefore possess antiangiogenic properties, making them useful agents to control or reverse the growth of certain tumors, as well as fibrotic diseases of the lung, liver, and kidney.

Aqueous liquid compositions are particularly useful for the treatment and prevention of various diseases of the eye such as autoimmune diseases (including, for example, conical cornea, keratitis, dysophia epithelialis corneae, leukoma. Mooren's ulcer, sclevitis, and Graves' opthalmopathy) and rejection of corneal transplantation.

When used in the above or other treatments, a therapeutically effective amount of one of the crystalline rapamycin analogs may be employed in pure form or, where such forms exist, in pharmaceutically acceptable salt, ester or prodrua form. Alternatively, the crystalline rapamycin analogs may be administered as a pharmaceutical composition containing the compound of interest in combination with one or more pharmaceutically acceptable excipients. The phrase "therapeutically effective amount" of the crystalline rapamycin analog means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex, and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the crystalline rapamycin analogs administered to a human or lower animal may range from about 0.01 to about 10 mg/kg/day. For purposes of oral administration, more preferable doses may be in the range of from about 0.001 to about 3 mg/kg/day. For the purposes of local delivery from a stent, the daily dose that a patient will receive depends on the length of the stent. For example, a 15 mm coronary stent may contain a drug in an amount ranging from about 1 to about 120 micrograms and may deliver that drug over a time period ranging from several hours to several weeks. If desired, the effective daily dose may be divided into multiple doses for purposes of administration; consequently, single dose compositions may contain such amounts or submultiples thereof to make up the daily dose. Topical administration may involve doses ranging from about 0.001 to about 3% mg/kg/day, depending on the site of application.

EXAMPLES

Example 1

The rapamycin analogs and processes of the present invention will be better understood in connection with the following synthetic schemes and methods of producing the rapamycin analogs and producing the crystallized forms of the rapamycin analogs, which illustrate the methods by which the crystalline rapamycin analogs of the present invention may be prepared.

The rapamycin analogs of this invention may be prepared by a variety of synthetic routes. A representative procedure is shown in FIG. 1. As shown in FIG. 1, conversion of the C-42 hydroxyl of rapamycin to a trifluoromethanesulfonate or fluorosulfonate leaving group provided Structure A. Displacement of the leaving group with tetrazole in the presence of a hindered, non-nucleophilic base, such as 2,6-lutidine, or, preferably, diisopropylethyl amine provided Formula 2 and Formula 3, which were separated and purified by flash column chromatography.

The foregoing may be better understood by reference to the following examples which illustrate the methods by which the compounds of the invention may be prepared and are not intended to limit the scope of the invention as defined in the appended claims.

Example 1A

Rapamycin (7.5 g) was dissolved in DCM (30 g). 2,6-Lutidine (1.76 g) was added. The solution was cooled to −30 C in acetonitrile-dry ice bath, and triflic anhydride (2.89 g) was added slowly in 10 minutes. The reaction mixture was stirred for 20 minutes, and then assayed for the presence of rapamycin to determine consumption in the reaction. 1-H-tetrazole (1.44 g), followed by DIEA (5.29 g) was added. The reaction mixture was stirred for 6 hours at room temperature, and then directly loaded on a silica gel (270 g) column prepared in 1:1 THF:n-heptane (v/v). The crude reaction mixture was purified with 1:1 THF:n-heptane. The fractions containing product that elute later (N-2 isomer elutes first followed by N-1 isomer) were collected and concentrated. The concentrated solids were dissolved in minimum DCM and loaded on a silica gel column (135 g) packed in 70:30 n-heptane:acetone. The column was eluted with 70:30 n-heptane:acetone, and fractions containing pure product, as identified by thin-layer chromatography (TLC), were concentrated.

The purified product was dissolved in t-BME (9 g), and added slowly to n-heptane (36 g) with vigorous stirring at 10+/−10 C. The precipitated solids were stirred at 5-10 C for 1 hour, filtered, washed with n-heptane and dried on the funnel with nitrogen. BHT (0.006 g) was added to the solids. The solids were dissolved in acetone (20 g), passed through a filter, and concentrated. The residue was treated with acetone twice (20 g each) and concentrated each time to dryness. The product was dried under vacuum for not less than 18 hours at not more than 50 C to give 2.5 g of zotarolimus.

Example 1B

A solution of Example 1A in isopropyl acetate (0.3 mL) was treated sequentially with diisopropylethylamine (87 uL, 0.5 mmol) and 1H-tetrazole (35 mg, 0.5 mmol), and thereafter stirred for 18 hours. This mixture was partitioned between water (10 mL) and ether (10 mL). The organics were washed with brine (10 mL) and dried ($Na_2SO4$). Concentration of the organics provided a sticky yellow solid which was purified by chromatography on silica gel (3.5 g, 70-230 mesh) eluting with hexane (10 mL), hexane:ether (4:1(10 mL), 3:1(10 mL), 2:1(10 mL), 1:1(10 mL)), ether (30 mL), hexane:acetone (1:1(30 mL)). One of the isomers was collected in the ether fractions (MS (ESI) m/e 966 (M)-; 42-(2-tetrazolyl)-rapamycin (less polar isomer) corresponding to Formula 3 of FIG. 1).

Example 1C

Collection of the slower moving band from the chromatography column using the hexane:acetone (1:1) mobile phase in Example 1C provided the designated compound (MS (ESI) m/e 966 (M)-; 42-(1-tetrazolyl)-rapamycin (more polar isomer) corresponding to Formula 2 of FIG. 1).

Example 2

The immunosuppressant activity of the rapamycin analogs of obtained from Example 1B and Example 1C was compared to rapamycin and two rapamycin analogs: 40-epi-N-[2'-pyridone]-rapamycin and 40-epi-N-[4'-pyridone]-rapamycin, both disclosed in U.S. Pat. No. 5,527,907. The activity was determined using the human mixed lymphocyte reaction (MLR) assay described by Kino, T. et al. in *Transplantation Proceedings*, XIX(5):36-39, Suppl. 6 (1987). The results of the assay demonstrate that the compounds of the invention are effective immunomodulators at nanomolar concentrations, as shown in Table 1.

TABLE 1

| Example | Human MLR $IC_{50}$ ± S.E.M. (nM) |
|---|---|
| Rapamycin | 0.91 ± 0.36 |
| 2-pyridone | 12.39 ± 5.3 |
| 4-pyridone | 0.43 ± 0.20 |
| Example 1 | 1.70 ± 0.48 |
| Example 2 | 0.66 ± 0.19 |

The pharmacokinetic behaviors of the rapamycin analogs of Example 1B and Example 1C were characterized following a single 2.5 mg/kg intravenous dose in cynomolgus monkey (n=3 per group). Each compound was prepared as 2.5 mg/mL solution in a 20% ethanol:30% propylene glycol:2% cremophor EL:48% dextrose 5% in water vehicle. The 1 mL/kg intravenous dose was administered as a slow bolus (~1-2 minutes) in a saphenous vein of the monkeys. Blood samples were obtained from a femoral artery or vein of each animal prior to dosing and 0.1 (IV only), 0.25, 0.5, 1, 1.5, 2, 4, 6, 9, 12, 24, and 30 hours after dosing. The EDTA preserved samples were thoroughly mixed and extracted for subsequent analysis.

An aliquot of blood (1.0 mL) was hemolyzed with 20% methanol in water (0.5 ml) containing an internal standard. The hemolyzed samples were extracted with a mixture of ethyl acetate and hexane (1:1 (v/v), 6.0 mL). The organic layer was evaporated to dryness with a stream of nitrogen at room temperature. Samples were reconstituted in methanol: water (1:1, 150 μL). The title compounds (50 μL injection) were separated from contaminants using reverse phase HPLC with UV detection. Samples were kept cool (4 degrees Celsius) through the run. All samples from each study were analyzed as a single batch on the HPLC.

Area under the curve (AUC) measurements of the rapamycin analogs of Example 1B, Example 1C, and the internal standard were determined using the Sciex MacQuan™ software. Calibration curves were derived from peak area ratio (parent drug/internal standard) of the spiked blood standards using least squares linear regression of the ratio versus the theoretical concentration. The methods were linear for both compounds over the range of the standard curve (correlation >0.99) with an estimated quantitation limit of 0.1 ng/mL. The maximum blood concentration ($C_{MAX}$) and the time to reach the maximum blood concentration ($T_{MAX}$) were read directly from the observed blood concentration-time data. The blood concentration data were submitted to multi-exponential curve fitting using CSTRIP to obtain estimates of pharmacokinetic parameters. The estimated parameters were further defined using NONLIN84. The area under the blood concentration-time curve from 0 to t hours (last measurable blood concentration time point) after dosing ($AUC_{0-t}$) was calculated using the linear trapeziodal rule for the blood-time profiles. The residual area extrapolated to infinity, determined as the final measured blood concentration (CO divided by the terminal elimination rate constant (β), and added to $AUC_{0-t}$ to produce the total area under the curve ($AUC_{0-t}$).

As shown in FIG. 2 and Table 1, both the rapamycin analogs of Example 1B and Example 1C had a surprisingly substantially shorter terminal elimination half-life ($t_{1/2}$) when compared to rapamycin. Thus, only the compounds of the invention provide both sufficient efficacy (Table 1) and a shorter terminal half-life (Table 2).

TABLE 2

| Compound | AUC ng hr/mL | $t_{1/2}$ (hours) |
|---|---|---|
| Rapamycin | 6.87 | 16.7 |
| 2-pyridone | 2.55 | 2.8 |
| 4-pyridone | 5.59 | 13.3 |
| Example 1 | 2.35 | 5.0 |
| Example 2 | 2.38 | 6.9 |

Example 3

The purpose of this example was to determine the effects of a rapamycin analog on neointimal formation in porcine coronary arteries containing stents. This example illustrates that the rapamycin analog A-179578 (e.g. ABT-578; corresponding to Formula 2 of FIG. 1), when compounded and delivered from the Biocompatibles BiodiviYsio PC Coronary stent favorably affects neointimal hyperplasia and lumen size in porcine coronary arteries. This finding suggests that such a combination may be of substantial clinical benefit if properly applied in humans by limiting neointirnal hyperplasia.

The study set forth in this example was designed to assess the ability of the rapamycin analog A-179578 to reduce neointimal hyperplasia in a porcine coronary stent model. Efficacy of A-179578 in this model would suggest its clinical potential for the limitation and treatment of coronary restenosis in stents following percutaneous revascularization. The domestic swine was used because this model appears to yield results comparable to other investigations seeking to limit neointimal hyperplasia in human subjects.

The example tested A-179578 eluted from coronary stents placed in juvenile farm pigs, and compared these results with control stents. The control stents are polymer-coated without drugs. This is important, for the polymer itself must not stimulate neointimal hyperplasia to a substantial degree. As the eluted drug disappears, an inflammatory response to the polymer could conceivably result in a late "catch-up phenomenon" where the restenosis process is not stopped, but instead slowed. This phenomenon would result in restenosis at late dates in human subjects.

Stems were implanted in two blood vessels in each pig. Pigs used in this model were generally 2-4 months old and weighed 30-40 kg. Two coronary stents were thus implanted in each pig by visually assessing a "normal" stent:artery ratio of 1.1-1.2.

Beginning on the day of the procedure, pigs were given oral aspirin (325 mg daily) and continued for the remainder of their course. General anesthesia was achieved by means of intramuscular injection followed by intravenous ketamine (30 mg/kg) and xylazine (3 mg/kg). Additional medication at the time of induction included atropine (1 mg) and flocillin (1 g) administered intramuscularly. During the stenting procedure, an intraarterial bolus of 10,000 units of heparin was administered.

Arterial access was obtained by cutdown on the right external carotid and placement of an 8F sheath. After the procedure, the animals were maintained on a normal diet without cholesterol or other special supplementation.

The BiodivYsio stent was used with nominal vessel target size of 3.0 mm. Two coronary arteries per pig were assigned at random to deployment of the stents. The stent was either a drug eluting stent (polymer plus drug stent) or a stent coated with a polymer only (polymer only stent). The stents were delivered by means of standard guide catheters and wires. The stent balloons were inflated to appropriate sizes for less than 30 seconds.

Each pig had one polymer only stent and one polymer plus drug stent placed in separate coronary arteries, so that each pig would have one stent for drug and one for control. A sample size of 20 pigs total was chosen to detect a projected difference in neointimal thickness of 0.2 mm with a standard deviation of 0.15 mm, at a power of 0.95 and beta 0.02.

Animals were euthanized at 28 days for histopathologic examination and quantification. Following removal of the heart from the perfusion pump system, the left atrial appendage was removed for access to the proximal coronary arteries. Coronary arterial segments with injuries were dissected free of the epicardium. Segments containing lesions were isolated, thereby allowing sufficient tissue to contain uninvolved blood vessel at either end. The foregoing segments, each roughly 2.5 cm in length, were embedded and processed by means of standard plastic embedding techniques. The tissues were subsequently processed and stained with hematoxylin-eosin and elastic-van Gieson techniques.

Low and high power light microscopy were used to make length measurements in the plane of microscopic view by means of a calibrated reticle and a digital microscopy system connected to a computer employing calibrated analysis software.

The severity of vessel injury and the neointimal response were measured by calibrated digital microscopy. The importance of the integrity of the internal elastic lamina is well-known to those skilled in the art. A histopathologic injury score in stented blood vessels has been validated as being closely related to neointimal thickness. This score is related to depth of injury and is as follows: 0 is internal elastic lamina intact; endothelium typically denuded, media compressed but not lacerated; 1 is internal elastic lamina lacerated; media typically compressed but not lacerated; 2 is internal elastic lacerated; media visibly lacerated; external elastic lamina intact but compressed; and 3 is external elastic lamina lacerated: typically large lacerations of media extending through the external elastic lamina; coil wires sometimes residing in adventitia.

This quantitative measurement of injury was assessed for all stent wires of each stent section. The calibrated digital image was also used to measure at each stent wire site the neointimal thickness. Lumen area, area contained with the internal elastic lamina, and area within the external elastic lamina were also measured. The neointimal thickness was measured for each strut in a given section than averaged to determine the neointimal thickness for the section. The mid-stent segment was used for measurement, analysis, and comparison. Data were also recorded (and included in the data section of this report) for proximal and distal segments. The data analysis methods for this study did not need to take into account variable arterial injury across treatment/control groups, because mild to moderate injury is sensitive enough to detect treatment differences. Paired t-testing was performed to compare variables across the polymer only stents (control group) and polymer plus drug stents (treatment group). No animal died in this study before scheduled time-points.

Table 3 shows the pigs and arteries used. In Table 3, LCX means the circumflex branch of the left coronary artery, LAD means the left anterior descending coronary artery, and RCA means the right coronary artery.

TABLE 3

|   | Subject | Arteries Used |
|---|---------|---------------|
| 1 | 2000-G-693 | RCA - Control |
|   |            | LCX - Test |
| 2 | 2000-G-698 | RCA - Test |
|   |            | LAD - Control |
| 3 | 2000-G-702 | RCA - Test |
|   |            | LAD - Control |
| 4 | 2000-G-709 | RCA - Control |
|   |            | LAD - Test |
| 5 | 2000-G-306 | RCA - Control |
|   |            | LAD - Test |
|   |            | *LCX - Test |
| 6 | 2000-G-672 | RCA - Test |
|   |            | LAD - Control |
| 7 | 2000-G-712 | RCA - Control |
|   |            | LCX - Test |

TABLE 3-continued

| | Subject | Arteries Used |
|---|---|---|
| 8 | 2000-G-735 | RCA - Control |
| | | LAD - Test |
| 9 | 2000-G-736 | RCA - Control |
| | | LCX - Test |
| 10 | 2000-G-740 | RCA - Test |
| | | LAD - Control |
| 11 | 2000-G-742 | LAD - Test |
| | | OM (LCX) - Control |
| 12 | 2000-G-744 | RCA - Test |
| | | LAD - Control |
| 13 | 2000-G-748 | RCA - TEst |
| | | LAD - Control |
| 14 | 2000-G-749 | RCA - Control |
| | | LCX - Test |
| 15 | 2000-G-753 | RCA - Control |
| | | LAD - Test |
| 16 | 2000-G-754 | RCA - Test |
| | | LCX - Control |
| 17 | 2000-G-755 | RCA - Control |
| | | LAD - Test |
| 18 | 2000-G-756 | RCA - Test |
| | | LAD - Control |
| 19 | 2000-G-757 | LAD - Control |
| | | LCX - Test |
| 20 | 2000-G-760 | LAD - Test |
| | | LCX - Control |

Table 4 shows the summary results for all data for mean injury and neointimal thickness for each stent, including proximal, mid, and distal segments. Table 4 also shows lumen size, percent stenosis, and artery size as measured by the internal elastic laminae (IEL) and external elastic laminae (EEL).

TABLE 4

Summary: All Measures (Distal, Mid, Proximal)

| | | prox ref | dist ref | lumen | IEL | EEL | mean injury | % Stenosis | Neointimal area | NIT |
|---|---|---|---|---|---|---|---|---|---|---|
| Control | Distal | | | | | | | | | |
| Mean | | 4.46 | 3.96 | 4.88 | 7.66 | 9.00 | 0.22 | 36.10 | 2.79 | 0.41 |
| SD | | 1.20 | 1.16 | 1.30 | 1.15 | 1.10 | 0.26 | 15.41 | 1.29 | 0.17 |
| Control | Mid | | | | | | | | | |
| Mean | | 4.46 | 3.96 | 4.94 | 7.71 | 9.08 | 0.08 | 36.23 | 2.77 | 0.38 |
| SD | | 1.20 | 1.16 | 1.44 | 1.07 | 1.15 | 0.14 | 14.93 | 1.20 | 0.16 |
| Control | Proximal | | | | | | | | | |
| Mean | | 4.46 | 3.96 | 5.11 | 7.89 | 9.30 | 0.15 | 35.35 | 2.78 | 0.38 |
| SD | | 1.20 | 1.16 | 1.38 | 1.33 | 1.42 | 0.22 | 11.94 | 1.04 | 0.12 |
| Test | Distal | | | | | | | | | |
| Mean | | 4.26 | 3.41 | 6.04 | 7.70 | 9.01 | 0.26 | 22.35 | 1.66 | 0.25 |
| SD | | 1.26 | 0.96 | 1.55 | 1.49 | 1.47 | 0.43 | 8.58 | 0.58 | 0.06 |
| Test | Mid | | | | | | | | | |
| Mean | | 4.26 | 3.41 | 6.35 | 7.75 | 8.98 | 0.04 | 18.71 | 1.41 | 0.22 |
| SD | | 1.26 | 0.96 | 1.29 | 1.18 | 1.31 | 0.07 | 5.68 | 0.33 | 0.05 |
| Test | Priximal | | | | | | | | | |
| Mean | | 2.56 | 2.15 | 3.31 | 4.06 | 4.66 | 0.19 | 16.79 | 1.29 | 0.18 |
| SD | | 1.66 | 1.37 | 2.39 | 3.48 | 4.15 | 0.13 | 9.97 | 0.80 | 0.12 |

There was no statistically significant difference for neointimal area or thickness across proximal, mid, or distal segments within the test group (polymer plus drug stents) or control groups (polymer only stents). This observation is quite consistent with prior studies, and thus allows use of only the mid segment for statistical comparison of test devices (polymer plus drug stems) vs. control devices (polymer only stents).

Table 5 shows the statistical t-test comparisons across test groups and control groups. There was a statistically significant difference in neointimal thickness, neointimal area, lumen size, and percent lumen stenosis, the drug eluting stent being clearly favored. Conversely, there were no statistically significant differences between the test group (polymer plus drug stents) and the control group (polymer only stents) for mean injury score, external elastic laminae, or internal elastic laminae areas.

TABLE 5

Statistical Comparison of Test vs. Control Parameters:
Mid-Section Data t-test Statistics

| Parameter | Difference | t-test | DF | Std Error | Lower 95% | Upper 95% | p |
|---|---|---|---|---|---|---|---|
| Lumen | −1.17 | −2.28 | 38 | 0.52 | −2.21 | −0.13 | 0.029 |
| IEL | 0.03 | 0.088 | 38 | 0.36 | −0.71 | 0.78 | 0.93 |
| EEL | 0.2 | 0.499 | 38 | 0.39 | −0.599 | 0.99 | 0.62 |
| NI Thickness | 0.18 | 5.153 | 38 | 0.034 | 0.106 | 0.244 | <.0001 |
| NI Area | 1.21 | 3.62 | 38 | 0.33 | 0.53 | 1.88 | 0.0008 |
| Mean Injury | 0.038 | 1.137 | 38 | 0.033 | −0.02 | 0.106 | 0.26 |
| % Stenosis | 14.54 | 2.97 | 38 | 4.9 | 4.61 | 24.47 | 0.005 |

The reference arteries proximal and distal to the stented segments were observed, and quantitated. These vessels appeared normal in all cases, uninjured in both the control group (polymer only stents) and the test group (polymer plus drug stents). The data of Table 6 show there were no statistically significant differences in size between the stents in the control group and the stents in the test group.

TABLE 6

|  | Proximal Reference Diameter (mm) | Distal Reference Diameter (mm) |
|---|---|---|
| Control (mean ± SD) | 4.46 ± 1.20 | 3.96 ± 1.16 |
| Test (mean + SD) | 4.26 ± 1.26 | 3.41 ± 0.96 |

The data suggest that statistically significant differences exist, and these differences favor the stent that elutes A-179578. The stent of this invention results in lower neointimal area, lower neointimal thickness, and greater lumen area. There were no significant differences within the test group (polymer plus drug stents) and the control group (polymer only stents) for neointimal or injury parameters. There were no significant differences in artery sizes (including the stent) for the control group compared to the test group. These latter findings suggest no significant difference in the arterial remodeling characteristics of the polymeric coating containing the drug.

At most, mild inflammation was found on both the polymer plus drug stent and the polymer only stent. This finding suggests that the polymer exhibits satisfactory biocompatibility, even without drug loading. Other studies show that when the drug has completely gone from the polymer, the polymer itself creates enough inflammation to cause neointima. This phenomenon may be responsible for the late "catch-up" phenomenon of clinical late restenosis. Because the polymer in this example did not cause inflammation in the coronary arteries, late problems related to the polymer after the drug is exhausted are unlikely.

In conclusion, a stent containing the compound A-179578 with a polymer showed a reduction in neointimal hyperplasia in the porcine model when placed in a coronary artery.

Example 4

The purpose of this example is to determine the rate of release of the A-179578 (ABT-578) drug from 316 L Electropolished Stainless Steel Coupons coated with a biocompatible polymer containing phosphorylcholine side groups.

Rubber septa from lids from HPLC vials were removed from the vials and placed into glass vials so that the "Teflon" side faced up. These septa served as supports for the test samples. The test samples were 316 L, stainless steel coupons that had been previously coated with a biocompatible polymer containing phosphorylcholine side groups (PC polymer). Coronary stents are commonly made of 316 L stainless steel and can be coated with the PC polymer to provide a depot site for loading drugs. The coated coupons, which serve to simulate stents, were placed onto the septa. By using a glass Hamilton Syringe, a solution of A-179578 and ethanol (10 µl) was applied to the surface of each coupon. The solution contained A-179578 (30.6 mg) dissolved in 100% ethanol (3.0 ml). The syringe was cleaned with ethanol between each application. The cap to the glass vial was placed on the vial loosely, thereby assuring proper ventilation. The coupon was allowed to dry for a minimum of 1.5 hours. Twelve (12) coupons were loaded in this way, six being used to determine the average amount of drug loaded onto the device and six being used to measure the time needed to release the drug from the devices.

To determine the total amount of ABT-578 loaded onto a coupon, a coupon was removed from the vial and placed into 50/50 acetonitrile/0.01M phosphate buffer (pH 6.0, 5.0 ml). The coupon was placed onto a 5210 Branson sonicator for one hour. The coupon was then removed from the solution, and the solution was assayed by HPLC.

The time release studies were performed by immersing and removing the individual coupons from fresh aliquots (10.0 ml) of 0.01 M phosphate buffer at a pH of 6.0 at each of the following time intervals; 5, 15, 30 and 60 minutes. For the remaining time points of 120, 180, 240, 300, 360 minutes, volumes of 5.0 ml of buffer were used. To facilitate mixing during the drug release phase, the samples were placed onto a Eberbach shaker set at low speed. All solution aliquots were assayed by HPLC after the testing of the last sample was completed.

The HPLC analysis was performed with a Hewlett Packard series 1100 instrument having the following settings: Injection Volume is 100 µl; Acquisition Time is 40 minutes; Flow Rate is 1.0 ml/min; Column Temperature is 40 degrees Celsius; Wavelength is 278 nm; Mobile Phase is 65% Acetonitrile/35% $H_2O$; and Column is YMC ODS-A S5 µm, 4.6×250 mm (Part No. Al2052546WT).

The results from the above experiment showed the release data shown in Table 7.

TABLE 7

| Time (min.) | Percent Release | Standard Deviation |
|---|---|---|
| 0.00 | 0.00 | 0.00 |
| 5.00 | 1.87 | 1.12 |
| 15.00 | 2.97 | 1.47 |
| 30.00 | 3.24 | 1.28 |
| 60.00 | 3.29 | 1.29 |

TABLE 7-continued

| Time (min.) | Percent Release | Standard Deviation |
|---|---|---|
| 120.00 | 3.92 | 1.28 |
| 180.00 | 4.36 | 1.33 |
| 240.00 | 4.37 | 1.35 |
| 300.00 | 6.34 | 2.07 |
| 360.00 | 7.88 | 1.01 |

Example 5

The purpose of this example was to determine the loading and release of ABT-578 from 15 mm BiodivYsio drug delivery stems. To load the stents with drug, a solution of ABT-578 in ethanol at a concentration of 50 mg/ml was prepared and dispensed into twelve vials. Twelve individual polymer-coated stents were placed on fixtures designed to hold the stent in a vertical position and the stents were immersed vertically in the drug solution for five minutes. The stents and fixtures were removed from the vials and excess drug solution was blotted away by contacting the stents with an absorbant material. The stents were then allowed to dry in air for 30 minutes in an inverted vertical position.

The stents were removed from the fixtures, and each stent was placed into 50/50 acetonitrile/phosphate buffer (pH 5.1, 2.0 ml) and sonicated for one hour. The stems were removed from the solution and solutions were assayed for concentration of drug, which allowed calculation of the amount of drug originally on the stents. This method was independently shown to remove at least 95% of the drug from the stent coating. On average, the stents contained 60 micrograms of drug±20 micrograms.

The drug-loaded stents were placed on the fixtures and placed into 0.01 M phosphate buffer (pH=6.0, 1.9 ml) in individual vials. These samples were placed onto an Eberbach shaker set at low speed to provide back-and-forth agitation. To avoid approaching drug saturation in the buffer, the stents were transferred periodically to fresh buffer vials at the following points: 15, 30, 45, 60, 120, 135, 150, 165, 180, 240, 390 minutes. The dissolution buffer vials were assayed by HPLC for the drug concentration at the end of the drug release period studied. The data, represented as % cumulative release of the drug as a function of time, is shown in tabular form below:

TABLE 8

| Time (min) | % Cumulative Release of Drug |
|---|---|
| 15 | 0.3 |
| 30 | 1.1 |
| 45 | 2.1 |
| 60 | 3.2 |
| 120 | 4.3 |
| 135 | 5.9 |
| 150 | 6.3 |
| 165 | 6.8 |
| 180 | 7.4 |
| 240 | 10.8 |
| 390 | 13.2 |

Example 6

The purpose of this example was to evaluate the safety and efficacy of different drug dosages on neointima formation. Drug was delivered from the BiodivYsio OC stent (15 mm) coated with AST-578. In-stent neointima formation was measured at four time intervals; 3 days, 1 month, and 3 months in the coronary arteries of adult miniature swine. Forty (40) animals were studied at each time interval (10 animals per dose). Each animal received one drug-coated stent and one control stent. The control stent contained no drug. Table 9 shows the dosing scheme for swine efficacy study.

TABLE 9

| | Dose group 1 (µg) | Dose group 2 (µg) | Dose Group 3 (µg) | Dose group 4 (µg) |
|---|---|---|---|---|
| ABT-578 per stent | 15 | 45 | 150 | 400 |
| ABT-578 per mm of stent | 1 | 3 | 10 | 27 |

Potential local tissue toxicity was assessed at all time intervals by examining histopathologic changes in the stented region, adjacent coronary segments, perivascular tissue, and subserved myocardium. The mortality, angiographic implant and restudy data, histomorphometry data, and stent site histopathology were studied.

Three-Day Group:

Histopathology in combination with scanning electron microscopy provided information regarding the short-term response to the implanted stent. The responses were similar in the control group and all dose groups, and the responses involved compression of the tunica media without remarkable necrosis, an accumulation of thrombus and inflammatory cells mostly localized to the stent struts, and early evidence of endothelial recovery and smooth muscle cell invasion of the thin mural thrombi. There were no extensive thrombi or remarkable intramural hemorrhages. The adventitia in some samples displayed either focal or diffuse inflammatory infiltrates, and occasionally there was plugging or congestion of the vasa vasora. There was no evidence of medial necrosis in any sample.

Scanning electron microscopy showed similar appearance of the luminal surface three days after the implant of the coronary stent in all dose groups. The shape of the stent was clearly embedded in a thin layer of tissue. The endothelium was intact between the struts and even over the struts; a confluent or nearly confluent layer of endothelial-like cells had covered the luminal surface. There were scattered adherent platelets, platelet microthrombi, and leukocytes over the stents and on the intact remnant endothelium in the inter-strut spaces. In arteries with more severe stent-induced vessel damage, there were more substantial mural thrombi, but the extent of endothelial recovery over the stent struts did not appear retarded, regardless of the dosage of ABT-578.

One-Month Group:

The histomorphometry data for the one-month series indicated a significant inhibitory effect of locally eluted ABT-578 on neointima formation in stented coronary arteries of swine. Intima area normalized to injury score was significantly decreased for dose groups 3 and 4 (10 and 27 µg/mm) as compared with the control; there were also trends for decreases in absolute intima area and intima thickness for both dose groups 3 and 4 as compared with the control, and a tendency towards decreased histologic % stenosis for dose group 3 as compared with the control.

The control stents displayed morphology typical of stents implanted in coronary arteries of Yucatan miniature swine at one month. The tunica media was compressed or thinned without necrosis subjacent to profiles of stent struts; there were only occasional inflammatory infiltrates; and the neointima ranged in size from relatively thin to moderately thin, and were composed of spindle-shaped and stellate cells in an abundant extracellular matrix, with only rare small foci of fibrinoid material around the profiles of the stent struts. The drug-coated stents showed similar compression of the tunica media without any substantial necrosis at any dose; like control devices, there was little inflammation present. The neointima was notably thinner in dose groups 3 and 4, in some cases being composed of only a few layers of cells. In all dose groups, there were substantial numbers of samples in which moderately sized fibrinoid deposits and inspissated thrombi were observed in the deep neointima. These were usually associated with the stent struts but sometimes extended between strut profiles. However, in no case was there exposure of thrombus on the luminal surface, as the deposits were encapsulated within fibrocellular tissue and covered with a flattened layer of periluminal endothelial-like cells.

Scanning electron microscopy confirmed that a confluent layer of endothelial or endothelial-like cells covered the entire stented surface, and there was no difference between drug-coated stents and control stents in terms of adherence of blood elements; leukocytes were present in approximately equal numbers in all groups. These findings demonstrate that while ABT-578 was associated with decreased neointima formation and persistent mural thrombi, sufficient vessel wall healing in response to stent injury had occurred within one month after the stent had been implanted. This vessel wall healing had rendered the luminal surface non-reactive for platelet adhesion and thrombus formation, and minimally reactive for leukocyte adherence. Additionally, there was no evidence of vessel wall toxicity even at the highest dose (27 μg/mm), as there was no medial necrosis or stent malapposition.

Three-Month Group:

There were no significant differences between the dose groups for any histomorphometric parameters of stented coronary arterial dimension in the three-month period of the study. However, there were weak trends for decreases in the two primary variables describing neointima formation; the cross-sectional area and the % area stenosis of the lumen.

The histopathologic appearance of the control stents in the swine coronary artery samples at three months after the implant appeared similar to that of the controls from the one-month group, and similar to those of all the groups in the three-month period. All samples showed fibrocellular neointima formation with mostly spindle-shaped smooth muscle-like cells in the neointima and a confluent squamous periluminal cell layer. There were no intramural hemorrhages or persistent fibrinoid deposits in the neointima; however some samples, particularly those with thicker neointima, showed evidence of prior thrombus accumulation and subsequent organization in the form of neovascularization in the neointima. On occasion, samples showed evidence of moderate to severe inflammatory reactions localized to the stent struts, associated with destruction of the tunica media architecture. These were most often associated with thicker neointima as well. However, these were few in number and were found in the control group as well as in the drug-coated stent groups. It is presumed that these represented either animal-specific generalized reactions to the implanted stent, evidence of contamination of the stent, or some combination of these two factors, and is commonly found at an incidence of about 10-15% in the studies of stem implants in swine coronary arteries. There was no evidence of necrosis of the tunica media or separation of the media from the stent in any sample. The adventitia of most three-month implants appeared to have somewhat greater neovascularization than did the one-month implants, but this did not appear related to control or test stent group. Scanning electron microscopy demonstrated confluent endothelium with rare adherent blood cells in the control group and all dose groups.

The stent coated with ABT-578 reduced in-stent neointima formation in swine coronary arteries and provided clear evidence of a biologic drug effect (unresorbed thrombus/fibrin deposits of neointima) at one month. There was a weak tendency for the stent coated with ABT-578 to show a persistent inhibitory effect at the longer-term time interval of three months. There was no local coronary arterial wall toxicity in the form of medial necrosis or stent malapposition associated with any dose group, including the highest dose of approximately 27 μg/mm stent length at any time interval examined. All stents were well incorporated into the tissue, and there was evidence of stable healing responses in the form of fibrocellular neointimal incorporation and endothelial coverage at the one-month interval and at the three-month interval. The trend towards a sustained inhibitory effect at three months after the stent was implanted in this animal is surprising and provides evidence for potentially persistent effects in preventing clinical restenosis resulting from implanted stents.

Example 7

Rapamycin analog crystals were prepared by crystallizing the analog in a biphasic mixture. Briefly, ABT-578 was added to a vial containing 0.23 g acetone and 0.82 g heptane and incubated at 0 degrees Celsius so as to saturate the liquid phase. The mixture was incubated until a liquid-liquid phase split occurred as ABT-578 dissolved into the acetone solution resulting in an ABT-578-acetone rich bottom phase and a heptane rich top phase. The biphasic mixture was incubated at 0 degrees Celsius for 10 days at which rapamycin analog crystals were observed at the bottom of the vial. FIG. 2A shows the powder X-ray diffraction (PXRD) patterns.

The acetone solvate was analyzed for pertinent crystallographic information, which is included in Table 10. It was determined that the solvent molecules along the c-axis separate the ABT-578 molecules. The solvent molecules are fairly disordered, but it appears as if there are four acetones, and two water molecules per ABT-578. ABT-578 molecules interact via Van der Waal's interactions along the a- and b-axes.

TABLE 10

| Acetone Solvate Crystallographic Information | |
|---|---|
| Parameter | ABT-578 |
| Crystal System | Orthorhombic |
| Space group | $P2_12_12_1$ |
| a, Å | 12.245 |
| b, Å | 17.401 |
| c, Å | 33.356 |
| Volume, (Å$^3$) | 7107 |
| $\rho_{calc}$ (g/cm$^3$) | 1.120 |

Example 8

Crystals of ABT-578 toluene solvate were generated by the following procedure. A clear solution was prepared by dissolving 100 mg of amorphous ABT-578 in 300 mg toluene. The solution was stirred at 22 degrees Celsius for 15 hours upon which a thick slurry of crystalline solids was observed. FIG. 4A shows the powder X-ray diffraction pattern of toluene solvate crystals prepared using solids from the above preparation as seeds.

Example 9

Figure 6C:
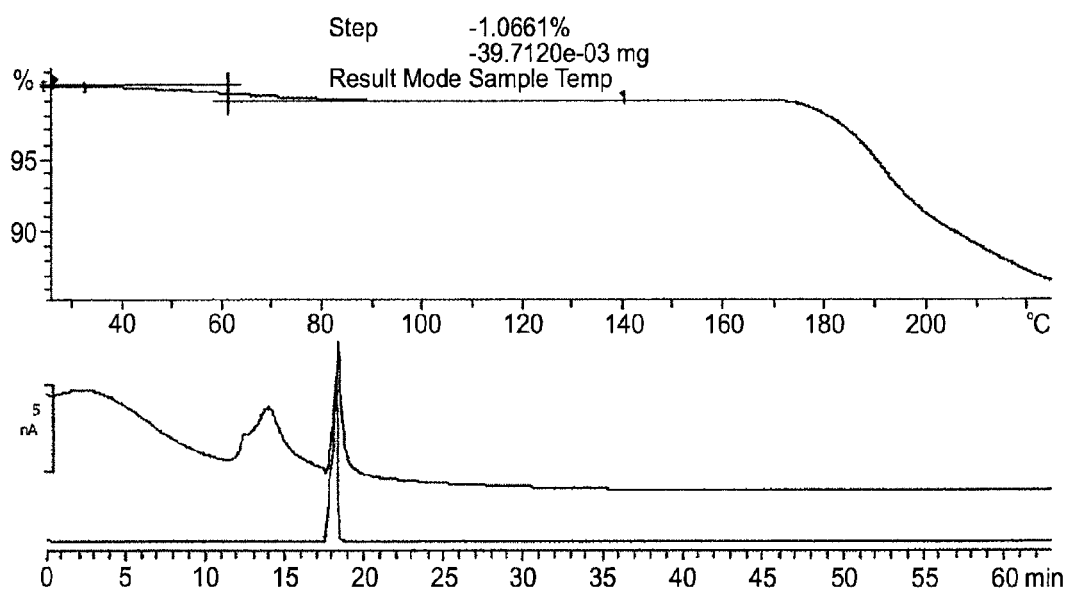
FIG. 6C is a graph illustrating a thermogravimetric analysis of an embodiment of a crystalline form of a rapamycin analog acetonitrile desolvate.

Crystals of ABT-578 acetonitrile desolvated solvate were generated by saturating acetonitrile with amorphous ABT-578 at 22 degrees Celsius, and then incubating the saturated solution at 0 degrees Celsius for 2 hours. FIG. 5A shows the powder X-ray diffraction pattern of the crystals. The crystals can then be dried to form an acetonitrile desolvate, and FIG. 6C shows the thermogravimeric analysis data for the desolvate.

Example 10

Figure 7C:
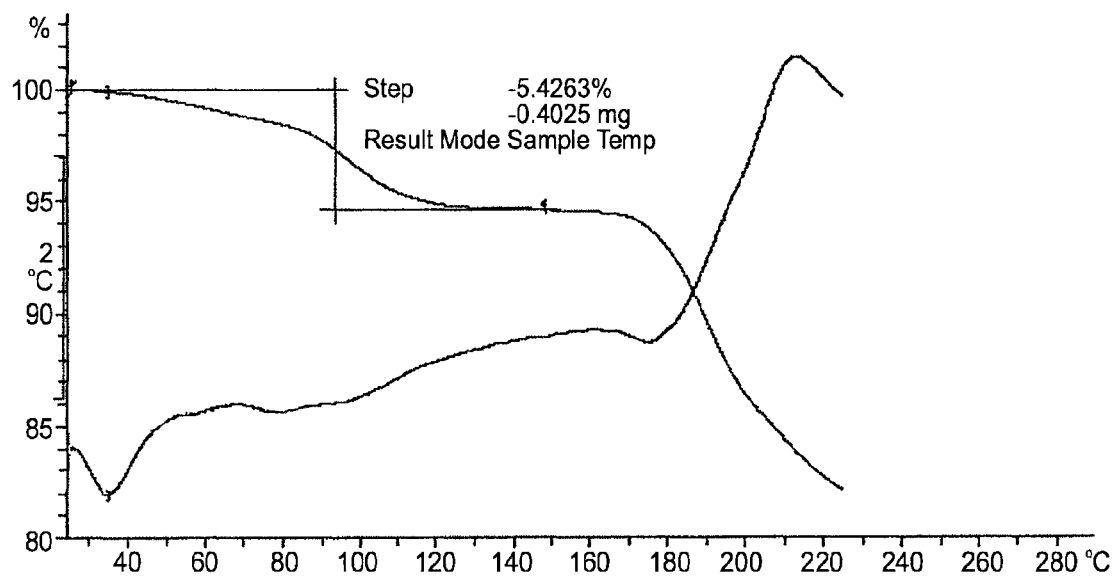
FIG. 7C is a graph illustrating a thermogravimetric analysis of an embodiment of a crystalline form of a rapamycin analog ethyl formate solvate.

Crystals of ABT-578 ethyl formate solvate were generated by slurrying a wetcake of acetonitrile solvate in ethyl formate at 0 degrees Celsius. FIGS. 7A and 7C show the powder X-ray diffraction pattern and thermogravimeric analysis of the crystals, respectively.

Example 11

Crystals of ABT-578 isopropyl acetate solvate were generated by slurrying a wetcake of acetonitrile solvate in isopropyl acetate at 0 degrees Celsius.

Example 12

Figure 9B:
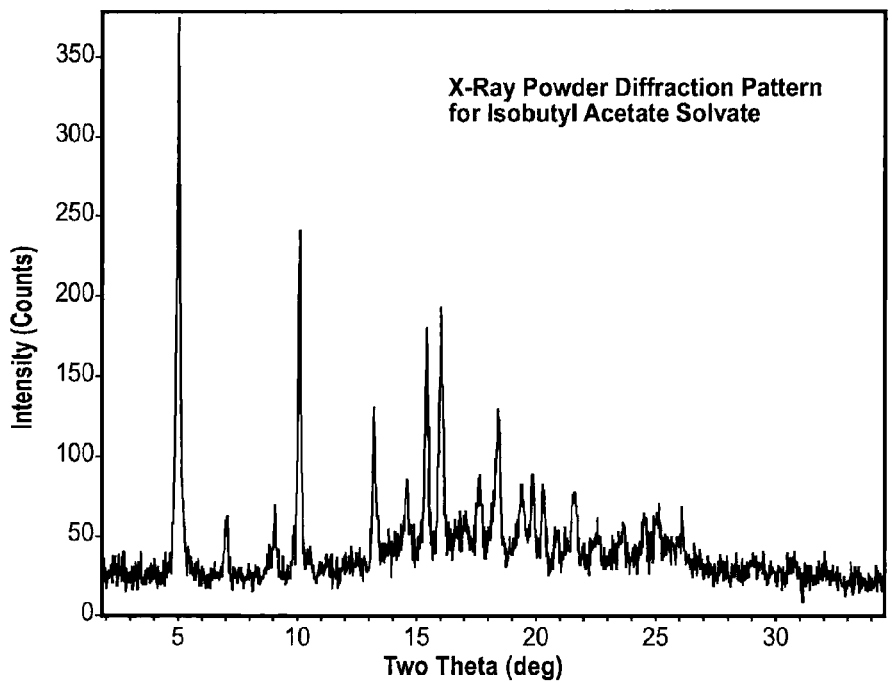
FIG. 9B is a graph illustrating a powder X-ray diffraction pattern of an embodiment of a crystalline form of a rapamycin analog isobutyl acetate solvate.
Figure 9C:
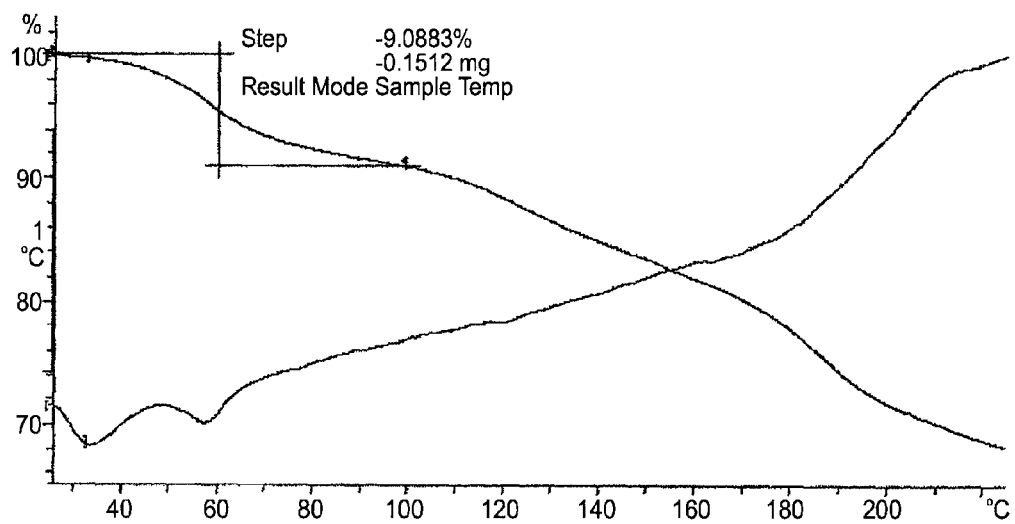
FIG. 9C is a graph illustrating a thermogravimetric analysis of an embodiment of a crystalline form of a rapamycin analog isobutyl acetate solvate.

Crystals of ABT-578 were prepared by adding 380 mg amorphous ABT-578 to a vial and charging 870 mg isobutyl acetate to it to enable dissolution. This was incubated at 0 degrees Celsius for 16 hours upon which a crystalline slurry was obtained. FIGS. 9A and 9C show the powder X-ray diffraction pattern and thermogravimeric analysis of the crystals, respectively.

Example 13

Crystals of ABT-578 ethanol solvate were prepared by adding 417 mg amorphous ABT-578 to a vial and charging 315 mg ethanol 200 proof to it to enable dissolution. This was seeded after 15 hours with the acetonitrile desolvated solvate and incubated at 0 degrees Celsius for an additional 16 hours upon which a crystalline slurry was obtained.

Example 14

Figure 10B:
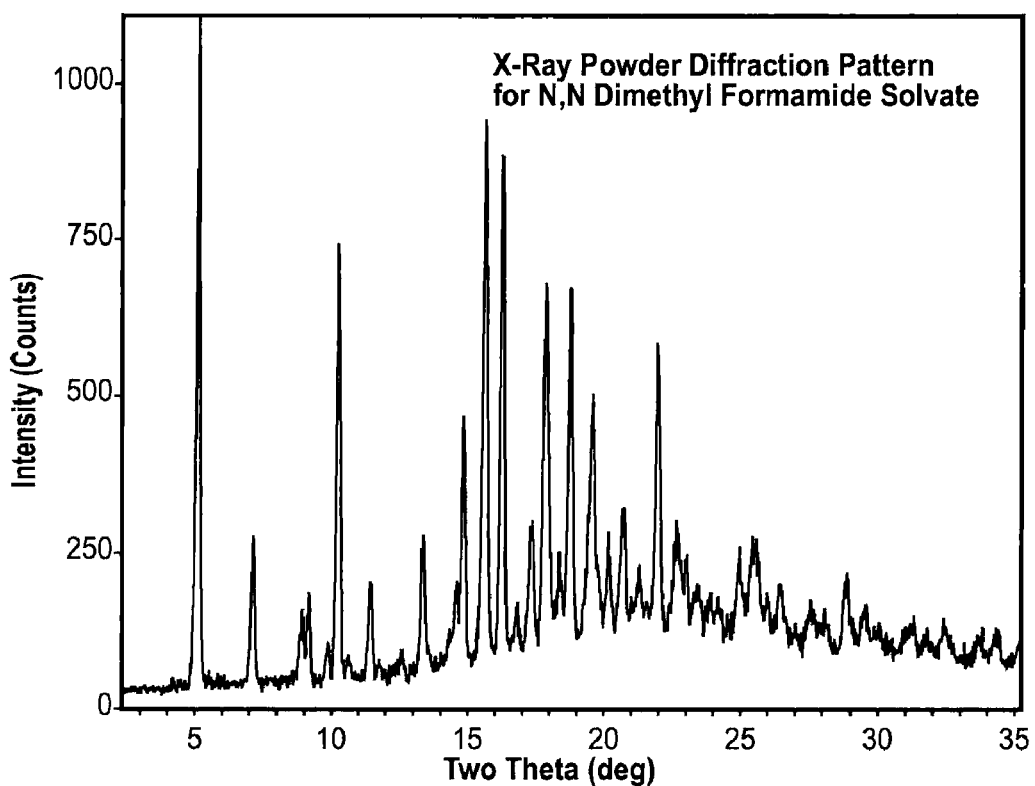
FIG. 10B is a graph illustrating a powder X-ray diffraction pattern of an embodiment of a crystalline form of a rapamycin analog N,N-dimethyl formamide solvate.
Figure 10C:
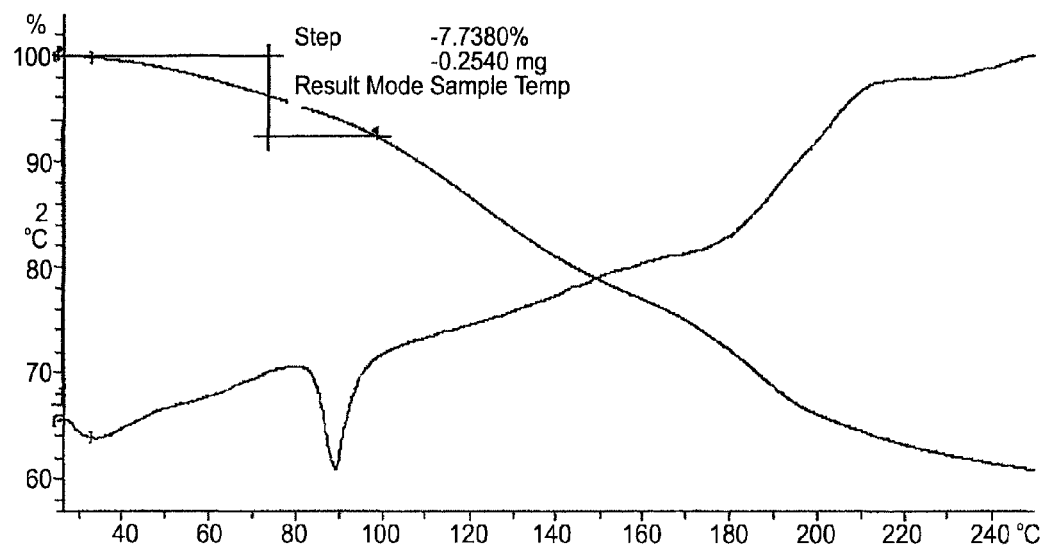
FIG. 10C is a graph illustrating a thermogravimetric analysis of an embodiment of a crystalline form of a rapamycin analog N,N-dimethyl formamide solvate.

Crystals of ABT-578 N,N dimethyl formamide solvate were generated by slurrying a wetcake of acetonitrile solvate in N,N dimethyl formamide at 0 degrees Celsius. FIGS. 10A and 10B show the powder X-ray diffraction pattern and thermogravimeric analysis of the crystals, respectively.

Example 15

Figure 11B:
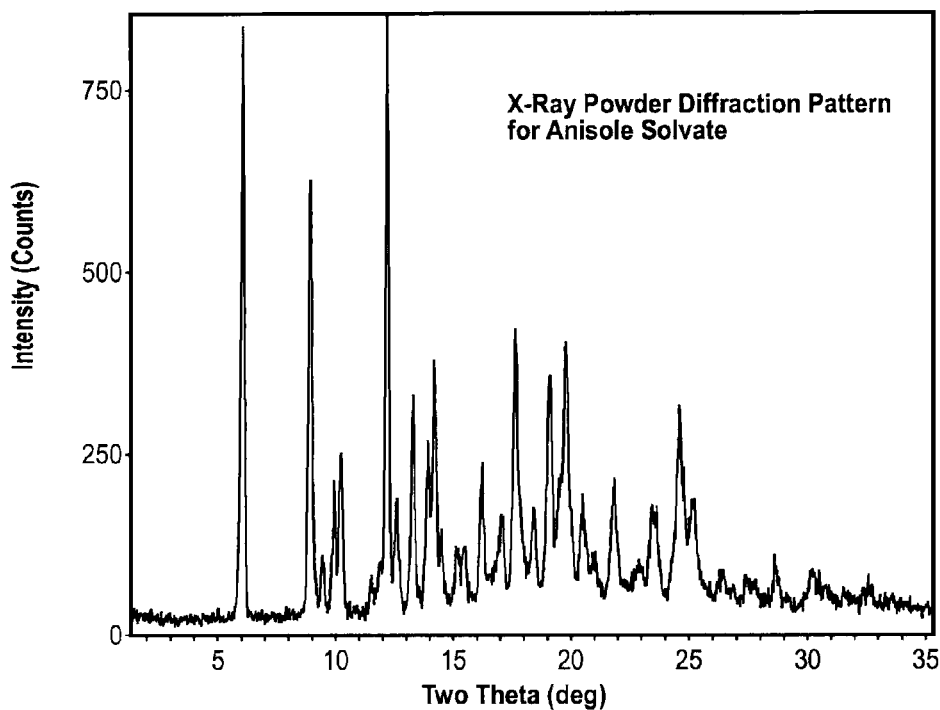
FIG. 11B is a graph illustrating a powder X-ray diffraction pattern or an embodiment of a crystalline form of a rapamycin analog anisole solvate.
Figure 11C:
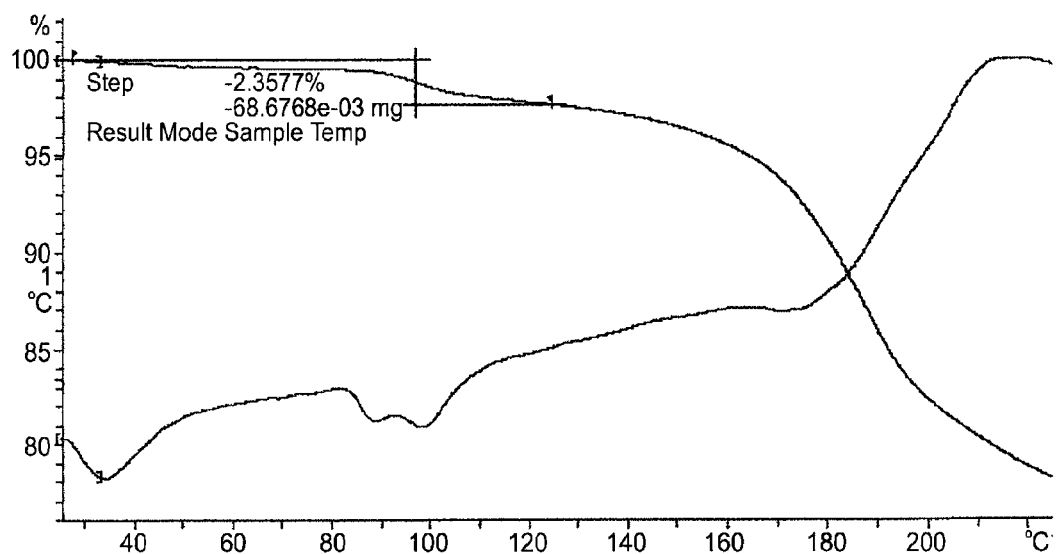
FIG. 11C is a graph illustrating a thermogravimetric analysis of an embodiment of a crystalline form of a rapamycin analog anisole solvate.

Crystals of ABT-578 anisole solvate were generated by slurrying a wetcake of acetonitrile solvate in anisole at 0 degrees Celsius. FIGS. 11A and 11C show the powder X-ray diffraction pattern and thermogravimeric analysis of the crystals, respectively.

Example 16

A crystalline rapamycin analog in the form of acetone solvate was prepared by dissolving approximately 120 mg of amorphous rapamycin analog in 200 uL of acetone at ambient temperature and incubating the resulting solution at 5 degrees Celsius for 14 hours or until crystalline solids are observed in a crystalline slurry. The crystals were analyzed by powder X-ray diffraction, which is shown in FIG. 2B. The crystals were equilibrated at ambient temperature followed by further drying at 30 degrees Celsius under vacuum (approximately 3 inches of mercury). The dried crystals were then analyzed by powder X-ray diffraction, which is shown in FIG. 3B.

Example 17

A crystalline rapamycin analog in the form of a toluene solvate was prepared by dissolving approximately 220 mg of amorphous rapamycin analog in approximately 400 uL of toluene at 45 degrees Celsius to form a solution. The solution was incubated at 5 degrees Celsius for about 1 hour or until crystalline solids can be observed. FIG. 4B is the diffraction pattern of the toluene solvate. A diffraction pattern of a desolvated toluene solvate is shown in FIG. 4E. The desolvated crystals were obtained by allowing solvate crystals equilibrate at ambient temperature followed by further drying at 30 degrees Celsius under vacuum (approximately 3 inches of mercury).

The loss of toluene upon heating can be described in 3 stages. The first stage loss of toluene is at temperature below 90 degrees Celsius. The second stage is at temperatures from 90 degrees Celsius to 130 degrees Celsius, and the last stage is after melting, >150 degrees Celsius. Therefore, the crystalline desolvated toluene solvate obtained by drying is a partially desolvated product. The X-ray single crystal structure of toluene solvate has been determined. The crystallographic information is listed in Table 11.

TABLE 11

Crystallographic Information of ABT-578 Toluene Solvate

| | ABT-578 toluene solvate |
|---|---|
| T/K | 293 |
| Space group | $P2_1$ |
| Crystal system | Monoclinic |
| a/Å | 17.649(5) |
| b/Å | 12.299(3) |
| c/Å | 17.785(4) |
| β/° | 113.518(4) |
| V/Å$^3$ | 3539.83 |
| Z | 2 |
| $\rho_{calc}$/g cm$^{-3}$ | 1.138 |

Figure 4F:
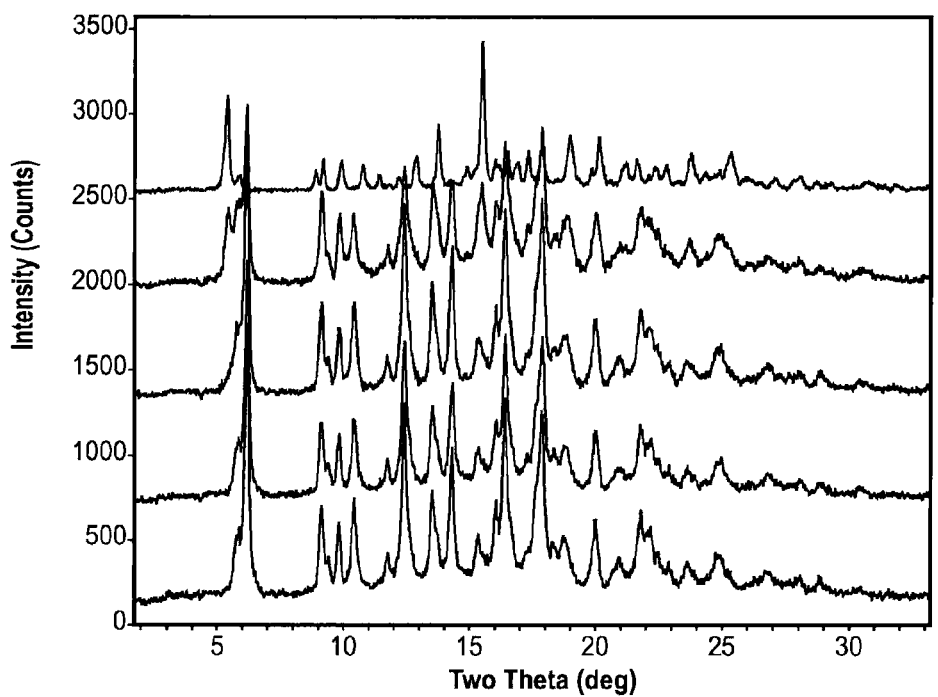
FIG. 4F is a graph showing the change in powder X-ray diffraction patterns during the desolvation of the rapamycin analog toluene solvate of FIG. 4B.

The ABT-578 toluenate crystallizes in $P2_1$ chiral space group, and there are two ABT-578 molecules in each unit cell. FIG. 4C shows the X-ray single crystal structure of ABT-578 toluene solvate, which was obtained using molybdenum-k alpha radiation (0.070930). As can be seen from the structure, in each asymmetric unit of the crystal, there are three toluene molecules and one Zotarolimus molecule. So the toluene solvate is a tri-toluenate. Among the three toluene molecules ($T_a$, $T_b$, and $T_c$), $T_a$ and $T_b$ have short contacts with ABT-578 molecule (i.e. C—H•••π and C=O•••H—C=C interactions). $T_c$ interacts with surrounding molecules only via weak Van der Waal's force. Interestingly, in the toluene solvate crystal structure there are solvent channels alone the b axis, as shown in FIG. 4D. Toluene molecules $T_a$ and $T_c$ are more exposed in the channel and are expected to remove relatively easily from the crystals. On the other hand, toluene molecule $T_b$ is semi-trapped in a cavity surrounded by ABT-578 molecules. Therefore, for these three different toluene molecules, $T_b$ binds tightly, $T_a$ binds moderately tightly, and $T_c$ binds loosely to ABT-578 molecules. This explains the fact that the toluene solvate shows staged loss of toluene upon drying/ heating and that complete removal of toluene from the crystals is difficult to achieve. It also explains the crystal lattice shrinkage along a axis upon drying as evidenced by the PXRD pattern change of desolvation of toluene solvate, as shown in FIG. 4F.

Example 18

A crystalline rapamycin analog in the form of an acetonitrile solvate was prepared by dissolving approximately 100 mg of amorphous rapamycin analog in 200 uL of acetonitrile at 45 degrees Celsius and incubating at about −12 degrees Celsius for about 30 hours after which the solution was seeded with a trace amount of toluene solvate crystals. Crystalline solids formed after seeding by further incubation at −12 degrees Celsius. The crystals can then be analyzed by powder X-ray diffraction, which is shown by FIG. 5B. The crystals were equilibrated at ambient temperature followed by further drying at 30 degrees Celsius under vacuum (approximately 3 inches of mercury). The dried crystals can be analyzed by powder X-ray diffraction, which is shown in FIG. 6B.

Example 19

A crystalline rapamycin analog in the form of an ethyl formate solvate was prepared by dissolving approximately 100 mg of amorphous rapamycin analog in 200 uL of ethyl formate at 45 degrees Celsius and incubating at about 5 degrees Celsius for about 14 hours or until crystals form. FIG. 7B is the diffraction pattern of the ethyl formate solvate. The ethyl formate desolvated diffraction pattern is shown by FIG. 8. The desolvated crystals were obtained by allowing solvate crystals equilibrate at ambient temperature followed by further drying at 30 degrees Celsius under vacuum (approximately 3 inches of mercury).

Example 20

A crystalline rapamycin analog in the form of an isopropyl acetate solvate was prepared by dissolving approximately 100 mg of amorphous rapamycin analogue in approximately 200 uL of isopropyl acetate at ambient temperature. The solution was incubated at 5 degrees Celsius for 14 hours or until crystalline solids were observed. The isopropyl acetate solvate diffraction pattern is shown by FIG. 17A. The desolvated crystals were obtained by allowing solvate crystals equilibrate at ambient temperature followed by further drying at 30 degrees Celsius under vacuum (approximately 3 inches of mercury). FIG. 17B shows the X-ray powder diffraction patterns of the desolvated solvate.

Example 21

A crystalline rapamycin analog, in the form of an isobutyl acetate solvate was prepared by adding approximately 400 mg of amorphous rapamycin analog to a vial and charging approximately 870 mg of isobutyl acetate into the vial to enable dissolution at ambient temperature. The solution was then be incubated at about 0 degrees Celsius for about 16 hours or until a crystalline slurry was obtained. The crystals were then analyzed by powder X-ray diffraction, which is shown by FIG. 9B.

Example 22

A crystalline rapamycin analog in the form of an ethanol solvate was prepared by dissolving approximately 100 mg of amorphous rapamycin analog in 400 μL of ethanol (200 proof) at 45 degrees Celsius and incubating at approximately 5 degrees Celsius for 14 hours or until crystals form. FIG. 12A is the diffraction pattern of the solvate. The desolvated crystals were obtained by allowing solvate crystals equilibrate at ambient temperature followed by further drying at 30 degrees Celsius under vacuum (approximately 3 inches of mercury). FIG. 12B shows the X-ray powder diffraction patterns of the desolvated solvate.

Example 23

Crystals of ABT-578 methanol solvate were prepared by dissolving 93 mg of amorphous ABT-578 in 200 uL of methanol at ambient temperature and storing at −12 degrees Celsius for 30 hours before seeded with a trace amount of toluene solvate crystals. Crystalline solids formed after seeding by further incubation at −12 degrees Celcius. FIGS. 13A and 13B show the X-ray powder diffraction patterns of the solvate crystals and the desolvated solvate, respectively. The desolvated crystals were obtained by allowing solvate crytals equilibrate at ambient temperature followed by further drying at 30 degrees Celsius under vacuum (approximately 3 inches of mercury).

Example 24

Crystals of ABT-578 ethyl acetate solvate were prepared by dissolving 103 mg of amorphous ABT-578 in 200 uL of ethyl acetate at ambient temperature and storing at −12 degrees Celsius for 30 hours before seeded with a trace amount of toluene solvate crystals. Crystalline solids formed after seeding by further incubation at −12 degrees Celsius. FIGS. 14A and 14B show the X-ray powder diffraction patterns of the solvate crystals and the corresponding desolvated solvate, respectively. The desolvated crystals were obtained by allowing solvate crystals equilibrate at ambient temperature followed by further drying at 30 degrees Celsius under vacuum (approximately 3 inches of mercury).

Example 25

Crystals of ABT-578 methyl isopropyl ketone solvate were prepared by dissolving 96 mg of amorphous ABT-578 in 200 uL of methyl isopropyl ketone at ambient temperature and storing at −12 degrees Celsius for 30 hours before seeded with a trace amount of toluene solvate crystals. Crystalline solids formed after seeding by further incubation at −12 degrees Celsius. FIGS. 15A and 15B show the X-ray powder diffraction pattern of the solvate crystals and the corresponding desolvated solvate, respectively. The desolvated crystals were obtained by allowing solvate crystals equilibrate at ambient temperature followed by further drying at 30 degrees Celsius under vacuum (approximately 3 inches of mercury).

Example 26

Crystals of ABT-578 nitromethane solvate were prepared by dissolving 100 mg of amorphous ABT-578 in 200 uL of nitromethane at ambient temperature and storing at −12 degrees Celsius for 30 hours before seeded with a trace amount of toluene solvate crystals. Crystalline solids formed after seeding by further incubation at −12 degrees Celsius. Nitromethane solvate of ABT-578 desolyated easily at ambient temperature and appeared as a semi-crystalline phase in the X-ray powder diffraction pattern analysis (FIG. 16).

Example 27

Crystals of ABT-578 propionitrile solvate were prepared by dissolving 108 mg of amorphous ABT-578 in 200 uL of propionitrile at 45 degrees Celsius and storing at −12 degrees Celsius for 30 hours before seeded with a trace amount of toluene solvate crystals. Crystalline solids formed after seeding by further incubation at −12 degrees Celsius. FIG. 18A shows the X-ray powder diffraction patterns of the solvate crystals, and desolvation of the crystals yielded a semi-crystalline phase. The desolvated crystals were obtained by allowing solvate crystals equilibrate at ambient temperature followed by further drying at 30 degrees Celsius under vacuum (approximately 3 inches of mercury). FIG. 18B shows the X-ray powder diffraction patterns of the desolvated solvate.

Example 28

Crystals of ABT-578 methyl ethyl ketone solvate were prepared by dissolving 94 mg of amorphous ABT-578 in 200 uL of methyl ethyl ketone at ambient temperature and storing at −12 degrees Celsius for 30 hours before seeded with a trace amount of toluene solvate crystals. Crystalline solids formed after seeding by further incubation at −12 degrees Celsius. FIG. 19A shows the X-ray powder diffraction pattern of the solvate crystals, and desolvation of the crystals yielded a semi-crystalline phase. The desolvated crystals were obtained by allowing solvate crystals equilibrate at ambient temperature followed by further drying at 30 degrees Celsius under vacuum (approximately 3 inches of mercury). FIG. 19B shows the X-ray powder diffraction patterns of the desolvated solvate.

Example 29

Crystals of ABT-578 tetrahydrofuran solvate were prepared by dissolving 107 mg of amorphous ABT-578 in 200 uL of tetrahydrofuran at ambient temperature and storing at −12 degrees Celsius for 30 hours before seeded with a trace amount of toluene solvate crystals. Crystalline solids formed after seeding by further incubation at −12 degrees Celsius. FIG. 20A shows the X-ray powder diffraction pattern of the crystals, and desolvation of the crystals yielded a semi-crystalline phase. The desolvated crystals were obtained by allowing solvate crystals equilibrate at ambient temperature followed by further drying at 30 degrees Celsius under vacuum (approximately 3 inches of mercury). FIG. 20B shows the X-ray powder diffraction patterns of the desolvated solvate.

Example 30

Crystals of ABT-578 1,2-dimethoxyethane solvate were prepared by dissolving 110 mg of amorphous ABT-578 in 200 uL of 1,2-dimethoxyethane at ambient temperature and storing at −12 degrees Celsius for 30 hours before seeded with a trace amount of toluene solvate crystals. Crystalline solids formed after seeding by further incubation at −12 degrees Celsius. FIG. 21A shows the X-ray powder diffraction pattern of the solvate crystals, and desolvation of the crystals yielded a semi-crystalline phase. The desolvated crystals were obtained by allowing solvate crystals equilibrate at ambient temperature followed by further drying at 30 degrees Celsius under vacuum (approximately 3 inches of mercury). FIG. 21B shows the X-ray powder diffraction patterns of the desolvated solvate.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended. Additionally, all publications recited herein are incorporated herein by specific reference.

What is claimed is:

1. A process for preparing a crystalline form of a compound, or a pharmaceutically acceptable salt thereof, of Formula 1

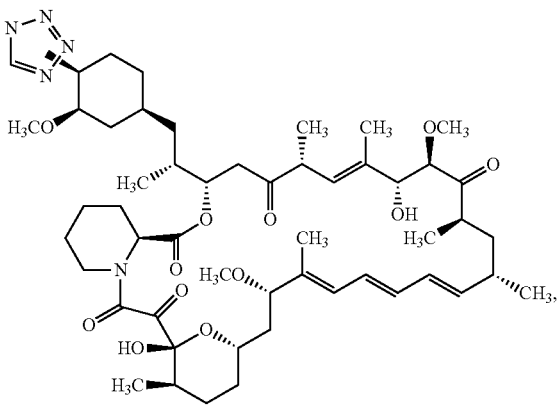

FORMULA 1 the process comprising:
  combining the compound or salt thereof with at least one organic solvent to form a mixture; and
  incubating the mixture until the compound crystallizes.

2. The process of claim 1, further comprising causing the compound or salt thereof to dissolve into the organic solvent.

3. The process of claim 1, further comprising recovering the crystalline compound or salt thereof from the organic solvent.

4. The process of claim 1, further comprising:
  combining at least one antisolvent with the compound or salt thereof and the solvent to form a biphasic mixture; and
  incubating the biphasic mixture to cause a liquid-liquid phase split with a majority of the compound or salt thereof being in the solvent and a minority of the compound being in the anti solvent.

5. The process of claim 4, further comprising separating the organic solvent from the antisolvent.

6. The process of claim 4, wherein the antisolvent comprises at least one of cyclohexane, heptane, hexane, n-octane, iso-octane, methylcyclohexane, or any combination thereof.

7. The process of claim 1, wherein the organic solvent is a polar organic solvent.

8. The process of claim 1, wherein the organic solvent comprises at least one of acetone, ethyl acetate, methanol, ethanol, n-propanol, isopropanol, isobutanol, tertbutanol, 2-butanol, acetonitrile, tetrahydrofuran, isobutyl acetate, n-butyl acetate, ethyl formate, n-propyl acetate, isopropyl acetate, methylethyl ketone, toluene, N,N dimethyl formamide, anisole, methyl isopropyl ketone, nitromethane, propionitrile, 2-butanone, 1,2-dimethoxyethane, or any combination thereof.

9. The process of claim 1, further comprising combining the mixture with a second organic solvent, and wherein the mixture being incubated includes the second organic solvent.

10. The process of claim 9, wherein the second the organic solvent comprises at least one of ethyl formate, isopropyl acetate, ethanol, N, N-dimethyl formamide, anisole, or combination thereof.

11. The process of claim 1, further comprising forming a slurry of crystalline compound or salt thereof.

12. The process of claim 1, further comprising stirring said mixture until the compound or salt thereof crystallizes.

13. The process of claim 1, further comprising saturating the mixture.

14. The process of claim 13, further comprising introducing a nucleation or precipitation event.

15. The process of claim 14, wherein the nucleation or precipitation event is subjecting the mixture to ultrasound or mechanical stimulation or by adding an additional component.

16. The process of claim 1, wherein the incubating is conducted at a temperature from about −20 degrees Celsius to about 20 degrees Celsius.

17. The process of claim 16, wherein the incubating is conducted at a temperature from about −10 degrees Celsius to about 10 degrees Celsius or about −5 degrees Celsius to about 5 degrees Celsius.

18. The process of claim 1, wherein the incubating is conducted at a temperature from about 12 degrees Celsius to about 32 degrees Celsius, about 20 degrees Celsius to about 25 degrees Celsius, or about 22 degrees Celsius.

19. The process of claim 1, wherein the compound or salt thereof combined with the organic solvent is a crystalline form.

20. The process of claim 1, wherein the compound or salt thereof combined with the organic medium is in an amorphous form.

21. The process of claim 1, wherein the crystalline form of the compound or salt thereof is in the form of a solvate or a desolvate thereof.

22. The process of claim 21, wherein the crystalline form is a solvate having a form represented by the X-ray diffraction pattern substantially as shown in:
FIG. 2A;
FIG. 2B;
FIG. 4A;
FIG. 4B;
FIG. 5A;
FIG. 5B;
FIG. 7A;
FIG. 7B;
FIG. 9A;
FIG. 9B;
FIG. 10A;
FIG. 10B;
FIG. 11A;
FIG. 11B;
FIG. 13A;
FIG. 14A;
FIG. 16;
FIG. 15A;
FIG. 12A;
FIG. 17A;
FIG. 18A;
FIG. 19A;
FIG. 20A; or
FIG. 21A.

23. The process as in claim 21, wherein the crystalline form is a desolvate having a form represented by the X-ray diffraction pattern substantially as shown in:
FIG. 3A;
FIG. 3B;
FIG. 6A;
FIG. 6B;
FIG. 4E;
FIG. 13B;
FIG. 14B;
FIG. 15B;
FIG. 8;
FIG. 12B;
FIG. 17B;
FIG. 18B;
FIG. 19B;
FIG. 20B; or
FIG. 21B.

24. The process of claim 1, wherein the crystalline form is an acetonitrile solvate or a desolvate thereof, an acetone solvate or a desolvate thereof, a toluene solvate, an ethyl formate solvate, a hydrate, an isopropyl solvate, an isobutyl solvate, an ethanol solvate, a N,N-dimethyl formamide solvate, or an anisole solvate.

25. The process of claim 1, wherein the crystalline form is polymorphous.

* * * * *